United States Patent

Baxter et al.

[11] Patent Number: 5,952,478
[45] Date of Patent: Sep. 14, 1999

[54] INTERMEDIATES FOR DINUCLEOTIDE AND OLIGONUCLEOTIDE ANALOGUES

[75] Inventors: Anthony David Baxter, Near Abingdon; Roger John Taylor, Macclesfield; Stephen Paul Collingwood, Wilmslow, all of United Kingdom

[73] Assignee: Novartis Finance Corporation, New York, N.Y.

[21] Appl. No.: 08/793,725

[22] PCT Filed: Aug. 17, 1995

[86] PCT No.: PCT/GB95/01955

§ 371 Date: Apr. 14, 1997

§ 102(e) Date: Apr. 14, 1997

[87] PCT Pub. No.: WO96/08503

PCT Pub. Date: Mar. 21, 1996

[30] Foreign Application Priority Data

Sep. 3, 1994 [GB] United Kingdom ............... 9417746

[51] Int. Cl.$^6$ ..................... C07H 19/00; C07H 21/02; C07H 21/04; A01N 43/04
[52] U.S. Cl. ..................... 536/22.1; 536/23.1; 536/24.5; 514/1; 514/44
[58] Field of Search ............... 536/22.1, 23.1, 536/24.5; 514/1, 44

[56] References Cited

FOREIGN PATENT DOCUMENTS

| | | |
|---|---|---|
| 0121112 | 10/1984 | European Pat. Off. . |
| 0614907 | 9/1994 | European Pat. Off. . |
| 0629633 | 12/1994 | European Pat. Off. . |
| 9115499 | 10/1991 | WIPO . |
| 9220822 | 11/1992 | WIPO . |
| 9220823 | 11/1993 | WIPO . |

*Primary Examiner*—Ardin H. Marschel
*Assistant Examiner*—Jezia Riley
*Attorney, Agent, or Firm*—Myra H. McCormack

[57] ABSTRACT

A compound of formula (I) or salts thereof, where $R^0$ is hydrogen or together with $R^7O$ denotes a $C_1$–$C_{15}$ hydrocarbylidenedioxy group, $R^1$ is hydrogen, $R^1_a$ or a group of formula (II), $R^1_a$ is $R^1_b$ or a protecting group Q, $R^1_b$ is $C_1$–$C_{20}$ alkyl, $C_2$–$C_{20}$ alkenyl, $C_3$–$C_{10}$ cycloalkyl, $C_6$–$C_{15}$ aryl, $C_7$–$C_{16}$ aralkyl or a 5- or 6-membered heterocyclic group attached by a carbon atom in the heterocyclic group to the indicated phosphorus atom, $R^2$ is $R^2_a$ or —$OR^{15}$ or together with $R^5$ denotes an oxy group —O—, provided that $R^2$ is —$OR^{15}$ when $R^1$ is a group of formula (II), $R^2_a$ is a $C_1$–$C_{20}$ aliphatic group, a $C_3$–$C_{10}$ cycloaliphatic group, a $C_6$–$C_{15}$ aromatic group, a $C_7$–$C_{16}$ aralphatic group, or a 5- or 6-membered heterocyclic group attached by a carbon atom in the heterocyclic group to the indicated phosphorus atom, $R^3$ is $R^3_a$ or Z, $R^3_a$ is hydrogen, halogen, hydroxy, $R^{16}$, —$OR^{16}$, $OCOR^{16}$, —$OSO_2R^{16}$, or tri($C_1$–$C_{15}$ hydrocarbyl)silyloxy, $R^4$ is hydrogen, halogen or $R^{17}$, $R^5$ is $R^5_a$ or Z or together with $R^2$ denotes an oxy group —O—, $R^5_a$ is hydrogen, halogen, hydroxy, $R^{18}$, —$OR^{18}$, —$OCOR^{18}$, —$OSO_2R^{18}$, or tri($C_1$–$C_{15}$ hydrocarbyl) silyloxy, or together with $R^6$ denotes a $C_1$–$C_{15}$ hydrocarbylidenedioxy group, $R^6$ is halogen, hydroxy, —$OR^{19}$, —$OCOR^{19}$, —$OSO_2R^{19}$ or $B^1$, or together with $R^5$ denotes a $C_1$–$C_{15}$ hydrocarbylidenedioxy group, provided that $R^6$ is not $B^1$ when $R^1$ is a group of formula (II) in which $R^{14}$ is $B^2$, $R^7$ is hydrogen or $R^7_a$, $R^7_a$ is $R^{20}$, —$COR^{20}$, —$SO_2R^{20}$ or tri($C_1$–$C_{15}$ hydrocarbyl)silyl, or together with the attached oxygen atom and $R^0$ denotes a $C_1$–$C_{15}$ hydrocarbylidenedioxy group, $R^8$ is hydrogen, halogen, hydroxy, $R^{21}$, —$OR^{21}$, —$OCOR^{21}$, —$OSO_2R^{21}$ or together with $R^{10}$ denotes a valence bond, $R^9$ is hydrogen, halogen or $R^{22}$, $R^{10}$ is hydrogen, halogen, hydroxy, $R^{23}$, —$OR^{23}$, —$OCOR^{23}$ or —$OSO_2R^{23}$, or together with $R^8$ denotes a valence bond, $R^{11}$ is hydrogen, halogen or $R^{24}$, $R^{12}$ is hydrogen or $R^{12}_a$, or $R^{12}O$— together with $R^{13}$ denotes a $C_1$–$C_{15}$ hydrocarbylidenedioxy group, $R^{12}_a$ is $R^{25}$, —$COR^{25}$, —$SO_2R^{25}$ or tri($C_1$–$C_{15}$ hydrocarbyl)silyl, $R^{13}$ is $R^{13}_a$ or Z, $R^{13}_a$ is hydrogen, halogen, hydroxy, $R^{26}$, —$OR^{26}$, —$OCOR^{26}$, —$OSO_2R^{26}$ or tri($C_1$–$C_{15}$ hydrocarbyl)silyloxy, or together with $R^{14}$ denotes a $C_1$–$C_{15}$ hydrocarbylidenedioxy group, or together with $R^{12}O$— denotes a $C_1$–$C_{15}$ hydrocarbylidenedioxy group, $R^{14}$ is halogen, hydroxy, —$OR^{27}$, —$OCOR^{27}$, —$OSO_2R^{27}$, or $B^2$ or together with $R^{13}$ denoted a $C_1$–$C_{15}$ hydrocarbylidenedioxy group, provided that $R^{14}$ is not $B^2$ when $R^6$ is $B^1$, $R^{15}$ is hydrogen or $R^{15}_a$, $R^{15}_a$ is a $C_1$ to $C_{10}$ aliphatic group, a $C_3$ to $C_8$ cycloaliphatic group, a $C_6$ to $C_{15}$ aromatic group or a $C_7$ to $C_{16}$ aralphatic group, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$ are independently a $C_1$ to $C_{10}$ aliphatic group, a $C_3$ to $C_{10}$ cycloaliphatic group, a $C_6$ to $C_{15}$ aromatic group or a $C_7$ to $C_{30}$ aralphatic group, $B^1$ and $B^2$ are independently each a monovalent nucleoside base radical, and Z is substituted or unsubstituted $C_6$ to $C_{10}$ aryloxythiocarbonyloxy.

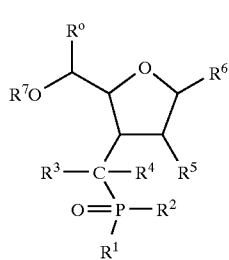

(I)

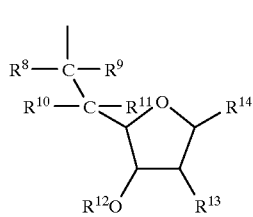

(II)

24 Claims, No Drawings

INTERMEDIATES FOR DINUCLEOTIDE AND OLIGONUCLEOTIDE ANALOGUES

This is a 371 of PCT No: GB95/01955 filed Aug. 17, 1995.

This invention relates to compounds which are intermediates for dinucleotide analogues and oligonucleotide analogues, the preparation of these compounds, and their use in preparing dinucleotide analogues and their use as pharmaceuticals.

For several years there has been interest in structural analogues of natural oligonucleotides because of their utility as anti-sense probes for inhibiting gene expression in biological systems and as pharmaceuticals in the treatment of viruses such as influenza, herpes and HIV, and in the treatment of cancer. Amongst the analogues of recent interest are those in which the groups linking the sugar moieties of oligonucleotides are modified by the replacement of the 3' and 5' oxy linkages by other linking groups.

WO 92/20822 describes oligonucleotide analogues comprising subunits at least some of which have the general structure

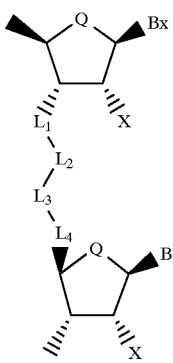

wherein $B_x$ is a variable base moiety; Q is O, $CH_2$, CHF or $CF_2$; X is H, OH, $C_1$ to $C_{10}$ lower alkyl, substituted lower alkyl, alkaryl, or aralkyl, F, Cl, Br, CN, $CF_3$, $OCF_3$, OCN, O—, S—, or N-alkyl, O—, S—, or N-alkenyl, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a group for improving the pharmacokinetic properties of an oligonucleotide or a group for improving the pharmacodynarnic properties of an oligonucleotide;

$L_1$ and $L_4$ are, independently, $CH_2$, C=O, C=S, C—$NH_2$, C—$NHR_3$, C—OH, C—SH, C—O—$R_1$ or C—S—$R_1$ and $L_2$ and $L_3$ are, independently, $CR_1R_2$, $C=CR_1R_2$, $C=NR_3$ P(O)$R_4$, P(S)$R_4$, C=O, C=S, O, S, SO, $SO_2$, $NR_3$ or $SiR_5R_6$ or $L_2$ and $L_3$ together form part of an alkene, alkyne, aromatic ring, carbocycle or heterocycle, or $L_1$, $L_2$, $L_3$ and $L_4$ together comprise a —CH=N—NH—$CH_2$— or $CH_2$—O—N=CH— moiety;

$R_1$ and $R_2$ are independently H, OH, SH, $NH_2$, $C_1$ to $C_{10}$ alkyl, substituted alkyl, alkenyl, alkaryl or aralkyl, alkoxy, thioalkoxy, alkylamino, aralkylamino, substituted alkylamino, heterocycloalkyl, heterocycloalkylamino, aminoalkylamino, polyalkylamino, halo, formyl, keto, benzoxy, carboxamido, thiocarboxamido, ester, thioester, carboxamidine, carbamyl, ureido, guanidino, an RNA cleaving group, a group for improving the pharmacokinetic properties of an oligonucleotide, or a group for improving the pharmacodynamic properties of an oligonucleotide;

$R_3$ is H, OH, $NH_2$, lower alkyl, substituted lower alkyl, alkoxy, lower alkenyl, aralkyl, alkylamino, aralkylamino, substituted alkylamino, heterocycloalkyl, heterocycloalkylamino, aminoalkylamino, polyalkylamino, a RNA cleaving group, a group for improving the pharmacokinetic properties of an oligonucleotide or a group for improving the pharmacodynarnic properties of an oligonucleotide;

$R_4$ is OH, SH, $NH_2$, O-alkyl, S-alkyl, NH-alkyl, O-alkylheterocyclo, S-alkylheterocyclo, N-alkylheterocyclo or a nitrogen-containing heterocycle; and $R_5$ and $R_6$ are, independently, $C_1$ to $C_6$ alkyl or alkoxy; provided that if $L_1$ is C=O or C=S then $L_2$ is not $NR_3$ or if $L_4$ is C=O or C=S then $L_3$ is not $NR_3$; that if one of $L_2$ or $L_3$ is C=O or C=S then the other of $L_2$ or $L_3$ is not $NR_3$; that if $L_2$ is P(O)$R_4$ and $R_4$ is OH and X is OH and $B_x$ is uracil or adenine, then $L_3$ is not O; and that if $L_1$, $L_2$ and $L_4$ are $CH_2$ and X is H or OH and Q is O then $L_3$ is not S, SO or $SO_2$.

WO 91/15499 describes oligonucleotides of formula

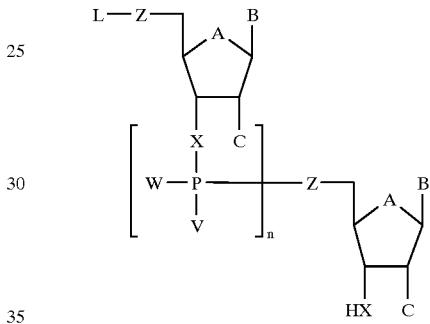

where B is a nucleic acid base; A is —O— or —$CH_2$—; X and Z are each —O—, —S—, —NH— or —$CH_2$— where X and Z may be the same or different; V and W are =O, =S, =Se, —$NH_2$, alkoxy, —OH or —SH, where V and W may be the same or different in a monomer unit; L is —H or a partner of a bonding pair; C is —OR where R is an alkyl, alkenyl or alkynyl group optionally substituted by one or more halogen, cyano, carboxy, hydroxy, nitro and/or mercapto radicals; and n is any integer.

No compounds of the above formula where X and Z are each —$CH_2$— are disclosed in WO 91/15499 and there is no suggestion as to how such compounds might be prepared. The preparation of oligonucleotide analogues in which both the 3' oxy linkage and the 5' oxy linkage are replaced by carbon linkages has remained a significant problem. It has now been found that dinucleotide analogues, and hence oligonucleotide analogues, in which both the 3' oxy linkage and the 5' oxy linkage are replaced by carbon linkages can be obtained from certain novel intermediates. These intermediates may themselves be used as pharmaceuticals in the treatment of diseases such as cancer, viruses such as influenza, herpes and HIV, and diseases which are mediated through inhibition or activation of enzymes/receptors which recognize nucleotide 3' monophosphates as substrates or ligands.

Accordingly, the present invention provides compounds of formula

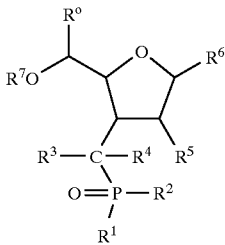

I or salts thereof, where $R^0$ is hydrogen or together with $R^7O$ denotes a $C_1$–$C_{15}$ hydrocarbylidenedioxy group, $R^1$ is hydrogen, $R^1{}_a$ or a group of formula

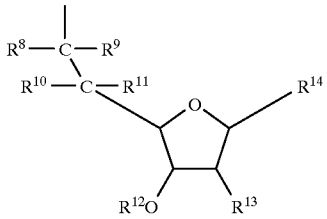

II $R^1{}_a$ is $R^1{}_b$ or a protecting group Q, $R^1{}_b$ is $C_1$–$C_{20}$ alkyl, $C_2$–$C_{20}$ alkenyl, $C_3$–$C_{10}$ cycloalkyl, $C_6$–$C_{15}$ aryl, $C_7$–$C_{16}$ aralkyl or a 5- or 6- membered heterocyclic group attached by a carbon atom in the heterocyclic group to the indicated phosphorus atom.

$R^2$ is $R^2{}_a$ or —$OR^{15}$ or together with $R^5$ denotes an oxy group —O—, provided that $R^2$ is —$OR^{15}$ when $R^1$ is a group of formula II, $R^2{}_a$ is a $C_1$–$C_{20}$ aliphatic group, a $C_3$–$C_{10}$ cycloaliphatic group, a $C_6$–$C_{15}$ aromatic group, a $C_7$–$C_{16}$ araliphatic group, or a 5- or 6-membered heterocyclic group attached by a carbon atom in the heterocyclic group to the indicated phosphorus atom, $R^3$ is $R^3{}_a$ or Z, $R^3{}_a$ is hydrogen, halogen, hydroxy, $R^{16}$, —$OR^{16}$, $OCOR^{16}$, —$OSO_2R^{16}$, or tri($C_1$–$C_{15}$ hydrocarbyl)silyloxy, $R^4$ is hydrogen, halogen or $R^{17}$, $R^5$ is $R^5{}_a$ or Z or together with $R^2$ denotes an oxy group —O—, $R^5{}_a$ is hydrogen, halogen, hydroxy, $R^{18}$, —$OR^{18}$, —$OCOR^{18}$, —$OSO_2R^{18}$, or tri($C_1$–$C_{15}$ hydrocarbyl) silyloxy, or together with $R^6$ denotes a $C_1$–$C_{15}$ hydrocarbylidenedioxy group, $R^6$ is halogen, hydroxy, —$OR^{19}$, —$OCOR^{19}$, —$OSO_2R^{19}$ or $B^1$, or together with $R^5$ denotes a $C_1$–$C_{15}$ hydrocarbylidenedioxy group, provided that $R^6$ is not $B^1$ when $R^1$ is a group of formula II in which $R^{14}$ is $B^2$, $R^7$ is hydrogen or $R^7{}_a$, $R^7{}_a$ is $R^{20}$, —$COR^{20}$, —$SO_2R^{20}$ or tri($C_1$–$C_{15}$ hydrocarbyl)silyl, or together with the attached oxygen atom and $R^0$ denotes a $C_1$–$C_{15}$ hydrocarbylidenedioxy group, $R^8$ is hydrogen, halogen, hydroxy, $R^{21}$, —$OR^{21}$, —$OCOR^{21}$, —$OSO_2R^{21}$ or together with $R^{10}$ denotes a valence bond, $R^9$ is hydrogen, halogen or $R^{22}$, $R^{10}$ is hydrogen, halogen, hydroxy, $R^{23}$, —$OR^{23}$, —$OCOR^{23}$ or —$OSO_2R^{23}$, or together with $R^8$ denotes a valence bond, $R^{11}$ is hydrogen, halogen or $R^{24}$, $R^{12}$ is hydrogen or $R^{12}{}_a$, or $R^{12}O$— together with $R^{13}$ denotes a $C_1$–$C_{15}$ hydrocarbylidenedioxy group, $R^{12}{}_a$ is $R^{25}$, —$COR^{25}$, —$SO_2R^{25}$ or tri($C_1$–$C_{15}$ hydrocarbyl) silyl, $R^{13}$ is $R^{13}{}_a$ or Z, $R^{13}{}_a$ is hydrogen, halogen, hydroxy, $R^{26}$, —$OR^{26}$, —$OCOR^{26}$, —$OSO_2R^{26}$ or tri($C_1$–$C_{15}$ hydrocarbyl) silyloxy, or together with $R^{14}$ denotes a $C_1$–$C_{15}$ hydrocarbylidenedioxy group, or together with $R^{12}O$— denotes a $C_1$–$C_{15}$ hydrocarbylidenedioxy group, $R^{14}$ is halogen, hydroxy, —$OR^{27}$, —$OCOR^{27}$, —$OSO_2R^{27}$ or $B^2$ or together with $R^{13}$ denotes a $C_1$–$C_{15}$ hydrocarbylidenedioxy group, provided that $R^{14}$ is not $B^2$ when $R^6$ is $B^1$, $R^{15}$ is hydrogen or $R^{15}{}_a$, $R^{15}{}_a$ is a $C_1$ to $C_{10}$ aliphatic group, a $C_3$ to $C_8$ cycloaliphatic group, a $C_6$ to $C_{15}$ aromatic group or a $C_7$ to $C_{16}$ araliphatic group, $R^{16}$, $R^{17}$, $R^{18}$, $R^{19}$, $R^{20}$, $R^{21}$, $R^{22}$, $R^{23}$, $R^{24}$, $R^{25}$, $R^{26}$ and $R^{27}$ are independently a $C_1$ to $C_{10}$ aliphatic group, a $C_3$ to $C_{10}$ cycloaliphatic group, a $C_6$ to $C_{15}$ aromatic group or a $C_7$ to $C_{30}$ araliphatic group, $B^1$ and $B^2$ are independently each a monovalent nucleoside base radical, and Z is substituted or unsubstituted $C_6$ to $C_{10}$ aryloxythiocarbonyloxy.

In compounds of formula I, generally the aliphatic groups are substituted or unsubstituted alkyl or alkenyl groups, the cycloaliphatic groups are substituted or unsubstituted cycloalkyl groups, the aromatic groups are substituted or unsubstituted aryl groups and the araliphatic groups are substituted or unsubstituted aralkyl groups. Suitable substituents include halogen, hydroxy, etherified hydroxy, esterified hydroxy, cyano, nitro, amino, $C_1$–$C_8$ alkylamino, di ($C_1$–$C_8$ alkyl)amino or phosphonic ester groups.

The substituted or unsubstituted alkyl groups may be, for example, substituted or unsubstituted methyl, ethyl, n-propyl, isopropyl, n-butyl, isobutyl, tert-butyl, n-pentyl, neopentyl, n-hexyl, n-octyl, 2-ethylhexyl or n-decyl. $R^1$ or $R^2$ as substituted or unsubstituted $C_1$ to $C_{20}$ alkyl may additionally be, for example, substituted or unsubstituted n-dodecyl, n-tetradecyl, n-hexadecyl, n-octadecyl or eicosyl.

The substituted or unsubstituted alkenyl groups may be, for example, substituted or unsubstituted vinyl, allyl, 1-propenyl, isopropenyl, methallyl, 2-butenyl, 1-butenyl, isobutenyl, pentenyl, hexenyl, octenyl or decenyl. $R^1$ or $R^2$ as substituted or unsubstituted alkenyl may additionally be, for example, dodecenyl, hexadecenyl, octadecenyl or eicosenyl.

The substituted or unsubstituted cycloalkyl groups may be, for example, substituted or unsubstituted cyclopropyl, cyclobutyl, cyclopentyl, methylcyclopentyl, cyclohexyl, methylcyclohexyl, dimethylcyclohexyl, tert-butylcyclohexyl, cycloheptyl or cyclooctyl. The substituted or unsubstituted aryl groups may be, for example, substituted or unsubstituted phenyl, o-tolyl, m-tolyl, p-tolyl, o-xylyl, m-xylyl, p-xylyl, alpha-naphthyl, beta-naphthyl, dimethylnaphthyl or anthryl.

$R^1$, $R^2$ or $R^{15}$ as substituted or unsubstituted $C_7$ to $C_{16}$ aralkyl may be, for example, substituted or unsubstituted benzyl, 4-methylbenzyl, 2-phenylethyl, 2-phenylpropyl, 3-phenylpropyl or diphenylmethyl. The other substituted or unsubstituted $C_7$ to $C_{30}$ aralkyl groups may be, for example, substituted or unsubstituted benzyl, 4-methylbenzyl, 2-phenylethyl, 2-phenylpropyl, 3-phenylpropyl, diphenylmethyl or triphenylmethyl.

Preferably, the alkyl groups are $C_1$ to $C_8$ alkyl, the alkenyl groups are $C_2$ to $C_4$ alkenyl, the cycloalkyl groups are $C_5$ to $C_8$ cycloalkyl, the aryl groups $C_6$ to $C_{10}$ aryl, the $C_7$ to $C_{16}$ aralkyl group is $C_7$ to $C_9$ aralkyl and the $C_7$ to $C_{30}$ aralkyl groups are $C_7$ to $C_{20}$ aralkyl, any of which are substituted or unsubstituted. More preferably, these groups are unsubstituted or substituted by halogen, hydroxy, $C_1$ to $C_4$ alkoxy, cyano, nitro, amino, $C_1$ to $C_4$ alkylamino, di($C_1$–$C_4$ alkyl) amino, tri($C_1$–$C_{15}$hydrocarbyl)silyl, tri($C_1$–$C_{15}$hydrocarbyl) silyloxy or, in the case of $R^1$ as $C_1$ to $C_8$ alkyl, by a phosphonic ester group. Especially preferred are the unsubstituted groups and, for $R^1$, methyl substituted by a diethylphosphonate group. i.e. a group of formula —P(O) (OCH$_2$CH$_3$)$_2$ and, for $R^{15}$, $C_1$ to $C_8$ alkyl substituted by cyano.

When $R^1$ in formula I is a protecting group Q, this may be any group which is known to be effective in protecting P—H bonds whilst reactions are carried out which would affect such bonds and be readily removable after such reactions to generate a P—H bond. Such protecting groups may be, for example, those in compounds of formula Ia of EP 0009348, or those in compounds described in Aust. J. Chem. 33, 292 (1980) or U.S. Pat. No. 4,933,478. Preferred protecting groups Q are $C_1$ to $C_{20}$ hydrocarbyl groups, preferably alkyl groups, substituted on the carbon atom thereof attached to the indicated phosphorus atom by at least one hydroxy, $C_1$–$C_{10}$ alkoxy, di($C_1$–$C_{15}$ hydrocarbyl) silyloxy or tri($C_1$–$C_{15}$ hydrocarbyl)silyloxy group, including those of formulae

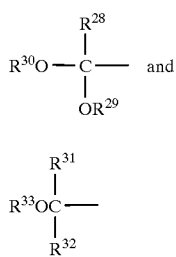

where $R^{28}$ is hydrogen, $C_1$–$C_{10}$ alkyl, $C_3$–$C_8$ cycloalkyl, $C_6$–$C_{10}$ aryl or $C_7$–$C_{11}$ aralkyl, $R^{29}$ and $R^{30}$ are independently $C_1$–$C_{10}$ alkyl, $C_2$–$C_4$ alkenyl, $C_6$–$C_{10}$ aryl or $C_7$–$C_{13}$ aralkyl $R^{31}$ and $R^{32}$ are independently $C_1$–$C_{10}$ alkyl, or $R^{31}$ is $C_1$–$C_{10}$ alkyl and $R^{32}$ is $C_6$–$C_{10}$ aryl, and $R^{33}$ is hydrogen, di($C_1$–$C_{15}$ hydrocarbyl)silyl or tri($C_1$–$C_{15}$ hydrocarbyl)silyl. Preferred groups of formula III are those where $R^{28}$ is hydrogen or $C_1$–$C_4$ alkyl and $R^{29}$ and $R^{30}$ are each $C_1$–$C_4$ alkyl. Preferred groups of formula IIIA are those where $R^{31}$ and $R^{32}$ are $C_1$–$C_4$ alkyl, and $R^{33}$ is hydrogen or branched $C_2$–$C_{10}$ alkyl di($C_1$–$C_4$ alkyl)silyl. In especially preferred compounds, Q is a group of formula III where $R^{28}$ is hydrogen or methyl and $R^{29}$ and $R^{30}$ are each methyl or ethyl or a group of formula IIIA where $R^{31}$ and $R^{32}$ are each methyl and $R^{33}$ is hydrogen or tert-butyl dimethylsilyl.

When a tri($C_1$–$C_{15}$ hydrocarbyl)silyl or tri($C_1$–$C_{15}$ hydrocarbyl)silyloxy group is present in compounds of formula I, the tri($C_1$–$C_{15}$ hydrocarbyl)silyl radical may be, for example, trialkylsilyl such as trimethylsilyl, triethysilyl, tri-n-propylsilyl, tri-isopropysilyl, tri-n-butylsilyl, tri-isobutysilyl, tri-tert-butylsilyl, isopropyldimethylsilyl, tert-.butyldimethylsilyl or 1,1,2,2-tetraethylethyldimethylsilyl (thexyldimethylsilyl), aryldialkylsilyl such as phenyldimethylsilyl, phenyldiethylsilyl, phenyldiisopropylsilyl or phenyl di-tert-butylsilyl, or alkyldiarylsilyl such as isopropyldiphenylsilyl or tert-butyldiphenylsilyl, preferably tri($C_1$–$C_6$ alkyl)silyl, especially trimethylsilyl, $C_1$–$C_6$ alkyldi($C_6$–$C_8$ aryl)silyl, especially tert-butyldiphenylsilyl, or branched $C_2$–$C_{10}$ alkyl di ($C_1$–$C_4$ alkyl)silyl, especially thexyldimethylsilyl.

When a $C_1$–$C_{15}$ hydrocarbylidenedioxy group is present in compounds of formula I, this may be a group of formula

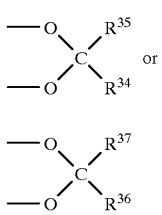

where $R^{34}$, $R^{35}$, $R^{36}$ and $R^{37}$ are independently hydrogen, $C_1$ to $C_{10}$ alkyl, $C_3$ to $C_8$ cycloalkyl or $C_6$ to $C_{10}$ aryl. Preferred such groups are those where $R^{34}$, $R^{35}$, $R^{36}$ and $R^{37}$ are $C_1$ to $C_4$ alkyl, particularly methyl or ethyl. An especially preferred $C_1$–$C_{15}$ hydrocarbylidenedioxy group is an isopropylidenedioxy group.

$R^3$, $R^5$ or $R^{13}$ as substituted or unsubstituted $C_6$–$C_{10}$ aryloxythiocarbonyloxy may be, for example, substituted or unsubstituted phenyloxythiocarbonyloxy, preferably $C_1$–$C_4$ alkyl- or halogen- substituted phenyloxythiocarbonyloxy, especially p-tolyloxythiocarbonyloxy or pentafluorophenoxythiocarbonyloxy.

$R^6$ or $R^{14}$ as a monovalent nucleoside base radical $B^1$ or $B^2$ respectively may be a radical of a naturally occuring nucleoside base, such as adeninyl, cytosinyl, thyminyl, guaninyl or uracilyl, which may be unsubstituted or substituted for example on a carbon atom by an alkyl group, usually $C_1$–$C_4$ alkyl or on an amino nitrogen atom by an acyl group such as acetyl, an aralkyl oxyalkyl group such as benzyloxymethyl or an aracyl group such as benzoyl or nitrobenzoyl, or a synthetic base analogue thereof, or a radical of an imine derivative of a primary amino group containing base. Preferably, $R^6$ or $R^{14}$ as a monovalent nucleoside base radical is unsubstituted or substituted thyminyl, uracilyl, cytosinyl or adeninyl, especially thyminyl, N-benzyloxymethylthyminyl, uracilyl, methylcytosinyl, adeninyl, N-benzoyladeninyl, or N-(N-methyl-2-pyrrolidinylydene)-5-methylcytosinyl.

$R^1$ is preferably hydrogen, $C_1$–$C_4$ alkyl, especially methyl or methyl substituted by —P(O)(OCH$_2$CH$_3$)$_2$, $C_6$–$C_{10}$ aryl, especially phenyl, a protecting group Q of formula III or III A as hereinbefore defined, or a group of formula II as hereinbefore defined.

$R^2$ as $R^2{}_a$ is preferably $C_1$ to $C_4$ alkyl, more preferably methyl or ethyl; $C_2$ to $C_4$ alkenyl, more preferably vinyl or allyl; $C_5$ to $C_8$ cycloalkyl, more preferably cyclopentyl, cyclohexyl or methylcyclohexyl; $C_6$ to $C_{10}$ aryl, more preferably phenyl, tolyl or naphthyl; or $C_7$ to $C_9$ aralkyl, more preferably benzyl. $R^2$ as $R^2{}_a$ is especially methyl.

In compounds where $R^2$ is —OR$^{15}$, $R^{15}$ may be hydrogen, or substituted or unsubstituted $C_1$ to $C_8$ alkyl, $C_2$ to $C_4$ alkenyl or $C_7$ to $C_{13}$ aralkyl, for example n-hexyl, n-octyl, 2-(tri($C_1$–$C_{15}$ hydrocarbyl)silyl)ethyl, 2-($C_1$–$C_4$ alkoxy) ethyl, allyl, benzyl or p-methoxybenzyl. $R^{15}$ is preferably hydrogen or unsubstituted or substituted $C_1$–$C_4$ alkyl, especially hydrogen, methyl, ethyl, 2-cyanoethyl or isobutyl.

Preferably $R^3$ is hydrogen, halogen (usually fluorine or chlorine), hydroxy, —OCOR$^{16}$ or OSO$_2$R$^{16}$ where $R^{16}$ is substituted or unsubstituted $C_1$ to $C_4$ alkyl or $C_6$ to $C_{10}$ aryl (more preferably methyl, ethyl, phenyl, tolyl or naphthyl), tri($C_1$–$C_6$ alkyl)silyloxy or $C_1$–$C_4$ alkyl- or halogen- substituted phenyloxythiocarbonyloxy, and $R^4$ is hydrogen or halogen. In some especially preferred compounds $R^3$ is hydrogen, hydroxy, trimethylsilyloxy, acetoxy or p-tolyloxythiocarbonyloxy and $R^4$ is hydrogen.

$R^5$ is preferably hydrogen, hydroxy or —$OR^{18}$, —$OCOR^{18}$ or —$OSO_2R^{18}$ where $R^{18}$ is unsubstituted or substituted $C_1$ to $C_4$ alkyl (more preferably methyl or ethyl) or unsubstituted or substituted $C_6$ to $C_{10}$ aryl (more preferably phenyl, tolyl or naphthyl), tri($C_1$–$C_{15}$ hydrocarbyl) silyloxy, or together with $R^2$ denotes an oxy group, or together with $R^6$ denotes a hydrocarbylidenedioxy group of formula IV where $R^{34}$ and $R^{35}$ are independently $C_1$ to $C_4$ alkyl. In certain especially preferred compounds, $R^5$ is hydrogen, hydroxy, acetoxy, tert-butyldiphenylsilyloxy, thexyldimethylsilyloxy, or together with $R^2$ denotes an oxy group, or together with $R^6$ denotes an isopropylidenedioxy group.

$R^6$ is preferably a monovalent nucleoside base radical $B^1$ as hereinbefore defined, more preferably unsubstituted or substituted thyminyl, uracilyl, cytosinyl or adeninyl, hydroxy or —$OCOR^{19}$ where $R^{19}$ is unsubstituted or substituted $C_1$ to $C_4$ alkyl, more preferably methyl or ethyl, or together with $R^5$ denotes a hydrocarbylidenedioxy group of formula IV where $R^{34}$ and $R^{35}$ are independently $C_1$ to $C_4$ alkyl. In certain especially preferred compounds, $R^6$ is thyminyl, N-benzyloxymethylthyminyl, uracilyl, 5-methylcytosinyl, adeninyl, N-benzoyladeninyl, N-(N-methyl-2-pyrrolidinylidene)-5-methylcytosinyl, hydroxy or acetoxy, or together with $R^5$ denotes an isopropylidenedioxy group.

$R^7$ is preferably hydrogen, substituted or unsubstituted $C_1$ to $C_4$ alkyl (more preferably methyl or ethyl), substituted or unsubstituted $C_7$ to $C_{20}$ aralkyl (more preferably benzyl, diphenylmethyl, triphenylmethyl, methoxytriphenylmethyl or dimethoxytriphenylmethyl), —$COR^{20}$ or —$SO_2R^{20}$ where $R^{20}$ is substituted or unsubstituted $C_1$ to $C_4$ alkyl or substituted or unsubstituted $C_6$ to $C_{10}$ aryl (more preferably phenyl, tolyl or naphthyl), or ($C_1$ to $C_6$ alkyl) di ($C_6$–$C_8$ aryl) silyl, or together with the attached oxygen atom and $R^0$ denotes a hydrocarbyiidenedioxy group of formula IV where $R^{34}$ and $R^{35}$ are independently $C_1$ to $C_4$ alkyl. In certain especially preferred compounds, $R^7$ is hydrogen, benzoyl, acetyl, benzyl, triphenylmethyl, dimethoxytriphenylmethyl, tert-butyldiphenylsilyl or together with the attached oxygen atom and $R^0$ denotes an isopropylidenedioxy group.

$R^8$ is preferably hydrogen, halogen (usually fluorine or chlorine), hydroxy, $C_1$ to $C_4$ alkyl (more preferably methyl or ethyl), $C_1$ to $C_4$ alkoxy (more preferably methoxy or ethoxy), $C_7$ to $C_9$ aralkyloxy (more preferably benzyloxy), or —$OCOR^{21}$ or —$OSO_2R^{21}$ where $R^{21}$ is $C_1$ to $C_4$ alkyl, particularly methyl or ethyl, or $C_6$ to $C_{10}$ aryl, particularly phenyl or p-tolyl, or together with $R^{10}$ denotes a valence bond and $R^9$ is hydrogen, halogen (usually fluorine or chlorine) or $C_1$ to $C_4$ alkyl, particularly methyl or ethyl. In especially preferred compounds, $R^8$ is hydrogen or together with $R^{10}$ denotes a valence bond, and $R^9$ is hydrogen.

Preferably $R^{10}$ is hydrogen, halogen (usually fluorine or chlorine), hydroxy, $C_1$ to $C_4$ alkyl (more preferably methyl or ethyl), $C_1$ to $C_4$ alkoxy (more preferably methoxy or ethoxy), $C_7$ to $C_9$ aralkyloxy (more preferably benzyloxy), or —$OCOR^{23}$ or —$OSO_2R^{23}$ where $R^{23}$ is $C_1$ to $C_4$ alkyl, particularly methyl or ethyl, or $C_6$ to $C_{10}$ aryl, particularly phenyl or p-tolyl, or together with $R^8$ denotes a valence bond and $R^{11}$ is hydrogen, halogen (usually fluorine or chlorine) or $C_1$ to $C_4$ alkyl, particularly methyl or ethyl. In especially preferred compounds, $R^{10}$ is hydrogen or together with $R^8$ denotes a valence bond, and $R^{11}$ is hydrogen.

$R^{12}$ is preferably hydrogen, $C_1$ to $C_4$ alkyl (more preferably methyl or ethyl), $C_7$ to $C_9$ aralkyl (more preferably benzyl), or —$COR^{25}$ or —$SO_2R^{25}$ where $R^{25}$ is substituted or unsubstituted $C_1$ to $C_4$ alkyl (more preferably methyl or ethyl) or substituted or unsubstituted $C_6$ to $C_{10}$ aryl (more preferably phenyl, tolyl or naphthyl). In some especially preferred compounds, $R^{12}$ is hydrogen, methyl, benzyl, acetyl, benzoyl or naphthoyl.

$R^{13}$ is preferably hydrogen, hydroxy or —$OR^{26}$, —$OCOR^{26}$ or —$OSO_2R^{26}$ where $R^{26}$ is substituted or unsubstituted $C_1$ to $C_4$ alkyl (more preferably methyl or ethyl), substituted or unsubstituted $C_7$ to $C_{13}$ aralkyl (more preferably benzyl) or substituted or unsubstituted $C_6$ to $C_{10}$ aryl (more preferably phenyl, tolyl or naphthyl), or together with $R^{14}$ denotes a hydrocarbylidenedioxy group of formula IVA where $R^{36}$ and $R^{37}$ are independently $C_1$ to $C_4$ alkyl. In certain especially preferred compounds, $R^{13}$ is hydrogen, hydroxy or acetoxy, or together with $R^{14}$ denotes an isopropylidenedioxy group.

Preferably. $R^{14}$ is hydroxy or —$OCOR^{27}$ where $R^{27}$ is substituted or unsubstituted $C_1$ to $C_4$ alkyl (more preferably methyl or ethyl), or together with $R^{13}$ denotes a hydrocarbylidenedioxy group of formula IVA where $R^{36}$ and $R^{37}$ are independently $C_1$ to $C_4$ alkyl. In certain especially preferred compounds, $R^{14}$ is hydroxy or acetoxy, or together with $R^{13}$ denotes an isopropylidenedioxy group.

More especially preferred compounds of the invention are compounds of formula I where $R^1$ is hydrogen, methyl, methyl substituted by —$P(O)(OCH_2CH_3)_2$, phenyl, a group of formula III where $R^{28}$ is hydrogen or methyl and $R^{29}$ and $R^{30}$ are each ethyl, or a group of formula IIIA where $R^{31}$ and $R^{32}$ are each methyl and $R^{33}$ is hydrogen or tert-butylcimethylsilyl, $R^2$ is methyl, hydroxy, methoxy, ethoxy, 2-cyanoethoxy or isobutoxy, or together with $R^5$ denotes an oxy group, $R^3$ is hydrogen, hydroxy, acetoxy, trimethylsilyloxy or p-tolyloxythiocarbonyloxy, $R^4$ is hydrogen, $R^5$ is hydroxy, acetoxy, tert-butyldiphenylsilyloxy, thexyldimethylsilyloxy or together with $R^2$ denotes an oxy group and $R^6$ is hydroxy, acetoxy, thyminyl, N-benzyloxymethylthyminyl, uracilyl, 5-methylcytosinyl, adeninyl, N-benzoyladeninyl, or N-(N-methyl-2-pyrroiidinylidene)-5-methylcytosinyl or $R^5$ and $R^6$ together denote isopropylidenedioxy; and $R^7$ is hydrogen, benzoyl, acetyl, benzyl, triphenylmethyl, dimethoxytriphenylmethyl or tert-butyldiphenylsilyl; and compounds of formula I where $R^1$ is a group of formula II where $R^8$ is hydrogen or together with $R^{10}$ denotes a valence bond, $R^9$ is hydrogen. $R^{10}$ is hydrogen or together with $R^8$ denotes a valence bond, $R^{11}$ is hydrogen. $R^{12}$ is hydrogen, methyl, benzyl, benzoyl, naphthoyl or acetyl, $R^{13}$ is hydrogen, hydroxy or acetoxy and $R^{14}$ is hydroxy or acetoxy or $R^{13}$ and $R^{14}$ together denote isopropylidcnedioxy, $R^2$ is hydroxy, ethoxy or isobutoxy, $R^3$ and $R^4$ are hydrogen, $R^5$ is hydroxy or acetoxy and $R^6$ is hydroxy or acetoxy, or $R^5$ and $R^6$ together denote isopropylidenedioxy, and $R^7$ is hydrogen, benzoyl, acetyl, benzyl, triphenylmethyl, dimethoxytriphenylmethyl or tert-butyl diphenylsilyl.

Compounds of the invention may be in the form of one of the possible isomers, for example as a diastereomer, an optical isomer or a racemate, or a mixture thereof.

Preferred isomers of compounds of formula I are those of formula

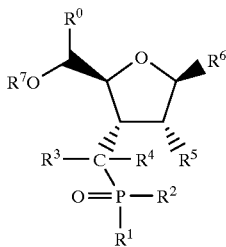

V where $R^0$, $R^2$, $R^3$, $R^4$ and $R^7$ are as hereinbefore defined, $R^1$ is hydrogen, $R^1_a$ or a group of formula

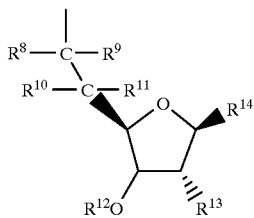

VI where $R^8$ to $R^{12}$ are as hereinbefore defined, $R^5$ is hydrogen, halogen, hydroxy, $R^{18}$, —$OR^{18}$, —$OCOR^{18}$, —$OSO_2R^{18}$, tri ($C_1$–$C_{15}$ hydrocarbyl)silyloxy or Z as hereinbefore defined, or together with $R^2$ denotes an oxy group, $R^6$ is halogen, hydroxy, —$OR^{19}$, —$OCOR^{19}$, —$OSO_2R^{19}$ or $B^1$ as hereinbefore defined, $R^{13}$ is hydrogen, halogen, hydroxy, $R^{26}$, —$OR^{26}$, —$OCOR^{26}$, —$OSO_2R^{26}$, tri($C_1$–$C_{15}$ hydrocarbyl)silyl or Z as hereinbefore defined and $R^{14}$ is halogen, hydroxy, —$OR^{27}$, —$OCOR^{27}$, —$OSO_2R^{27}$ or $B^2$ as hereinbefore defined, and those of formula

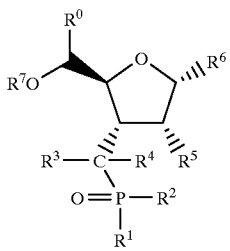

VII where $R^0$, $R^2$, $R^3$, $R^4$ and $R^7$ are as hereinbefore defined, $R^1$ is hydrogen, $R^1_a$ or a group of formula

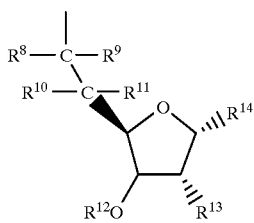

VIII where $R^8$ to $R^{12}$ are as hereinbefore defined, $R^5$ is hydrogen, halogen, hydroxy, $R^{18}$, —$OR^{18}$, —$OCOR^{18}$ or —$OSO_2R^{18}$ as hereinbefore defined or together with $R^2$ denotes an oxy group, or together with $R^6$ denotes a $C_1$–$C_{15}$ hydrocarbylidenedioxy group, $R^6$ is halogen, hydroxy, —$OR^{19}$, —$OCOR^{19}$ or —$OSO_2R^{19}$ as hereinbefore defined, or together with $R^5$ denotes a $C_1$ to $C_{15}$ hydrocarbylidenedioxy group, $R^{13}$ is hydrogen, halogen, hydroxy, $R^{26}$, —$OR^{26}$, —$OCOR^{26}$ or —$OSO_2R^{26}$ as hereinbefore defined or together with $R^{14}$ denotes a $C_1$ to $C_{15}$ hydrocarbylidenedioxy group and $R^{14}$ is halogen, hydroxy, —$OR^{27}$, —$OCOR^{27}$ or —$OSO_2R^{27}$ as hereinbefore defined or together with $R^{13}$ denotes a $C_1$ to $C_{15}$ hydrocarbylidenedioxy group.

Specific especially preferred compounds are those hereinafter described in the Examples.

Compounds of formula I where $R^1$ is $R^1_a$ may be prepared by reacting a compound of formula

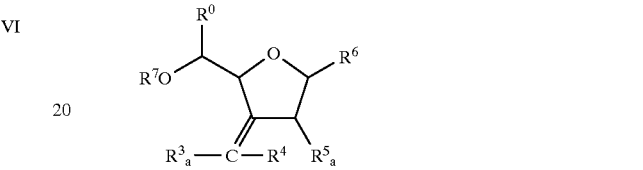

XI where $R^0$ and $R^3_a$ to $R^7$ are as hereinbefore defined, with a compound of formula

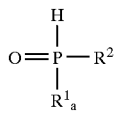

XII where $R^1_a$ and $R^2$ are as hereinbefore defined, in the presence of a free radical initiator. Suitable initiators include azo compounds such as azobis (isobutyronitrile), peroxides such as benzoyl peroxide, tert-butyl peroxide or 2,2-bis(tert-butylperoxy)propane, peresters such as tert-butyl perbenzoate or tert-butyl per-2-ethylhexanoate, percarbonates such as diacetyl perdicarbonate, bis(cyclohexyl)perdicarbonate, or bis (4-tert-butylcyclohexyl)perdicarbonate or persalts such as potassium persulphate. The initiator is generally used in an amount of 0.1 to 100% mol, preferably 5 to 15, mol %, per mol of the compound of formula XI. In general, 1 to 5 equivalents, preferably 1 to 2 equivalents, of the compound of formula XII are used per equivalent of the compound of formula XI. The reaction may be carried out without a solvent, but is preferably carried out in an organic solvent, usually an aromatic hydrocarbon such as benzene, toluene or xylene. It may be carried out at temperatures of 30 to 150° C. preferably 70 to 100° C.

Compounds of formula XI where $R^3_a$ and $R^4$ are each hydrogen and $R^5_a$ and $R^6$ together denote a $C_1$ to $C_{15}$ hydrocarbylidenedioxy group can be obtained by a Wittig reaction of a ketone of formula

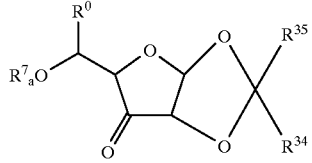

XIII where $R^0$, $R^7_a$, $R^{34}$ and $R^{35}$ are as hereinbefore defined, with a methyltriphenylphosphonium salt and an alkyllithiunm, usually at a temperature increasing from within the range −60 to −80° C. to ambient temperature, the resulting reaction mixture being acidified, usually with acetic acid. The reaction may be carried out in an organic solvent, for example tetrahydrofuran, a hydrocarbon such as hexane or a mixture thereof.

Compounds of formula XI where $R^3_a$ and $R^4$ are each halogen and $R^5_a$ and $R^6$ together denote a $C_1$ to $C_{15}$ hydrocarbylidenedioxy group can be obtained by analogous reactions of compounds of formula XIII. Reaction of such compounds with carbon tetrachloride and triphenylphosphine in acetonitrile using the procedure described by J. M. J. Tronchet et al, Eur. J. Med. Chem-Chim. Ther. 11 (6), 489 (1976), gives compounds of formula XI where $R^3_a$ and $R^4$ are each chlorine. Reaction of compounds of formula XIII with dibromodifluromethane, hexamethylphosphorus triamide and zinc in tetrahydrofuran gives compounds of formula XI where $R^3_a$ and $R^4$ are each fluorine.

Compounds of formula XIII where $R^0$ is hydrogen may be prepared from $C_1$–$C_{15}$ hydrocarbylidenexyloses such as 1,2-isopropylidenexylose by reaction of the primary alcohol group with a compound of formula $R^7_a$ X or $(R^{20}CO)_2O$ where $R^7_a$ and $R^{20}$ are as hereinbefore defined and X is a halogen atom or a hydroxyl group, to convert the methylol group into a group —$CH_2OR^7_a$ or —$CH_2OCOR^{20}$, and reacting the product with an oxidising agent such as pyridinium dichromate, usually at 30–40° C. in the presence of a dehydrating agent such as acetic anhydride and in an inert solvent such as methylene chloride to convert the 3'-hydroxyl group into a keto group. A suitable procedure is described by H. S. Mosher et al, J. Org. Chem 51,2702 (1986). Compounds of formula XIII where $R^0$ and $R^7_aO$ together denote a $C_1$ to $C_{15}$ hydrocarbylidenedioxy group may be prepared by reaction of glucose with a ketone of formula $R^{34}$ CO $R^{35}$ and oxidising the 3' hydroxy group of the di(hydrocarbylidenedioxy) reaction product as hereinbefore described.

The compounds of formula XI where $R^5_a$ and $R^6$ together denote a $C_1$ to $C_{15}$ hydrocarbylidenedioxy group, prepared as described above, are of formula

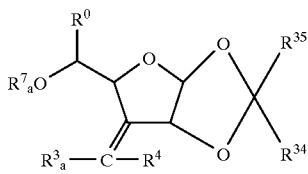

XIV where $R^0$, $R^3_a$, $R^4$, $R^7_a$, $R^{34}$ and $R^{35}$ are as hereinbefore defined These compounds can be subjected to acid hydrolysis, for example by treatment with an acidic ion exchange resin, to hydrolyse the hydrocarbylidenedioxy group(s), usually at 40–100° C., to give corresponding compounds of formula XI where $R^5_a$ and $R^6$ are each hydroxy and $R^0$ is hydrogen, which can in turn be esterified by reaction with an acid of formula $R^{18}COOH$ or an anhydride or acid halide thereof, to give compounds of formula XI where $R^5_a$ is —$OCOR^{18}$ and $R^6$ is —$OCOR^{19}$, $R^{18}$ and $R^{19}$ being the same. The esterification can be carried out using conventional procedures, for example using anhydride or acid halide in the presence of an organic base such as pyridine, dimethylaminopyridine or triethylamine, optionally in an organic solvent such as methylene chloride, an aromatic hydrocarbon such as toluene, an ether such as tetrahydrofuran or an ester such as ethyl acetate. The esterification can be effected at a temperature from −70° C. to 80° C.

Compounds of formula XI where $R^5_a$ is —$OCOR^{18}$ and $R^6$ is $B^1$ as hereinbefore defined can be prepared by glycosylation of compounds of formula XI where $R^5_a$ is —$OCOR^{18}$ and $R^6$ is —$OCOR^{19}$ with a base of formula $B^1H$. Glycosylation is generally effected in the presence of a silylating agent such as trimethylsilyl chloride, bis (trimethylsilyl)acetamide or hexamethyldisilazane and a catalyst such as a fluoroalkanesulphonate salt in an organic solvent such as acetonitrile or 1,2-dichloroethane at a temperature of 40–90° C. Where the compound subjected to glycosylation contains a hydroxyl group, the glycosylation product may be reacted with an aqueous acid such as acetic acid to regenerate a hydroxyl group which has been sylated during glycosylation. The base of formula $B^1H$ is a readily available nucleoside base such as adenine, cytosine, guanine, thymine or uracil or a substituted derivative or analogue thereof prepared by known procedures.

Compounds of formula XI where $R^5_a$ is hydroxy and $R^0$ and $R^7$ are hydrogen can be obtained by hydrolysis of a compound of formula XI in which $R^0$ is hydrogen, $R^5_a$ is —$OCOR^{18}$ and $R^7$ is $R^7_a$ using known procedures. Compounds of formula XI where $R^5_a$ is halogen may be prepared by nucleophilic displacement reactions of compounds of formula XI where $R^5_a$ is hydroxy, using known procedures. Compounds of formula XI where $R^5_a$ is —$OR^{18}$ or tri ($C_{a1}$–$C_{15}$ hydrocarbyl)silyloxy can be prepared by etherificaton of compounds of formula XI where $R^5_a$ is hydroxy, using known etherification procedures.

Compounds of formula XII where $R^1_a$ is a protecting group Q of formula III as hereinbefore defined and $R^2$ is —$OR^{15}_a$ where $R^{15}_a$ is as hereinbefore defined are protected phosphinate esters which can be prepared by known methods, for example as described in EP 0 009 348, U.S. Pat. No. 4,933,478 or Aust. J. Chem. 33,212 (1980).

Compounds of formula XII where $R^1_a$ is a protecting group Q of formula IIIA as hereinbefore defined and $R^2$ is —$OR^{15}_a$ where $R^{15}_a$ is as hereinbefore defined are protected phosphinate esters, which can be prepared by esterifying a phosphinic acid of formula

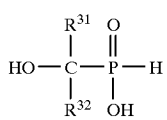

XV with an alcohol of formula $R^{15}_aOH$ where $R^{15}_a$, $R^{31}$ and $R^{32}$ are as hereinbefore defined.

The esterification may be carried out at −20 to 30° C., preferably 0 to 10° C. It is conveniently carried out in a solvent, preferably an ether such as tetrahydrofuran, preferably in the presence of a base, usually a tertary amine such as dimethylaminopyridine, and a dehydrating agent such as N, $N^1$-dicyclohexylcarbodiimide.

Phosphinic acids of formula XV can be prepared by reacting hypophosphorous acid with a ketone of formula

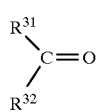

XVI where $R^{31}$ and $R^{32}$ are as hereinbefore defined, or by reacting hypophosphorous acid with a ketal of this ketone using the procedure described by S. J. Fitch, J. Amer. Chem.

Soc. 86, 61(1964). followed by hydrolysis of the resulting phosphonous ester, for example by heating with water.

Compounds of formula XII where $R^1_a$ is $R^1_b$ and $R^2$ is $R^2_a$, where $R^1_b$ and $R^2_a$ are as hereinbefore defined, are phosphine oxides which are either commercially available or may be prepared by conventional methods. Compounds of formula XII where $R^1_a$ is a protecting group Q of formula III as hereinbefore defined and $R^2$ is $R^2_a$ as hereinbefore defined are protected phosphine oxides which can be prepared by reacting a protected phosphinate ester of formula

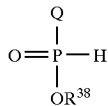

XVII where $R^{38}$ is $C_1$–$C_4$ alkyl and Q is a group of formula III as hereinbefore defined, with an organomagnesium halide of formula $R^2_a$Mg X or an organolithium of formula $R^2_a$Li, where $R^2_a$ and X are as hereinbefore defined.

Compounds of formula XII where $R^1_a$ is alkyl, particularly methyl, substituted by a phosphonic ester group, and $R^2$ is —$OR^{15}_a$ as hereinbefore defined, may be prepared by reacting a phosphinate ester of formula

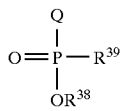

XVIIA where Q is a protecting group Q of formula III as hereinbefore defined, $R^{38}$ is as hereinbefore defined and $R^{39}$ is a $C_1$–$C_4$ alkyl group, preferably methyl, with a strong base such as an alkyllithium an alkali metal hydride or an alkali metal amide to deprotonate the ester of formula XVIIA and reacting the resulting anionic species with a halophosphonic ester such as diethyl chlorophosphate. Both reactions are generally carried out in an organic solvent, usually an ether such as tetrahydrofuran. Deprotonation is usually effected at a temperature from –100° C. to –15° C. and reaction with the halophosphonic ester at –100 to 30° C.

Compounds of formula I where $R^1$ is hydrogen may be prepared by hydrolysis of compounds of formula I where $R^1$ is a protecting group Q to replace Q by a hydrogen atom. This hydrolysis may be carried out using known procedures. For example, where the protecting group Q is of formula III, it may be effected by reaction with a trialkylsilyl halide such as trimethylsilyl chloride, trimethylsilyl bromide or trimethylsilyl iodide. The reaction may be carried out at a temperature of –30° C. to 100° C., preferably 0 to 40° C., preferably under anhydrous conditions, in an organic solvent, for example a halohydrocarbon such as chloroform or trichloroethane, an ether such as tetrahydrofuran or an aromatic hydrocarbon such as benzene, toluene or xylene, or a mixture of two or more of such solvents. When a trialkylsilyl chloride is used, the reaction is carried out in the presence of an alcohol such as ethanol. When $R^2$ in formula I is —$OR^{15}_a$, this group may also be affected by the hydrolysis: in general, use of a trialkylsilyl chloride gives a product in which $R^{15}_a$ is unchanged, while use of a trialkylsilyl iodide gives a product in which $R^{15}_a$ is replaced by hydrogen. When a trialkylsilyl bromide is used, a mixture of a compound in which $R^2$ is —OH and a compound in which $R^2$ is —$OR^{15}_a$ is generally obtained.

Hydrolysis of compounds of formula I where $R^1$ is Q, to replace Q by a hydrogen atom, can also be effected by treatment with an acid, preferably under anhydrous conditions. It may be carried out with a mineral acid such as hydrochloric acid, in which case when $R^2$ is —$OR^{15}_a$ it is also hydrolysed to —OH, or with an organic acid such as acetic acid, in which case when $R^2$ is —$OR^{15}_a$ the product may be a compound in which $R^2$ is —$OR^{15}_a$, a compound in which $R^2$ is —OH or a mixture thereof.

When $R^1$ in formula I is a protecting group Q of formula IIIA, hydrolysis to replace Q by a hydrogen atom can be effected by treatment with a base, for example by treatment with aqueous ammonia or a hindered base such as triethylamine or 1, 8-diazabicyclo[5.4.0]undec-7-ene(DBU), optionally in the presence of alcoholic/aqueous solvent, at a temperature from ambient temperature to 100° C. When $R^2$ in formula I is —$OR^{15}_a$, this group is also affected by the basic hydrolysis; for example, when ammonia, DBU or an alkali metal hydroxide or carbonate is used for the hydrolysis, $R^{15}_a$ is replaced by ammonium or an alkali metal ion respectively which in turn is replaced by hydrogen on acidification of the basic hydrolysis product. The resulting hydroxyl group can be re-esterified, if desired, for example by reaction with an alkyl chloroformate in the presence of a tertary amine or by reaction with an alcohol and a carbodiimide such as dicyclohexylcarbodiimide, optionally in the presence of a base such as 4-dimethylaminopyridine.

Compounds of formula I where $R^1$ is hydrogen may be used in the preparation of dinucleotide analogues and precursors thereof, some of which precursors are novel compounds of formula I where $R^1$ is a group of formula II ($R^{14}$ being other than $B^2$ and $R^2$ being —$OR^{15}$). Accordingly, the present invention also provides the use of compounds of formula I where $R^1$ is hydrogen for the preparation of dinucleotde analogues or precursors thereof by reaction, in the presence of a free radical initiator, with a compound of formula

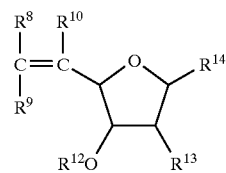

XVIII where $R^8$ to $R^{13}$ are as hereinbefore defined and $R^{14}$ is halogen, hydroxy, —$OR^{27}$, —$OCOR^{27}$, —$OSO_2R^{27}$ or $B^2$, where $R^{27}$ and $B^2$ are as hereinbefore defined, or together with $R^{13}$ denotes a $C_1$ to $C_{15}$ hydrocarbylidenedioxy group. The free radical initiator and the reaction conditions may be as hereinbefore described for the reaction of compounds of formulae XI and XII. When $R^2$ is —$OR^{15}$ in the reactant of formula I where $R^1$ is hydrogen and $R^{14}$ is other than $B^2$ in the compound of formula XVIII when $R^6$ in the reactant of formula I is $B^1$, the product is a compound of the invention where $R^1$ is a group of formula II as hereinbefore defined.

Compounds of formula XVIII where $R^8$ to $R^{10}$ are hydrogen and $R^{13}$ and $R^{14}$ together denote a $C_1$ to $C_{15}$ hydrocarbylidenedioxy group can be prepared by reacting a compound of formula

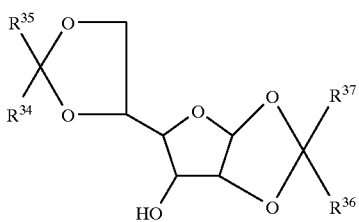

XIX where $R^{34}$ to $R^{37}$ are as hereinbefore defined, with a compound of formula $R^{12}{}_aX$ or $(R^{25}CO)_2O$, where $R^{12}{}_a$, $R^{25}$ and X are as hereinbefore defined, to etherify or esterify the hydroxyl group and reacting the product with 80% acetic acid at ambient temperature to give a compound of formula

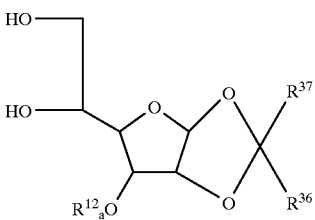

XX where $R^{12}{}_a$, $R^{36}$ and $R^{37}$ are as hereinbefore defined, reacting the compound of formula XX with methanesulphonyl chloride in the presence of a base to replace both of the indicated hydroxyl groups by methanesulphonyloxy groups, and reacting the product with sodium iodide in methyl ethyl ketone at 70–90° C. to give an olefin of formula XVIII where $R^{12}$ is $R^{12}{}_a$, which can be hydrolysed by treatment with potassium carbonate in aqueous methanol at ambient temperature to give an olefine of formula XIII where $R^{12}$ is hydrogen.

Compounds of formula XIX can be prepared using the procedure described (for the preparation of compounds where $R^{34}$ to $R^{37}$ are each methyl) in Carbohyd Res. 24, 194–5 (1972). Compounds of formula I where $R^1$ is a group of formula II in which $R^{13}$ is —OCOR$^{26}$ and $R^{14}$ is —OCOR$^{27}$, where $R^{26}$ and $R^{27}$ are the same, and $R^2$ is —OR$^{15}$, can be prepared by esterification of a compound of formula

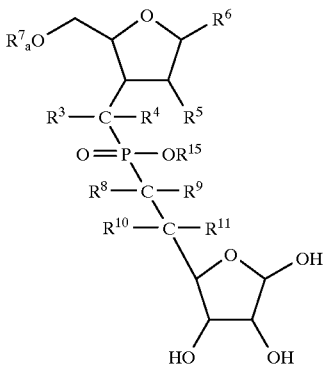

XXI where $R^3$ to $R^6$, $R^7{}_a$, $R^8$ to $R^{11}$ and $R^{15}$ are as hereinbefore defined, with an acid of formula $R^{26}COOH$ or an anhydride or acid halide thereof. This esterification reaction may be carried out using conventional procedures, for example by reaction with an anhydride or acid halide in the presence of an organic base such as pyridine, dimethylaminopyridine or triethylamine, optionally in an organic solvent, for example a halohydrocarbon such as methylene chloride, an aromatic hydrocarbon such as toluene, an ether such as tetrahydrofuran or an ester such as ethyl acetate. The esterification can be effected at a temperature from −70° C. to 80° C. Where, as in preferred embodiments, $R^5$ and $R^6$ in formula XXI are each hydroxy, the product is a compound of formula I in which $R^5$ is —OCOR$^{18}$, $R^6$ is —OCOR$^{19}$, and $R^1$ is a group of formula II in which $R^{13}$ is —OCOR$^{26}$ and $R^{14}$ is —OCOR$^{27}$, $R^{18}$, $R^{19}$, $R^{26}$ and $R^{27}$ being the same. Compounds of formula I where $R^1$ is a group of formula II, $R^2$ is —OR$^{15}$, $R^5$ is —OCOR$^{18}$, $R^6$ is —OCOR$^{19}$, $R^{13}$ is —OCOR$^{26}$ and $R^{14}$ is —OCOR$^{27}$ can be converted into dinucleotide analogues by glycosylation with a base of formula $B^1H$ where $B^1$ is as hereinbefore defined. Glycosylation is generally effected in the presence of silylating agent such as trimethylsilyl chloride, bis(trimethylsilyl) acetamide or hexamethyldisilazane and a catalyst such as a floroalkanesulphonate salt in an organic solvent such as acetonitrile or 1,2-dichloroethane at a temperature of 40–90° C. The base of formula $B^1H$ is a readily available nucleoside base such as adenine, cytosine, guanine, thymine or uracil or a substituted derivative or analogue thereof prepared by known procedures.

Compounds of formula XXI can be prepared by acidic hydrolysis of a compound of formula I where $R^1$ is a group of formula II, $R^2$ is —OR$^{15}$, $R^5$ and $R^6$ together and $R^{13}$ and $R^{14}$ together each denote a $C_1$ to $C_{15}$ hydrocarbylidenedioxy group and $R^7$ is $R^7{}_a$. The acidic hydrolysis can be carried out by reaction with an organic acid such as formic acid, acetic acid, trifluoroacetic acid or p-toluenesulphonic acid together with water and, optionally, an organic solvent such as dioxan or tetrahydrofuran. It may also be carried out with an aqueous inorganic acid such as hydrochloric acid or sulphuric acid. Hydrolysis with organic or inorganic acids may be effected at temperatures from −30° C. to 50° C.; usually it is effected at ambient temperature. The acid hydrolysis can also be carried out by heating with an acidic ion exchange resin and a mixture of water and a polar organic solvent such as dimethyl formamide or dichloromethane or an ether such as diethyl ether, tetrahydrofuran, diethoxymethane or dimethoxyethane, generally at a temperature of 40 to 100° C.

Compounds of formula I where $R^1$ is a group of formula II, $R^2$ is —OR$^{15}$, $R^5$ and $R^6$ together and $R^{13}$ and $R^{14}$ together each denote a $C_1$ to $C_{15}$ hydrocarbylidenedioxy group and $R^7$ is $R^7{}_a$ can be prepared by reacting a compound of formula XIV as hereinbefore defined, in which $R^0$ is hydrogen, with a compound of formula

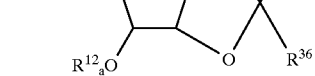

XXII where $R^8$ to $R^{11}$, $R^{15}$, $R^{36}$ and $R^{37}$ are as hereinbefore defined, in the presence of a free radical initiator. Suitable initiators and reaction conditions may be as hereinbefore described for reaction of compounds of formula XI with those of formula XII.

Compounds of formula XXII can be prepared by reaction of an olefine of formula XVIII, where $R^{13}$ and $R^{14}$ together denote a $C_1$–$C_{15}$ hydrocarbylidenedioxy group, with a phosphinate of formula XII, where $R^1_a$ is a protecting group Q of formula III as hereinbefore defined and $R^2$ is —$OR^{15}_a$ as hereinbefore defined, in the presence of a free radical initiator, followed by hydrolysis to replace the protecting group Q by a hydrogen atom as hereinbefore described. The initiator and conditions for reaction of the compounds of formulae XVIII and XII may be as hereinbefore described for reaction of compounds of formula XII with those of formula XI.

Compounds of formula I where $R^0$ and $R^7$ are hydrogen can be prepared by hydrolysis of compounds of formula I where $R^0$ is hydrogen and $R^7$ is $R^7_a$ using known procedures, for example by reaction with a carboxylic acid such as acetic acid in the presence of a quaternary ammonium salt.

Compounds of formula I where $R^0$ is hydrogen, $R^1$ is $R^1_a$, $R^3$ is hydroxy and $R^4$ is hydrogen may also be prepared by reacting an aldehyde of formula

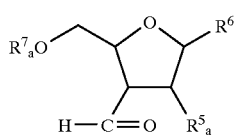

XXIII where $R^5_a$, $R^6$ and $R^7_a$ are as hereinbefore defined, with a compound of formula XII as hereinbefore defined, under basic, neutral or acidic conditions. When the reaction is carried out under basic conditions, the base is preferably a non-nucleophilic base, for example a hindered amine such as 1,8-diazabicyclo[5.4.0]undec-7-ene (DBU) or 1.5-diazabicyclo[4.3.0]non-5-ene or an alkali metal alkoxide such as the tert-butoxide of sodium or potassium. The reaction may be carried out at temperatures of –20 to 100° C., preferably 10 to 30° C. It is preferably effected in an organic solvent, for example a hydrocarbon such as benzene, toluene or xylene, a halohydrocarbon such as dichloroethane or methylene chloride or, preferably, an ether such as diethyl ether, dioxan or, especially, tetrahydrofuran.

When the reaction is performed under neutral conditions, compounds of formula I where $R^0$ is hydrogen, $R^1$ is $R^1_a$, $R^3$ is hydroxy and $R^4$ is hydrogen may be prepared by reaction of a compound of formula XII with a silylating agent to give a P(III) silyl compound and reacting the latter with an aldehyde of formula XXIII as hereinbefore defined. The silylating agent may be, for example, a dialkylhalosilane such as dimethylchlorosilane, trialkylhalosilane such as trimethylchlorosilane or triethylchlorosilane which is reacted with the compound of Formula XII in the presence of tertiary base such as pyridine or triethylamine. Another type of silylating agent which can be used is a bis(trialkylsilyl) derivative of an amide, for example bis(trimethylsilyl)acetamide or bis(trimethylsilyl)trifluoroacetamide). The reaction between the compound of formula XII and the silane or the silyl amide may be carried out at temperatures ranging from –20° C. to 150° C. and can be effected with or without the use of a solvent such as diethylether, tetrahydrofuran, dioxan, dichloromethane or toluene. Alternatively, an excess of the silane can be used as diluent. The silylating agent may alternatively be hexamethyldisilazide, which may be reacted with the compound of Formula XII in the absence of a solvent at 100–200° C. The reaction of the P(III) silyl compound with the aldehyde of formula XXIII may be carried out under conditions conventional for substitution reactions on P(III) species. It is preferably carried out by the Arbuzov method, e.g. at temperatures between ambient and elevated temperatures such as 160° C., followed by hydrolysis of the intermediate silyl species.

When the reaction between the aldehyde of formula XXIII and the compound of formula XII is carried out under acid conditions, it may be carried out in the presence of a Lewis acid such as boron trifluoride or a titanium (IV) compound, for example a titanium tetrahalide such as $TiCl_4$, a titanium dialkoxidedihalide such as $Ti(OiPr)_2Cl_2$ or, preferably, a titanium tetraalkoxide such as titanium tetraisopropoxide.

Aldehydes of formula XXIII may be prepared by reaction of the corresponding $3^1$-iodo compound with carbon monoxide and tris(trimethylsilyl)silane in the presence of a free radical initiator such as 2,$2^1$-azobis(isobutyronitrile), by reduction of the corresponding $3^1$-cyano compound with diisobutylaluminium hydride or otherwise as described in WO 92/20823. Aldehydes of formula XXIII may also be prepared by treatment of the corresponding $3^1$-amino compound with nitrite as described by S. Shuto et al, Nucleosides & Nucleotides, 1 (3), 263–272(1982), or by hydrolysis of the corresponding $3^1$-C-(4,5-dihydro-5-methyl-1,3,5-dithiazin-2-yl) compound as described by Bamford et al, J. Med. Chem. 1990, 33, 2494.

Compounds of formula I in which $R^3$ and $R^4$ are hydrogen can be prepared from corresponding compounds in which $R^3$ is hydroxy and $R^4$ is hydrogen by conventional deoxygenation methods, for example by reaction with a suitably substituted reagent to allow free radical mediated cleavage, such as by reaction with a substituted or unsubstituted $C_6$–$C_{10}$ aryloxythiocarbonyl chloride such as p-tolylchlorothionoformate or pentafluorophenylchlorothionoformate to convert the hydroxy group $R^3$ into a substituted or unsubstituted $C_6$–$C_{10}$ aryloxythiocarbonyloxy group, and then removing this group by reaction with a trialkylstannane such as tri-n-butylstannane or a tris(trialkylsilyl)silane, such as tri(trimethylsilyl)silane, in the presence of a free radical initiator such as azobis(isobutyronitrile) or the free radical initiators hereinbefore described Such deoxygenation can be carried out using conventional procedures. Other standard methods for the deoxygenation of alcohols are described by Hartwig, Tetrahedron 39, 2609 (1983). Similarly, compounds of formula I where $R^5$ and/or $R^{13}$ are hydroxy may be converted, by reaction with an aryloxythiocarbonyl chloride as described above, into compounds of formula I where $R^5$ and/or $R^{13}$ are aryloxythiocarbonyloxy, which can then be reacted with a trialkylstannane in the presence of a free radical initiator to give compounds of formula I where $R^5$ and/or $R^{13}$ are hydrogen.

Compounds of formula I where $R^3$ is halogen and $R^4$ is hydrogen can be prepared from those in which $R^3$ is hydroxy and $R^4$ is hydrogen by nucleophilic displacement reactions using conventional procedures.

Compounds of formula I where $R^0$, $R^3$ and $R^4$ are hydrogen and $R^1$ is $R^1_a$ may also be prepared by reaction of a compound of formula

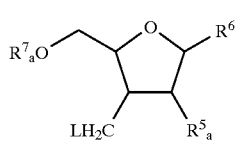

XXIV where $R^5_a$, $R^6$ and $R^7_a$ are as hereinbefore defined and L is a leaving atom or group, with a compound of formula XII as hereinbefore defined.

The leaving atom or group L in formula XXIV may be, for example, a halogen atom or a residue of an organic or inorganic acid after removal of an acidic hydrogen atom therefrom, such as an organic sulphonate group, e.g. a methanesulphonate, trifluoromethanesulphonate or p-toluenesulphonate, or a sulphate anion. Preferably L is a chlorine, bromine or iodine atom or an organic sulphonate group, especially an iodine atom.

The reaction between the compound of formula XXIV and the compound of formula XII may be carried out under conventional conditions for substitution reactions at a P—H bond, for example in the presence of a base such as a tertiary amine, an alkali metal (usually sodium), an organometal of an alkali metal or magnesium (usually an alkyllithium), an alkali metal hydride (usually sodium hydride), or an alkali metal amide such as lithium diisopropylamide or, especially, potassium bis(trimethylsilyl)amide. The reaction may be carried out in an organic solvent, usually an ether such as diethyl ether or tetrahydrofuran, a hydrocarbon such as hexane or toluene, and at a temperature from −100° C. to 100° C., usually from −80° C. to 40° C.

Compounds of formula XXIV may be prepared by reducing an aldehyde of formula XXIII, for example using sodium borohydride, to the corresponding alcohol, and carrying out esterification and/or nucleophilic displacement reactions on the alcohol, for example esterifying the alcohol by reaction with an organic sulphonyl chloride optionally followed by reaction with an alkali metal halide to introduce a halogen atom, or reacting the alcohol with a halogenating reagent, in particular a phosphonium halide such as methyl(triphenoxy) phosphonium iodide to replace the alcoholic hydroxyl directly by halogen. These reactions may be carried out using conventional conditions and procedures.

Compounds of formula I where $R^1$ is a group of formula II in which $R^8$ and $R^{10}$ together denote a valence bond can be prepared by reacting a compound of formula I where $R^0$ is hydrogen, $R^1$ is an alkyl group substituted by a phosphonic ester group, $R^2$ is —$OR^{15}$, $R^5$ and $R^6$ together and $R^{13}$ and $R^{14}$ together each denote a $C_1$ to $C_{15}$ hydrocarbylidenedioxy group and $R^7$ is $R^7_a$, with an aldehyde of formula

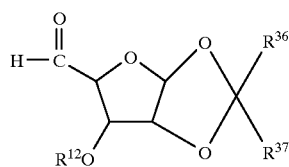

XXV where $R^{12}$, $R^{36}$ and $R^{37}$ are as hereinbefore defined. in the presence of a strong base such as an alkyllithium, an alkali metal hydride, or an alkali metal amide as hereinbefore described, or a mixture of triethylamine and lithium bromide or magensium bromide. The reaction is generally carried out in an organic solvent, usually an ether such as tetrahydrofuran and at a temperature from −100° C. to 0° C., or, where a mixture of triethylamine and a bromide is used, at temperatures up to 30° C.—See M. Prashad, Tetrahedron Letters, 34,1585–88 (1993).

Aldehydes of formula XXV are available commercially or may be prepared by known methods.

Compounds of the invention containing salt-forming groups may be in the form of pharmaceutically acceptable, i.e. physiologically tolerable, salts. For example, a compound of formula I in which $R^2$ is hydroxy, which is a phosphinic acid, may in the form of a pharmaceutically acceptable salt with a base. Such salts include alkali metal salts such as sodium or potassium salts, alkaline earth metal salts such as magnesium or calcium salts, or ammonium salts with ammonia or organic amines, preferably tertiary monoamines and heterocyclic bases such as triethylamine, tri(2-hydroxyethyl)amine, N-ethylpiperidine or N, $N^1$-dimethylpiperazine.

Compounds of formula I in which $R^6$ or $R^{14}$ is a basic group may be in the form of acid addition salts with organic or inorganic acids. Acids which form suitable salts include hydrohalic acids, for example hydrochloric and hydrobromic acid, sulphuric acid, phosphoric acid, nitric acid or perchloric acid, or aliphatic, alicyclic, aromatic or heterocyclic carboxylic or sulphonic acids, such as formic, acetic, propionic, succinic, glycolic, lactic, malic, tartaric, citric, fumaric, maleic, hydroxymaleic, oxalic, pyruvic, phenylacetic, benzoic, p-aminobenzoic, anthranilic, p-hydroxybenzoic, salicyclic, p-aminosalicyclic acid, embonic acid, methanesulphonic, ethanesulphonic, hydroxyethyanesulphonic, ethylenedisulphonic, halobenzenesulphonic, toluenesulphonic, naphthalenesulphonic and sulphanilic acids, methionine, tryptophan, lysine, arginine and ascorbic acid.

Salts of the invention may be prepared by conventional salt-forming procedures.

When mixtures of diastereomers of compounds of formula I or intermediates are obtained, these can be separated by known methods, for example by fractional distillation, crystallisation or chromatography.

The invention also relates to the use of compounds of formula I, and their pharmaceutically acceptable salts, as pharmaceuticals, particularly as anti-viral agents. Accordingly, the present invention also provides a pharmaceutical composition comprising as active ingredient a compound of formula I or a pharmaceutically acceptable salt thereof. The composition may contain a pharmaceutically acceptable carrier such as one conventionally used in pharmaceutical compositions. The compositions may be formulated for enteral or parenteral administration.

The invention is illustrated by the following Examples. Compounds used in the Examples are prepared as follows:

Compound A

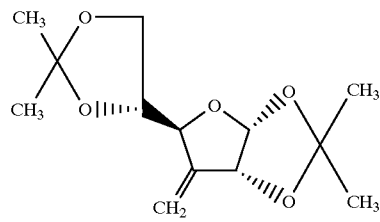

n-Butyllithium (1.6M in hexanes, 6.9 ml, 11.1 mmol) is added to a suspension of methyltriphenylphosphium bromide (3.6 g, 10.0 mmol) in tetrahydrofuran (THF) (25 ml) at −70° C. The mixture is allowed to warm to 20° C. and then cooled to −10° C., whereupon a solution of a ketone of formula XIII where $R^0$ and $R^7_aO$ together, and $R^{34}$ and $R^{35}$ together, denote isopropylidenedioxy groups (1.3 g, 5.0 mmol) in THF (5 ml) and DMPU (5 ml) is added. The suspension is allowed to warm to 20° C. After 18 hours, saturated aqueous ammonium chloride is added. The aqueous layer is separated and then extracted with chloroform. The combined organic phases are dried over magnesium sulphate and evaporated. The resulting material is dissolved in ethyl acetate and washed with water, before drying as above, and evaporation. The resulting material is triturated with ether and subject to chromatography on silica gel, elating with a hexane/ether gradient The product, Compound A is obtained as an oil.

$^1$H NMR (400 MHz, CDCl$_3$) δ 5.44 (d, 1H) 5.50 (d.d, 1H) ppm.

Compound B

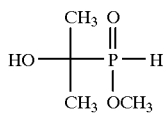

Commercial hypophosphorous acid (50%) is concentrated to 94% on a rotary evaporator. A mixture of hypophosphorous acid (94%, 210.6 g, 3M) and 2,2-dimethoxypropane (917 g, 8.8M) is allowed to stand at room temperature for 6 days. The mixture is evaporated under vacuum and distilled on a wiped-wall still to give Compound B, methyl(1-hydroxy-1-methylethyl)phosphinate (268 g, 65%, b.p. 65° C./0.1 mm).

$^{31}$P nmr (CDCl$_3$, 24.15 MHZ) δ =45 ppm, J$_{PH}$545 Hz. (Fitch.J.Amer.Chem.Soc. 1964, 86, 61).

Compound C

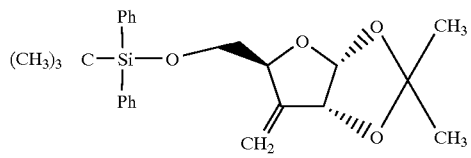

where Ph is phenyl n-Butyllithium (1.6M in hexanes, 12.0 ml, 19.2 mmol) is added to a suspension of methyltriphenylphosphonium bromide (6.35 g, 17.8 mmol) in THF (67 ml) at −65° C. The mixture is warmed to 20° C. and recooled to −65° C., whereupon a solution of a ketone of formula XIII where R$^0$ and R$^7_a$ together, and R$^{34}$ and R$^{35}$ together, denote isopropylidenedioxy groups (5.9 g, 13.8 mmol) in THF (15 ml) is added over 14 minutes. After 2.5 hours, the mixture is allowed to warm to +15° C., then stored at −10° C. for 16 hours. Ammonium chloride (saturated aqueous, 0.3 ml) is added to the mixture which is then filtered. The filtrate is re-filtered after the addition of ether (200 ml).

The filtrate is dried over magnesium sulphate, evaporated and purified by chromatography on silica gel, eluting with a hexane/ether gradient, to give the product as an oil.

$^1$H nmr (CDCl$_3$, 60 MHz) 7.40–7.95 (m,10H), 5.91 (d,1H), 5.45 (m,1H), 5.21 (m,1H), 4.90–5.20 (m,2H), 3.70–3.80 (m,2H), 1.52 (s,3H), 1.40 (s,3H), 1.06 (s, 9H) ppm.

Compound D

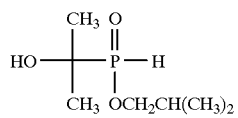

Compound B is heated with water (11) on a steam bath for 8 hours until conversion to 1-hydroxy-1-methylethylphosphonous acid is complete (monitored by $^{31}$P nmr). The water is removed on a rotary evaporator and the residue is completely dried by co-evaporation with toluene. A sample of this phosphonous acid (4.6 g, 0.037M), isobutyl alcohol (3.02 g, 0.041M) and dimethylaminopyridine (0.5 g, 0.0041M) is stirred at 5° C. in tetrahydrofuran. Dicyclohexylcarbodiimide (8.4 g, 0.041M) is added portionwise over 30 minutes. On completion of the reaction ($^{31}$P nmr), ether (50 ml) is added and the precipitated diccylohexyl urea is filtered off. Evaporation of the ether liquors gives a pale yellow oil (6.7 g) which is purified by chromatography on silica using ether, then ethyl acetate, as eluant to give Compound D, isobutyl (1-hydroxy-1-methylethyl) phosphinate.

Found: C 47.0, H 9.5, P 17.1%; C$_7$H$_{17}$O$_3$P requires C 46.7, H 9.5, P 17.2%.

$^{31}$P nmr (CDCl$_3$, 162 MHZ) δ =42.2 ppm.

Compound E

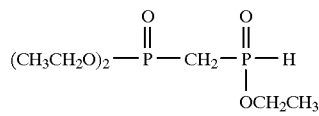

To a solution of diisopropylamine (15.7 ml, 0.112 mol) in tetrahydrofuran (200 ml) at −20° C., n-butyllithium (1.6M in hexanes, 75.4 ml) is added dropwise. The solution is allowed to warm to 0° C. and cooled to −74° C. after 15 minutes. Ethyl (1,1-diethoxyethyl) methyiphosphinate prepared as described in EP 0 009 348 (25.0 g, 0.112 mmol) is added dropwise by syringe over 5 minutes, maintaining the temperature at below −57° C. After 1 hour at −70° C., diethyl chlorophosphate (17.3 ml, 0.119 mol) is added dropwise and, after a further hour, lithium diisopropylamide (0.112 mol) (prepared by the addition of n butyllithium to diisopropylamine as above) in THF (75 ml) is added over 20 minutes at −65° C. The reaction mixture is stirred for a further hour at −70° C., then warmed to 20° C., and stood for 18 hours. Saturated aqueous ammonium chloride (20 ml) is added, and the reaction mixture is concentrated at below 35° C. Dichloromethane is added to the residue, which is then washed with water three times. The water layer is backwashed with ether. The combined organic phases are dried with a brine wash, then over magnesium sulphate, and evaporated to a brown oil.

The crude product is purified by short path distillation to give an intermediate product as clear viscous oil.

b.p. 165–175° C. (0.005 mmHg)

$^{31}$P nmr (CDCl$_3$, 161 MHZ): 39.35 (d, Jpp 15.6 Hz), 21.30 (d)

mass spectrum C.I. (NH$_3$) 378 (MNH$_4^+$), 117 (100)

The intermediate product is of formula

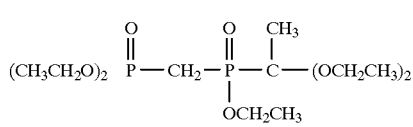

To a solution of the intermediate product (4.5 g, 12.5 mmol) in chloroform (10 ml), chlorotrimethylsilane (5 ml) is added dropwise over 5 minutes. The solution is sirred for 4 hours then ethanol (2 ml) is added. After a further 1.5 hours, the solvent is evaporated and the residue distilled by short path distillation (160° C./0.02 mmHg) Compound E is obtained as a clear oil.

$^{31}$P nmr (CDCl$_3$, 161 MHZ) 26.47 (d, Jpp, 5.4 Hz) 18.95 (d, Jpp, 5.9 Hz) ppm J$_{PH}$ 579 Hz mass spectrum C.I.(NH$_3$) 262 (MNH$_4^+$)

Compound F

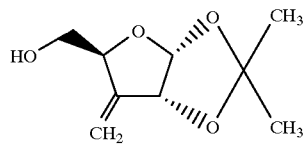

To a solution of Compound C (1.50 g, 3.53 mmol) in THF (10 ml) at 20° C., tetrabutylammonium fluoride (1.0M in THF, 3.89 ml) is added. When the reaction is complete. the solvent is evaporated and the residue purified by chromatography on silica gel, eluting with a hexane/ether gradient. The product is distilled (short path) (125–130° C., 0.02 mmHg) to give further purified material.

$^1$H nmr (CDCl$_3$, 400 MHz) 5.86 (d, 1H, J=3.7 Hz); 5.47 (s, 1H); 5.18 (s, 1H); 4.90 (d 1H, J=2.5 Hz); 4.81 (m,1H); 3.87 (d,1H, J=12 Hz); 3.67 (dd, J=4.4, 11.9 Hz, 1H); 1.26 (s, 3H); 1.19 (s, 3H) ppm.

Compound G

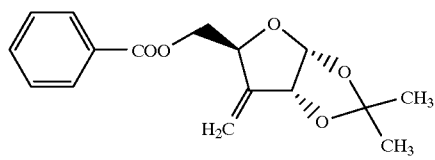

To a suspension of methyltriphenylphosphonium bromide (82.5 g, 0.231 mol) in dry tetrahydrofuran (500 ml) at −70° C. under argon is added n-butyl lithium (1.6 m in hexane, 144 ml, 0.231 mol) over about 10 minutes. The mixture is allowed to warm to 15° C. during which time an orange solution forms. This mixture is re-cooled to −70° C., more n-butyl lithium (6 ml) is added, and after a further 15 minutes, a solution of 5-O-benzoyl-1,2-di-O-acetonide-3-ketoxylose prepared as described by H. S. Mosher. J. Org. Chem. 1986, 51, 2702 (50.0 g, 0.17 mol) in dry tetrahydrofuran (100 ml) is added in 5 batches over 35 minutes, whilst maintaining the reaction temperature at −66 to −70° C. The mixture is kept at −70° C. for 2 hours, then allowed to warm to +10° C. over 1.5 hours and maintained at this temperature for 3 hours. Acetic acid (3.5 ml) is added, followed by hexane (500 ml). The resultant precipitate is separated by filtration and the liquors passed through a pad of silica gel (ca 2 cm deep). This pad is washed with ether (1 litre) and the filtate is evaporated to yield a crude oil. The product is purified by flash column chromatography over silica gel (Merck, Art 15111, 10 cm Ø, 5 cm L) eluting with hexane then hexane: ether (3:1) mixtures to yield Compound G as a colourless solid, mp 61–62° C.

δH (CDCl$_3$) 8.10 (2H, d, Ph-H), 7.55 (1H, t, Ph-H), 7.41 (2H, t, Ph-H), 5.95 (1H, d, H-1), 5.50) (1H, s, C═CH), 5.35 (1H, s, C═CH), 5.10 (1H, m, H=4), 4.96 (1H, d, H-2), 4.55 (1H, dd, H-5), 4.40 (1H, dd, H-5), 1.55 (3H, s, CH$_3$), 1.40 (3H, s, CH$_3$) ppm.

δC (CDCl$_3$) 166.2 (COPh), 145.6, 133.1, 129.6, 128.3, 112.7, 112.6, 104.5, 81.6, 77.3, 65.6, 27.3, 27.0 ppm.

Found: C 66.5, H 6.4%; C$_{16}$H$_{18}$O$_5$ requires C 66.25, H 6.25%.

Compound H

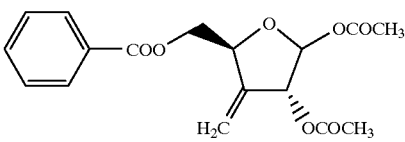

A mixture of Compound G (20.0 g, 68.9 mmol) in water (20 ml) and tetrahydrofuran (150 ml) and DOWEX® 50 W×2 50–100 mesh ion-exchange resin (100 ml) is heated at reflux for 5 days. The mixture is filtered and the resin washed with dichloromethane (100 ml). The filtrates are evaporated and co-evaporated with toluene (3×100 ml) to yield a viscous orange oil. To a solution of this oil in dichloromethane (100 ml) at 0° C. is added pyridine (22 ml, 0.276 mol) and acetic anhydride (19.3 ml. 0.207 mol) and the mixture is stirred at 0° C. for 3 hours. The solvents are evaporated to yield the crude product which is purified by column chromatography over silica gel (Merck, Art 7734, 500 g) eluting with ether hexane (1:10 to 4:10) mixtures. Fractions adjudged pure by thin layer chromatography are collected and evaporated to yield Compound H as a colourless oil, as a mixture 5:2 of α:β anomers at position 1.

Compound I

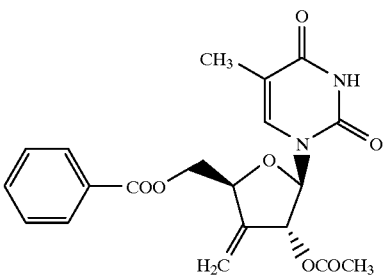

A suspension of thymine (4.38 g, 34.7 mmol) and bis (trmethylsilyl)acetamide (14.12 g, 69.4 mmol) is heated to 70° C. with stirring under argon for 2 hours. The resulting solution is allowed to cool to 22° C. over 2 hours. A solution of Compound H (11.6 g, 34.7 mmol) in 1,2dichloroethane (15 ml) is added to the above reaction mixture with stirring at 22° C. Trimethylsilyl trifluoromethane sulphonate (9.25 g, 41.6 mmol) is then added, dropwise, over 15 minutes. The reaction mixture is heated to 50° C., with stirring, for 3 hours. A solution of saturated aqueous sodium hydrogen carbonate (80 ml) is added slowly to the mixture and, when effervescence ceases, this is transferred to a separating funnel. The products are extracted into chloroform (4×50 ml) and the extracts washed with brine before drying (magnesium sulphate). Evaporation affords the crude product (15.0 g). Purification by flash column chromatography over silica gel (Merck, Art 15111, 4 cm×10 cm L) eluting with hexane, then hexane:ethyl acetate (1:1) mixtures, affords after evaporation of those appropriate fractions ajudged pure by thin layer chromotagraphy, Compound I as a colourless glassy solid mpt. 55–58° C.

$^1$H NMR (CDCl$_3$) δ 8.95 (1H, bs, NH), 8.04 (2H, m, Ph-H). 7.61 (1H, m, Ph-H), 7.48 (2H, m, Ph-H), 7.17 (1H, d, J=1.3H thymine-H), 6.07 (1H, d, J=5.7 Hz, H-1), 5.74 (1H, m, H-2'), 5.49 (1H, m, C═CH), 5.41 (1H, m, C═CH), 5.03 (1H, m, H-4'), 4.71 (1H, dd, J=12.3, 2.8 Hz, H-5'), 4.54(1H, dd, J=12.3, 4.4 Hz, H-5'), 2.15 (3H, s, COCH$_3$), 1.65 (3H, d, J=1.0 Hz CH$_3$) ppm.

$^{13}$C NMR (CDCl$_3$) δ 170.29 (CH$_3$C(O)), 166.04 (Ph C(O)), 163.65 (C-2) 150.62 (C-4), 141.70 (C-3$^1$), 134.56 (C-6), 133.46, 129.43, 129.28,128.60, (Ph), 112.76 (C=CH$_2$), 111.85 (C-5), 86.72 (C-1$^1$), 78.20 (C-2$^1$), 75.32 (C-4$^1$), 65.42 (C-5$^1$), 20.65 ( CH$_3$C(O)), 12.15 (CH$_3$)ppm.

Found: C 59.6, H 5.25, N 6.7%; C$_{20}$H$_{20}$N$_2$O$_7$ requires C 60.0, H 5.03, N 7.00%.

Compound J

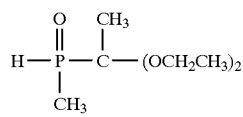

To a solution of methyl(1,1-diethoxyethyl)phosphine oxide, prepared as described in EP 0 501 702 (89.3 g, 0.5 mol) in THF (900 ml) at −78° C. under an atmosphere of argon is added a solution of potassium bis(trimethylsilyl) amide (688 ml, 0.521 mol) in toluene over 15 minutes. After stirring for 1 hour at −78° C., methyl iodide (34 ml, 0.55 mol) is added over 5 minutes and stirring at −78° C. continued for 1 hour. The reaction is then quenched by the addition of a 1% solution of NaH$_2$PO$_4$ (450 ml) and slow warming to room temperature. Concentration gives an aqueous suspension to which dichloromethane (600 ml) is added. The organic phase is separated and washed with 1% NaH$_2$PO$_4$ (500 ml), followed by water (500 ml). Drying over MgSO$_4$, concentration and purification by flash vacuum silica column chromatography (chloroform-ethanol 40:1) gives a clear oil which is distilled to give dimethyl (1,1-diethoxyethyl)phosphine oxide. b.p. 100° C. at 0.05 mmHg.

Found C 49.1, H 10.2, P 16.1%; C$_8$H$_{19}$O$_3$P requires C 49.5, H 9.85, P 15.95%.

$^{31}$Pnmr $^1$H decoupled (CDCl$_3$, 36 MHz) δ 48.3 ppm.

Compound K

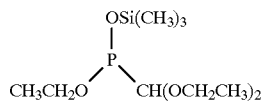

This is prepared as described in R. G. HALL et al. Tetrahedron 1989, 45, p3787.

Compound L

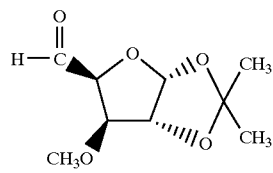

This aldehyde is available commercially.

Compound M

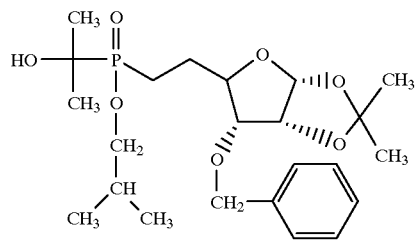

A solution of isobutyl(1-hydroxy-1-methylethyl) phosphinate (12.6 g, 0.07M) and tert-burylcyclohexylperdicarbonate (0.5 g) in toluene (2 ml) is heated at 80° C. under argon. The compound of formula

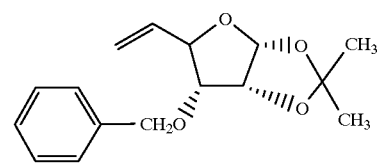

(19.34 g, 0.07M) in toluene (2 ml) is added portionwise over 2 hours. A further 2.5 g perdicarbonate in toluene (6 ml) is added over 2 hours. The reaction mixture is stirred for a further 10 hours, adding perdicarbonate (0.25 g) every 2 hours when the reaction appears complete ($^{31}$P nmr). The mixture is cooled and evaporated to a gum which is purified on silica by flash chromatography using ethyl acetate, then 5% methanol in ethyl acetate, as eluants. The methanolic eluates were re-chromatographed on silica using 5% methanol in ethyl acetate as eluant to give Compound M.

$^{31}$P nmr (CDCl$_3$162 MHz) δ =56.0, 56.2 ppm.

Compound N

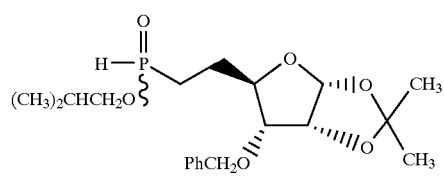

Ph = phenyl

To a solution of aqueous ammonia (20 ml, 20%), Compound M (0.95 g, 2.1 mmol) is added. The mixture is heated at 70° C. for 12 hours, cooled, evaporated and then co-evaporated with toluene. The residue is dissolved in dichloromethane (9 ml). To the resulting solution at −10° C. is added triethylamine (0.32 ml, 2.3 mmol), followed dropwise by isobutyl chloroformate (0.55 ml, 4.2 mmol). After 45 minutes the reaction mixture is allowed to warm to 20° C. After 2 hours, the reaction mixture is evaporated and the residue purified by chromatography on silica gel, eluting with a gradient of methanol/ethyl acetate. The product, a mixture of two diastereoisomers, is obtained as a clear oil.

$^{31}$P nmr (36 MHz, CDCl$_3$) δ 38.8, 39.1 ppm; J$_{PH}$540 Hz.

m/z Cl(NH$_3$)399(MH$^+$), 416(MNH$_4$$^+$), 341(100) (M-iBu).

Compound O

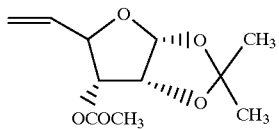

A mixture of the compound of formula

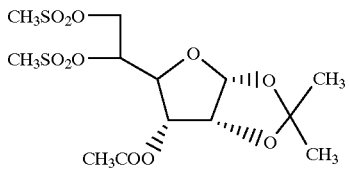

(65 g, 0.155M) and sodium iodide (94 g, 0.62M) in butan-2-one (1.5l) is heated to reflux for 5 hours. A further 10% of sodium iodide is added and heating continued for 3 hours. The solvent is removed and the dark brown residue is partitioned between chloroform and water. Sodium thiosulphate is added portionwise until the solution is colourless. The chloroform extracts are separated, washed with sodium bicarbonate then brine and dried ($MgSO_4$). Evaporation gives a pale yellow oil which is purified by chromatography on silica using hexane: ethyl acetate, 2:1, eluant, to give Compound 16. An analytical sample is obtained by bulb to bulb distillation (100° C./0.1 mm Hg), $[\alpha]_D^{25}$+107.5, c 1.13 $CHCl_3$;

Found C 58.0, H 7.0; $C_{11}H_{16}O_5$ requires C 57.9, H 7.1%.

Compound P

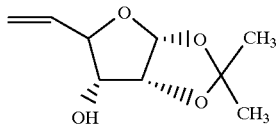

Compound O (15 g 0.066M) dissolved in methanol (100 ml) is added to a solution of potassium carbonate (22.7 g, 0.165M) in water (100 ml). After 15 minutes the reaction is complete (TLC).

The solvent volume is reduced to 50 ml and after further co-evaporation with water the residue is washed with chloroform (3×100 ml). The chloroform extracts are washed with brine then dried ($MgSO_4$). Evaporation gives a white solid, m.pt. 67-5–68° C., $[\alpha]_D^{25}$+38.2° C. 0.95 $CHCl_3$.

Found C 57.8, H 8.0; Calculated for $C_9H_{14}O_4$, C 58.05, H 7.6%.

Compound O

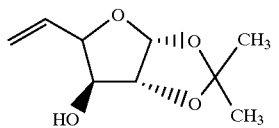

is prepared as described by Hall, Hough and Pritchard, J. Chem.Soc. 1961,1541.

Compound R

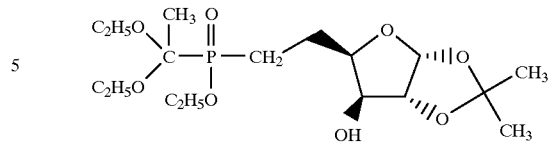

To a solution of ethyl(1,1-diethoxyethyl)phosphinate (1.55 g, 6.9 mmole) in THF (30 ml) at −78° C. under an atmosphere of argon is added n-butyllithium (4.3 ml, 1.6 molar solution in hexanes) slowly over 5 minutes. The resulting solution is stirred at −78° C. for 1 hour. Boron trifluoride etherate (0.85 ml, 6.9 mmole) is then added over 2 minutes followed by the dropwise addition of a solution of an oxetane of formula

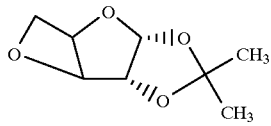

prepared by the method of: J. P. Horwitz et al J. Org. Chem. 28, 942, (1963) (0.40 g, 2.3 mmole) in THF (10 ml). The resulting solution is stirred for 2 hours at −78° C. before the addition of $NaHCO_3$ (saturated, 5 ml). The resulting mixture is allowed to warm to ambient temperature over 1 hour and is then concentrated in vacuo. Addition of dichloromethane and filtration gives a clear oil after concentration. Purification by flash silica column chromatography (chloroform-ethanol 40:1) gives Compound R as a thick oil.

Found: C 50.6%, H 8.4%, P 7.7%; $C_{17}H_{33}O_8P.\frac{1}{2} H_2O$ requires C 50.35%, H 8.45%, P 7.65%.

$^{31}P$ nmr $^1H$ decoupled ($CDCl_3$, 36.4 MHz) δ 51.3, 51.1 ppm.

Compounds S and T

Compound S

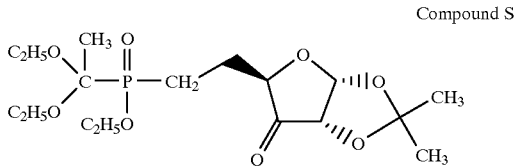

Compound T

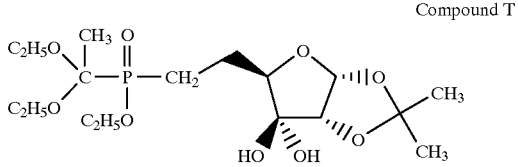

A solution of dimethylsulphoxide (0.56 ml, 7.9 mmol) in dichloromethane (5 ml) is added to a mixture of oxalyl chloride (0.3 ml, 3.4 mmol) in dichloromethane (45 ml) maintained at −70° C. After 10 minutes. a solution of Compound R (1.05 g, 2.64 mmol) in tetrahydrofuran (10 ml) is added dropwise, maintaining the temperature at −70° C. After 15 minutes, triethylamine (2.76 ml, 0.0198 mol) is added dropwise and the mixture is allowed to warm gradually to ambient temperature. The mixture is diluted with ethyl acetate (150 ml) and washed with water (2×50 ml). Evaporation of the organic phase and co-evaporation with more ethyl acetate gives a mixture of Compounds S and T as a colourless oil which is pure enough for use in subsequent reactions. A sample (80 mg) is purified by column chromatography over silica gel (Merck, Art 7734, 3 g) eluting with dichloromethane: ethyl acetate (25:1) mixtures. Pure fractions are evaporated to give a mixture of Compounds S and T as a colourless oil.

ν max (thin film) 3600–3100 (br, OH), 1780, 1740 (CO) cm$^{-1}$ $^{31}$P nmr (CDCl$_3$) δ 52.01, 51.72 and 48.30, 48.01 ppm.

Compound U

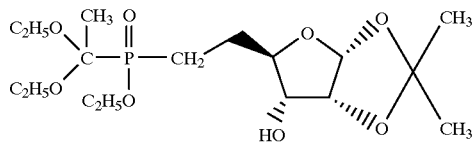

To a solution of the mixture of Compounds S and T (1.02 g, 2.485 mmol) in ethanol (50 ml) at −10° C. is added sodium borohydride (113 mg, 2.98 mmol) in three portions over 15 minutes. The mixture is partitioned between ethyl acetate (200 ml) and water (50 ml). The organic phase is washed with water (2×50 ml), dried (MgSO4), filtered and evaporated to yield Compound U as a colourless oil.

$^{31}$P (CDCl$_3$) δ 49.32 ppm.

$^1$H nmr (CDCl$_3$) δ 5.76(1H, d, H-1), 4.58 (1H, m, H-2$^1$), 4.2 (2H, m, H-3, H-4), 3.7 (6H, m, OCH$_2$×3), 3.05 (1H, br d, OH), 2.15–1.7 (4H, m, PCH$_2$CH$_2$), 1.58 and 1.35 (2×s, 2×OC(CH$_3$)$_2$), 1.44 (3H, d, PCCH$_3$), 1.35 and 1.25 (6H, 2×t, OCH$_2$CH$_3$), 1.20 (6H, t, P COCH$_2$CH$_3$×2)ppm.

Compound V

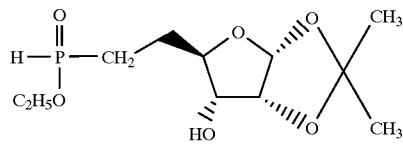

To a solution of Compound U (0.97 g, 2.447 mmol) in chloroform (35 ml) containing 0.6% ethanol at room temperature, under argon is added trimethylsilyl chloride dropwise over 30 minutes. The mixture is stirred at 24° C. for 6 hours, then kept at −20° C. for 18 hours. Evaporation gives crude product (780 mg) as a colourless oil. Purification by column chromatography over silica gel (Merck, Art 7734, 35 g) eluting with 1–8% ethanol: chloroform mixtures. Appropriate fractions are collected and evaporated to give Compound V as a colourless oil.

$^{31}$P nmr (CDCl$_3$) δ 38.90 and 38.64 ppm.

$^1$H nmr (CDCl$_3$) δ 7.80 (0.5H, m, P-H), 6.43 (0.5H, m, P-H), 5.75 (1H, m, H-1), 4.48 (1H, m, H-4), 4.15 (1H, m, PO CH) 4.08 (1H, m, POCH), 3.61 (1H, m, H-3), 2.1–1.8 (4H, m, P CH$_2$CH$_2$), 1.55 (3H, s, CCH$_3$), 1.35 (6H, m, CCH$_3$ and POCH$_2$CH$_3$) ppm.

$^{13}$C nmr (CDCl$_3$) 112.47 (s), 103.54 (s), 79.30 (d), 78.54 (s), 75.29 (s), 62.36 (s), 26.38 (s), 26.28 (s), 24.71 (d), 16.210 (s) ppm.

Compound W

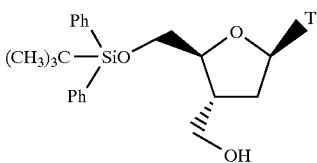

Ph = phenyl
T = 1-thyminyl

To a solution of an aldehyde of formula XXIII where R$^5_a$ is hydrogen, R$^6$ is 1-thyminyl and R$^7$ is tert-butyl diphenylsilyl, prepared as described in WO 92/20823, (11.2 g 23 mmol) in anhydrous ethanol (120 ml) at room temperature is added NaBH$_4$ (865 mg, 23 mmol) portionwise over 5 minutes. After 1 hour, the reaction mixture is quenched with water, diluted with ethylacetate (500 ml) and washed with water (2×50 ml). After back extration of the aqueous phase, the combined organic phase is dried (MgSO$_4$) and concentrated to give Compound W as a white solid.

$^1$H nmr (CDCl$_3$, 400 MHz) δ 9.10 (1H, s, NH) 7.65 (4H, d, Ar 4×CH ortho), 7.40 (7H, M, Ar 4×CH meta, 2×CH para+H6) 6.13 (1H, t, H1') 4.00 (1H, dd, H5'), 3.93 (1H, m, H4') 3.82 (1H, dd, H5'), 3.62 (2H, m, CH$_2$OH) 2.60 (1H, m, H3'), 2.32 (1H, m, H-2'), 2.12 (1H, m, H2') 1.62 (3H, s, T-CH$_3$) and 1.10 (9H, s, $^t$Bu) ppm.

Compound X

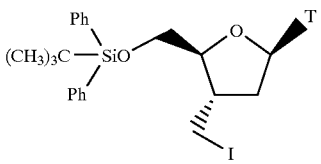

Ph = phenyl
T = 1-thyminyl

To a solution of Compound W (9 g, 18.1 mmol) in dry DMF (100 ml) at 0–5° C. is added 2,6-lutidine (4.25 ml, 36.5 mmol) followed by methyltriphenoxyphosphonium iodide (9.45 g 20.9 mmol). The resulting mixture is allowed to warm to room temperature. After 1 hour the mixture is diluted (200 ml ethyl acetate) and washed with 0.1N NaS$_2$O$_3$ (2×20 ml), 0.5N Hydrochloric acid (2×20 ml) and water (2×20 ml). Drying, concentration and purification by flash silica column chromatography (gradient elution chloroform: ethylacetate 20:1–7:1) gives Compound X as a white solid.

$^1$H nmr (CDCl$_3$, 400 MHz) δ 10.2 (1H, s, NH) 7.66 (4H, d, 4×CH ortho), 7.40 (7H, m, 4×CH meta, 2×CH para+H6) 6.19 (1H, t, H1') 4.02 (1H, dd, H5') 3.82 (1H, m, H 4'), 3.78 (1H, dd, H5'), 3.17 (1H, dd, CH$_2$I), 3.10 (1H, dd, CH$_2$I), 2.68 (1H, m, H3'), 2.30 (1H, m, H2') 2.23 (1H, m, H2') 1.66 (3H, s, CH$_3$-T), 1.10 (9H, s, tBu) ppm.

EXAMPLE 1

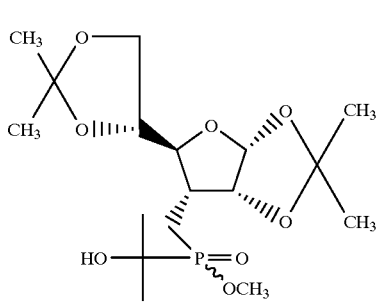
Compound 1

A solution of Compound A (6.39 g, 24.9 mmol) and biscyclohexyl perdicarbonate (BCHPC) (0.99 g, 2.5 mmol) in toluene (2 ml) is added dropwise to stirred Compound B (5.16 g, 37.4 mmol) at 80° C. under an argon atmosphere. After 4 hours, the reaction mixture is cooled, evaporated and purified by chromatography on silica gel, eluting with ethanol/chloroform, to give the product, Compound 1, a solid m.p. 95–100° C., as a mixture of two epimers at phosphorus.

$^{31}$P nmr (CDCl$_3$, 24 MHz) δ 56.5, 56.3 ppm.

Elemental Analysis expected: C 51.77%, H 7.92%, P 7.86% Found: C 51.33%, H 7.79%, P 7.92%.

Recrystallisation of the above product from ether/hexane gives a single diastereomer (d.e. 96%)

$^{31}$P nmr (CDCl$_3$, 24 MHz) δ 59.9 ppm.

EXAMPLE 2

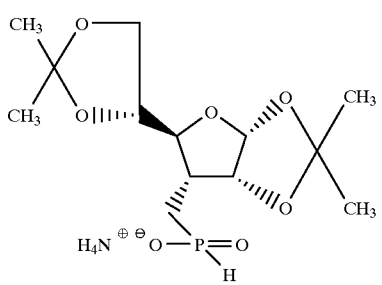
Compound 2

A solution of Compound 1 (0.50 g, 1.3 mmol) in methanol (10 ml) and aqueous ammonia (30%, 5 ml) is heated to 80° C. and additional quantities of aqueous ammonia are added (×1 ml until the reaction is complete (60 hours). The reaction mixture is evaporated, triturated with ether and crystallised to give Compound 2.

$^{31}$P nmr (D$_2$O, 24 MHz) δ 23.3 ppm.

Elemental Analysis: expected C 44.8%, H 7.8%, N 4.0%, P 8.9% C$_{13}$H$_{26}$NO$_7$P.0.5H$_2$O: Found C 44.7%, H 7.9%, N 3.6%, P 9.0

EXAMPLE 3

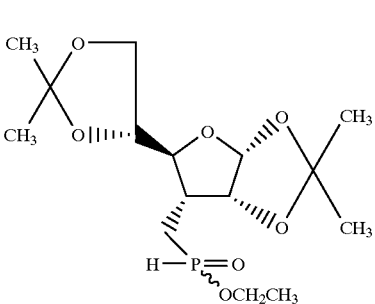
Compound 3

To a solution of Compound 2 (80 mg, 0.25 mmol) in dichloromethane (2 ml) at 0° C., ethyl chloroformate (28μl, 0.30 mmol) and triethylamine (39μl, 0.27 mmol) are added. After 2.5 hours, the reaction mixture is diluted with dichloromethane, washed successively with water and brine and then evaporated. The residue is purified by chromatography (silica gel; eluting with 5% ethanol/chloroform) to give Compound 3 as a mixture of two diastereoisomers.

$^{31}$P nmr (CDCl$_3$, 24 MHz) δ 34.56, 35.17 ppm $^1$H nmr (CDCl$_3$, 400 MHz) δ 6.56 (m, ½H), 7.92 (m, ½H, J$_{PH}$537 Hz) ppm.

EXAMPLE 4

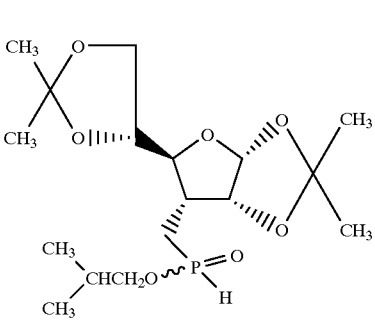
Compound 4

To a solution of Compound 2 (274 mg, 0.81 mmol) in dichloromethane at 0° C., isobutylchloroformate (0.13 ml, 1.0 mmol) and triethylamine (0.13 ml, 0.94 mmol) is added. After 6.5 hours the mixture is evaporated and then purified by silica gel chromatography, eluting with 2% EtOH/CHCl$_3$, to give Compound 4 as a mixture of two diastereoisomers.

$^{31}$P nmr (CDCl$_3$, 24 MHz) δ 36.9, 36.2 ppm, J$_{PH}$ 540 Hz.

$^1$H nmr (CDCl$_3$, 400 MHz) δ 6.53 (m, ½H), 7.90 (m, ½H, P-H) ppm.

EXAMPLE 5

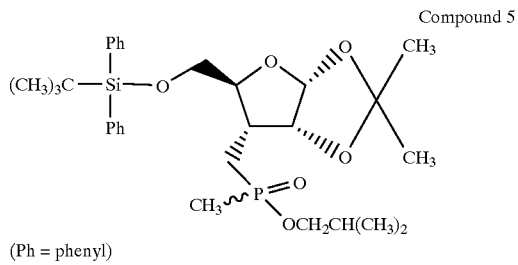

Compound 5

(Ph = phenyl)

To isobutyl methylphosphinate (0.95 g, 6.98 mmol) at 80° C. under argon, is added over 2.5 hours a solution of Compound C (1.00 g, 2.35 mmol) and BCHPC (0.1 g, 0.25 mmol) in toluene (1.5 ml). After a further 1 hour the reaction mixture is cooled and solvent and excess reagents removed by short-path distillation (70–80° C., 0.05 mmHg). The residue is purified by chromatography on silica gel, eluting with hexane/ethyl acetate, 50:50–0:100). The product, Compound 5, a viscous oil is obtained as a mixture of two diastereomers.

$^{31}$P nmr (CDCl$_3$, 24 MHz) δ 52.9, 52.3 ppm.

EXAMPLE 6

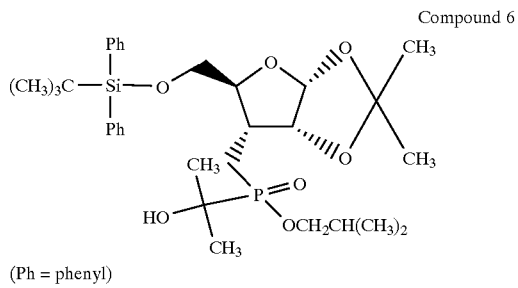

Compound 6

(Ph = phenyl)

A solution of Compound C (11.5 g, 27.1 mmol) and BCHPC (0.5 g, 1.3 mmol) in toluene (15 ml) is added to stirred Compound D (5.9 g, 32.5 mmol) under argon at 75° C. over 50 minutes. After 100 minutes, further BCHPC (0.1 g) is added After 3 hours, the reaction mixture is cooled, diluted with ethyl acetate and washed with water then brine. The organic phase is dried over magnesium sulphate, evaporated, and the residue purified by silica gel chromatography, eluting with a hexane/ethyl acetate gradient and then a methanol/ethyl acetate gradient. Compound 6 is obtained as a mixture of two diastereomers, plus separated isomers.

ISOMER A $^{31}$P nmr (CDCl$_3$, 24 MHz) δ 54.0 ppm $^1$H nmr (CDCl$_3$, 400 MHz) δ 4.84 (t, 1H) ppm

ISOMER B $^{31}$P nmr (CDCl$_3$, 24 MHz) δ 54.1 ppm $^1$H nmr (CDCl$_3$, 400 MHz) δ 4.92 (t, 1H ) ppm Elemental Analysis Expected: C 63.55%, H 8.17%, P 5.12%, Si4.64% C$_{32}$H$_{51}$O$_7$PSi Found: C 63.1%, H 8.1%, P 5.2%, Si5.0% mass spectrum C.I.(NH$_3$) 605 (MH$^+$)

EXAMPLE 7

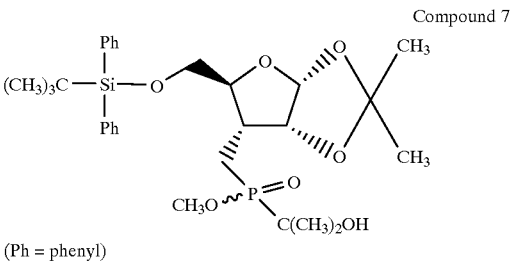

Compound 7

(Ph = phenyl)

A solution of Compound C (0.50 g, 1.18 mmol) and BCHPC (47 mg, 0.12 mmol) in toluene (0.5 ml) is added to stirred Compound B (0.325 g, 2.36 mmol) under argon at 80° C. over 30 minutes. After 2.5 hours, BCHPC (47 mg) is added. After 5 hours (total), the reaction mixture is cooled, evaporated under vacuum and the residue purified by chromatography on silica gel, eluting with 2–5% EtOH/CHCl$_3$ to give the product as a mixture of two diastereomers.

$^{31}$P nmr (CDCl$_3$, 24 MHz) δ 56.3, 56.1 ppm

The isomers can be separated by chromatography with ethyl acetate as eluent:

$^{31}$P nmr (CDCl$_3$, 24 MHz) δ 57.1 ppm $^1$H nmr (CDCl$_3$, 400 MHz) δ 4.80 (t, Hz, J 4.0H2) ppm $^{31}$P nmr (CDCl$_3$, 24 MHz) δ 57.0 ppm $^1$H nmr (CDCl$_3$, 400 MHz) δ 4.92 (t, H2, J 4.0 Hz) ppm

EXAMPLE 8

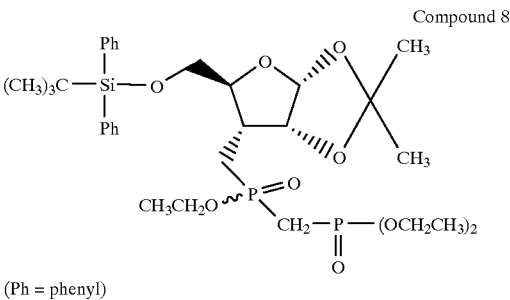

Compound 8

(Ph = phenyl)

A solution of Compound C (2.90 g, 6.83 mmol) and BCHPC (0.27 g, 0.68 mmol) in toluene (3 ml) is added to stirred Compound E (2.00 g, 8.19 mmol) under argon at 80° C. over 30 minutes. After 4 hours, the reaction mixture was cooled and purified by silica gel chromatography, eluting with 0–5% ethanol in ethyl acetate, to give Compound 8 as a mixture of two diastereoisomers.

$^{31}$P nmr (CDCl$_3$, 24 MHz) δ 45.81, 45.56, 45.35, 45.12, 20.04, 19.80 ppm

Elemental Analysis expected: C 55.24%, H 7.70%, P 8.9% C$_{32}$H$_{50}$O$_9$P$_2$Si.1.5H$_2$O found: C 55.5%, H 7.7%, P 7.6

EXAMPLE 9

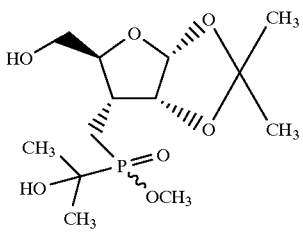

Compound 9

A solution of Compound F (0.55 g, 3.0 mmol) and BCHPC (0.24 g, 0.6 mmol) in toluene (1 ml) is added dropwise to stirred Compound B (0.82 g, 6.0 mmol) at 80° C., under argon. After 4.5 hours, the reaction mixture is evaporated and subject to short path distillation to remove excess Compound B (80–100° C., 0.003 mmHg). The residue is chromatographically purified on silica gel, eluting with 5% EtOH in chloroform, to give Compound 9, an oil, as a mixture of his diastereomers.

$^{31}$P nmr (CDCl$_3$, 24 MHz) δ 58.0, 57.6 ppm

Elemental Analysis Expected: C 43.33%, H 8.11%, P 8.60% C$_{13}$H$_{25}$O$_7$P.2H$_2$O Found: C 43.6%, H 8.1%, P 8.9%

EXAMPLE 10

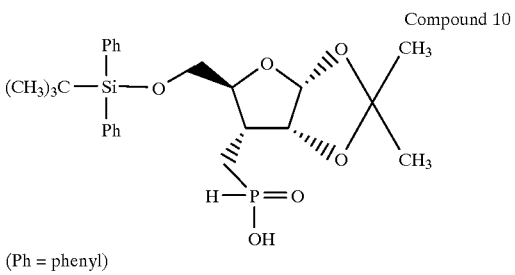

Compound 10

(Ph = phenyl)

A solution of Compound 7 (1.7 g, 2.8 mmol) and 1,8 diazabicyclo[5.4.0]undec-7-ene (DBU) (0.63 ml, 42 mmol) in methanol (15.3 ml) is heated to 70° C. After 6 hours, the reaction mixture is cooled and evaporated to give a mixture of Compound 10 as a DBU salt and excess DBU.

$^{31}$P nmr (CDCl$_3$, 161 MHz) δ 22.2 ppm

EXAMPLE 11

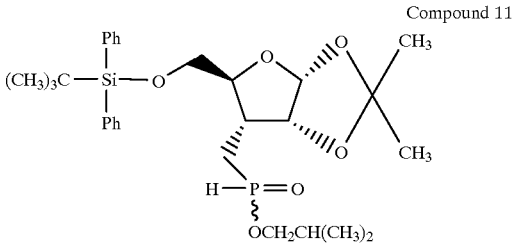

Compound 11

(Ph = phenyl)

A solution of crude Compound 10 as obtained in Example 10 (12.0 g, 14.5 mmol) in dichloromethane (120 ml) is cooled to −10° C. and isobutyl chloroformate (2.65 ml, 20.3 mmol) is added dropwise over ten minutes. After 30 minutes, additional chloroformate (3.79 ml, 29.0 mmol) and triethylamine (4.04 ml, 29.0 mmol) are added dropwise at less than −10° C. The reaction mixture is allowed to warm to 20° C. After 3.5 hours, the mixture is evaporated, diluted with ethyl acetate and washed with water. The organic phase is dried over magnesium sulphate, evaporated, and purified by silica gel chromatography, eluting with ether then an ethanol/ethyl acetate gradient. Compound 11, a solid, is obtained as a mixture of two diastereomers.

$^{31}$P nmr (CDCl$_3$, 24 MHz) δ 36.4, 35.8 ppm $^1$H nmr (CDCl$_3$, 400 MHz) δ 7.20 ppm (br.s., 1H, J$_{PH}$ 540 Hz) ppm mass spectrum C.I.(NH$_3$) 547 (MH$^+$), 564 (MNH$_4^+$)

EXAMPLE 12

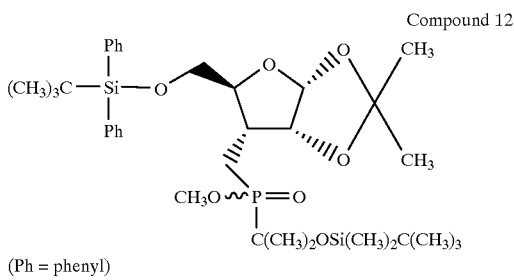

Compound 12

(Ph = phenyl)

To a solution of tertbutyldimethylsilylchloride (0.77 g, 5.1 mmol), triethylamine (0.71 ml, 5.1 mmol) and Compound 7 (2.6 g, 4.6 mmol) in dichloromethane (6 ml) at 0° C., 4-dimethylaminopyridine (62 mg, 0.51 mmol) is added. The mixture is allowed to warm to 20° C. immediately and stood at 20° C. for 18 hours. The solvent is evaporated and the residue purified by silica gel chromatography, eluting with an ether/hexane gradient, to give Compound 12 as a mixture of two diastereoisomers.

$^{31}$P nmr (CDCl$_3$, 24 MHz) δ 56.16, 56.37 ppm $^1$H nmr (CDCl$_3$, 400 MHz) δ 0.90 (s, $^t$Bu), 0.70 and 0.73 (2×s, $^t$Bu), 0.00 (2×s, 3H), −0.03 (2×s, 3H) ppm

EXAMPLE 13

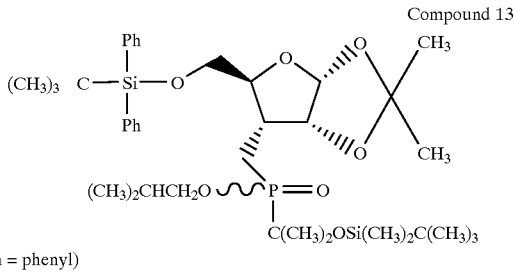

Compound 13

(Ph = phenyl)

To a solution of Compound 6 (2.2 g, 3.6 mmol) and triethylamine (0.66 ml, 4.7 mmol) in dichloromethane (10 ml) at 0° C., tertbutyldimethylsilylchloride (0.66 g, 4.35 mmol) is added dropwise, followed by 4-dimethylaminopyridine (40 mg, 0.36 mmol). The reaction mixture is allowed to warm to 20° C. and stirred for 45 hours, whereupon further quantities of the silyl chloride (0.27 g) and triethylamine (0.28 ml) are added. After a further 3.5 hours, the reaction mixture is evaporated, diluted with ether and filtered through 'Hyflo' and finally evaporated The residue is purified by dry flash chromatography on silica gel, eluting with hexane/ethylacetate (1:1–0:1) to give Compound 13.

$^{31}$P nmr (CDCl$_3$, 24 MHz) δ 54.2 ppm $^1$H nmr (CDCl$_3$, 400 MHz) δ 0.0 (s, 6H), 0.80 (s, 9H), 0.95 (s.9H) ppm.

EXAMPLE 14

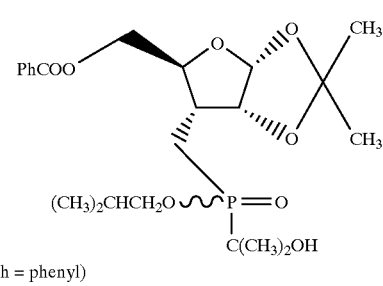

Compound 14

(Ph = phenyl)

A solution of Compound G (12.18 g, 41.96 mmol) and BCHPC (1.25 g, 3.1 mmol) in toluene (19 ml) is added dropwise over 35 minutes to Compound D (8.17 g, 45.3 mmol) under argon at 80° C. After 75 minutes, further BCHPC (0.30 g) is added. After a further 90 minutes, the reaction mixture is cooled, evaporated and dissolved in boiling ethyl acetate (15 ml). Hexane is added until the solution becomes cloudy. The solid which precipitates upon cooling is collected and washed with cold ether. The filtrate is partially evaporated and ether is added, whereupon further solid is precipitated and filtered off. The filtrate is evaporated and the resulting residue purified by dry flash chromatography on silica gel, eluting successively with ether and an ethanol/ethyl acetate gradient (0–5%) to give Compound 14 as a mixture of two ribo isomers and two xylo isomers, the former the major product.

$^{31}$P nmr (CDCl$_3$, 24 MHz) 54.17 (xylo); 53.81 (ribo) ppm

The solid precipitated during the purification procedure is a mixture of two ribo isomers of the product, enriched significantly in one isomer (25:4):

$^1$H nmr (CDCl$_3$, 400 MHz) δ 4.86 (t, 1H) major isomer; 4.93 (t, H) minor isomer ppm.

EXAMPLE 15

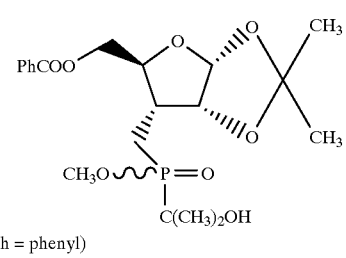

Compound 15

(Ph = phenyl)

A solution of Compound G (5.00 g, 17.2 mmol) and BCHPC (0.69 g, 1.7 mmol) in toluene (5 ml) is added dropwise over 1.25 hours to Compound B (2.85 g, 20.7 mmol) at 80° C. under argon. After 3.75 hours, the reaction mixture is cooled, evaporated and the residue purified by chromatography on silica gel, eluting with an ethanol/ethyl acetate gradient. Compound 15 is obtained as a mixture of two ribo and two xylo-isomers in a 10:1 ratio. The product is recrystallised from hexane/ethyl acetate to remove the minor xylo isomers.

$^{31}$P nmr (CDCl$_3$, 24 MHz) δ 56.25, 55.96, 55.79 (ribo), 55.70 (ribo) ppm

Elemental analysis expected: C 56.07%, H 6.82%, P 7.23% C$_{20}$H$_{29}$O$_8$P found: C 55.6%, H 7.2%, P 7.6% mass spectrum C.I. (NH$_3$) 429 (MH$^+$)

Further recrystallization gives one isomer (Isomer A) pure (98%).

$^{31}$P nmr (CDCl$_3$, 161 MHz) δ 56.27 ppm $^1$H nmr (CDCl$_3$, 400 MHz) δ 4.83 (t, 1H) ppm Recrystallisation of the residue from ether/hexane gives the other isomer (Isomer B)

$^1$H nmr (CDCl$_3$, 400 MHz) δ 4.89 (t, 1H) ppm

M/Z CI (NH$_3$) 429 MH$^+$

The two xylo isomers are separated from the ribo isomers by HPLC.

$^1$H nmr (CDCl$_3$, 400 MHz) δ 5.00 (d, J=3.6 Hz, 1H); 5.09 (d, 1H) ppm

EXAMPLE 16

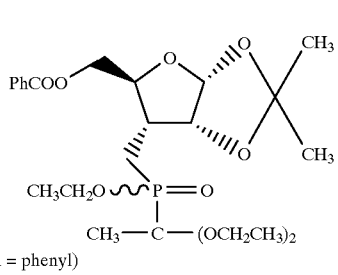

Compound 16

(Ph = phenyl)

A solution of Compound G (4.13 g, 14.2 mmol) and BCHPC (0.57 g, 1.42 mmol) in toluene (4 ml) is added dropwise over 10 minutes to ethyl (1,1-diethoxyethyl) phosphinate (4.49 g, 21.3 mmol) under argon at 75° C. Additional quantities of BCHPC (0.2 g) are added every hour. After 6 hours, the temperature is raised to 90° C., for 3 hours. The reaction mixture is cooled and purified by chromatography on silica gel, eluting with a hexane/ethyl acetate gradient. Excess phosphinate reactant is distilled out of the product using a short path apparatus (90° C./0.2 mmHg). The product, Compound 16 as a mixture of two major isomers, is further purified by chromatography, as above.

$^{31}$P nmr (CDCl$_3$, 24 MHz) δ 46.97, 46.63 ppm

EXAMPLE 17

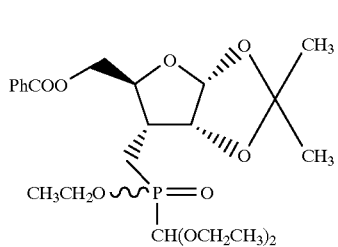

Compound 17

(Ph = phenyl)

A solution of Compound G (0.94 g, 3.2 mmol) and BCHPC (0.13 g, 0.32 mmol) in toluene (1 ml) is added dropwise to ethyl (diethoxymethyl)phosphinate (0.95 g, 4.86 mmol) under argon at 75° C. When the reaction is complete (TLC), the reaction mixture is cooled and purified by silica gel chromatography, eluting with an ethanol/ethylacetate gradient. The product, Compound 17 as a mixture of two isomers, is further purified by removing ethyl (diethoxymethyl)phosphinate by short path distillation (110° C./0.02 mmHg).

$^{31}$P nmr (CDCl$_3$, 24 MHz) δ 43.65 ppm

Elemental analysis expected: C 52.87%, H 7.56%, P 5.90% C$_{23}$H$_{35}$O$_9$P.2H$_2$O Found: C 52.9%, H 7.2%, P 5.9% M/Z CI (NH$_3$) 487 MH$^-$

EXAMPLE 18

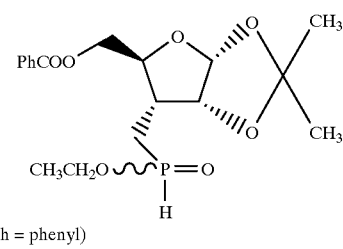

Compound 18

(Ph = phenyl)

To a solution of Compound 16 (1.79 g, 3.6 mmol) in chloroform (14 ml) and ethanol (3.6 ml) at 0° C., chloromethylsilane (0.50 ml, 3.9 mmol) is added. The reaction solution is stood at 10° C. for 64 hours and then at 20° C. for 4 hours. The solvent is evaporated and the residue purified by chromatography on silica gel. The product, Compound 18 as a mixture of two isomers, is diluted by a gradient of 0–20% ethanol in ethyl acetate.

$^{31}$P nmr (CDCl$_3$, 24 MHz) δ 34.34, 34.27 ppm J$_{PH}$ 557 Hz.

$^1$H nmr (CDCl$_3$, 400 MHz) δ 7.22 (d, 1H, J$_{PH}$ 550 Hz), 5.89 (t, 1H) ppm

EXAMPLE 19

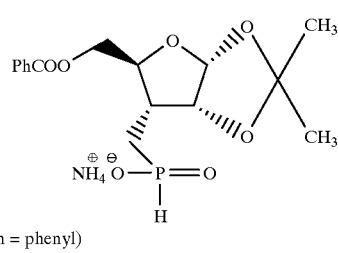

Compound 19

(Ph = phenyl)

A solution of Compound 15 (6.70 g, 15.6 mmol) in methanol (20 ml) and aqueous ammonia (33%, 20 ml) is stirred at 20° C. for 1 hour then tetrahydrofuran (10 ml) is added After 48 hours, the solution is evaporated, and the residue dissolved in water and extracted with chloroform until the product is fully extracted. The combined organic phase is evaporated and co-evaporated, to give Compound 19.

$^{31}$P nmr (D20, 24 MHz) δ 23 ppm $^1$H nmr (D$_2$O, 400 MHz) δ 7.05 (br. d., 1H, J$_{PH}$ 510 Hz), 6.89 (d, 1H) ppm

EXAMPLE 20

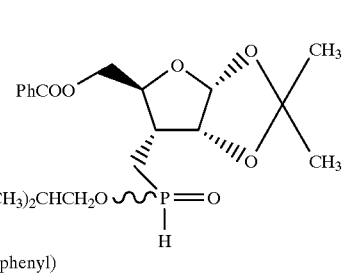

Compound 20

(Ph = phenyl)

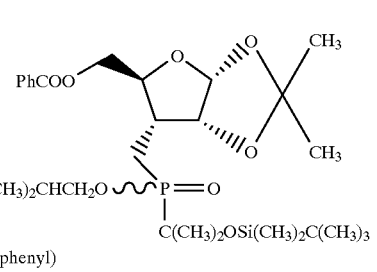

Compound 21

(Ph = phenyl)

To a solution of Compound 14 (262 mg, 0.56 mmol), triethylamine (0.068 ml, 0.67 mmol) and 4-dimethylaminopyridine (7 mg) in dichloromethane (2.5 ml) at 0° C., t-butyldimethylchloro silane (0.16 ml, 0.61 mmol) is added. The reaction mixture is warmed to 20° C. and stirred. After 24 hours, the reaction mixture is evaporated, ether is added, and the resulting solid separated by filtration. The filtrate is evaporated and the residue dissolved in dichloromethane (0.5 ml) and triethylamine (0.078 ml) further chlorosilane (84 mg) and 4-dimethylaminopyridine (7mg) are added. After 18 hours, the reaction mixture is evaporated and the residue is dissolved in ether and filtered The filtrate is evaporated and the residue is purified by silica gel chromatography.

Compound 21 is eluted with ethyl acetate/hexane (1:1), and is a mixture two isomers (3:1)

Compound 20 is eluted with ethyl acetate, and is a 2:1 mixture of two isomers

Compound 20:

$^{31}$P nmr (CDCl$_3$, 24 MHz) δ 35.3, 35.0 ppm (2:1) J$_{PH}$ 544 Hz.

$^1$H nmr (CDCl$_3$, 400 MHz) δ 7.22 (d, 1H, J$_{PH}$ 545 Hz), 5.90 (m, 1H) ppm

Compound 21:

$^{31}$P nmr (CDCl$_3$, 24 MHz) δ 54.1, 53.9 ppm (3.1)

$^1$H nmr (CDCl$_3$, 400 MHz) δ 0.76 (s, $^t$Bu), 0.74 (S, $^t$Bu) ppm

Elemental analysis Expected: C 59.57, H 8.45, Si 4.79, P 5.3% Found: C 59.6, H 8.4, Si 4.6, P 5.6

EXAMPLE 21

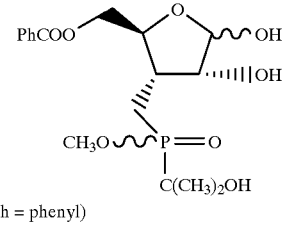
Compound 22

(Ph = phenyl)

Trifluoroacetic acid (15 ml) is added to a stirred solution of Compound 15 (2:1 ratio isomers) (1.55 g, 3.62 mmol) in dichloromethane (30 ml) at 20° C. After the addition of water (3.9 ml), the solution is sirred for 2.25 hours, then evaporated and co-evaporated with toluene at 0.5 mmHg pressure to give Compound 22.

$^1$H nmr (CDCl$_3$, D$_2$O, 400 MHz) δ 5.38 (s), 5.40 (s), 5.46 (d), 5.47 (d) ppm

EXAMPLE 22

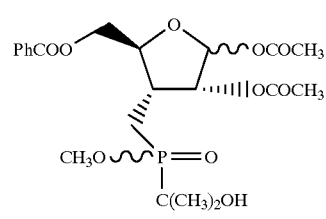
Compound 23

(Ph = phenyl)

Compound 22 is dissolved in pyridine (2.9 ml) and acetic anhydride (2.1 ml) is added After 43 hours, the reaction mixture is evaporated and the residue purified by silica gel chromatography, to give Compound 23 upon elution with a gradient of ethanol/ethyl acetate. The product is obtained as a mixture of two alpha and two beta anomers.

$^{31}$P nmr (CDCl$_3$, 24 MHz) δ 55.9, 56.7 ppm $^1$H nmr (CDCl$_3$, 400 MHz)

anomeric proton: δ 6.03 (s), 6.05 (s), 6.20 (d, J=4.0 Hz) 6.37 (d, J=4.2 Hz) ppm mass spectrum (CI, NH$_3$) 473 (MH$^+$), 490 (MNH$_4^+$)

Elemental analysis Expected: C 51.40%, H 6.38%, P 6.32% C$_{21}$H$_{29}$O$_{10}$P.H$_2$O Found: C 50.7%, H 5.9%, P 5.9%

EXAMPLE 23

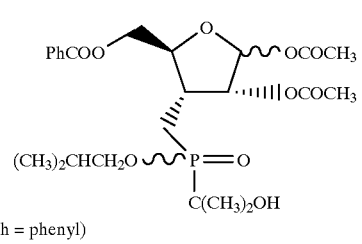
Compound 24

(Ph = phenyl)

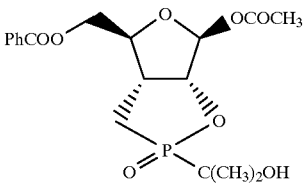
Compound 25

(Ph = phenyl)

Trifluoroacetic acid (60 ml) and water (20 ml) are added to a stirred solution of Compound 14 (15.6 g, 33.2 mmol) in dichloromethane (100 ml). After 3.75 hours, the solution is warmed to reflux for 30 minutes, and then stood at 20° C. for 18 hours. The solution is evaporated and coevaporated with toluene, and the residue dissolved in pyridine (27 ml). Acetic anhydride (19 ml) is added to the solution, which is then stood at 20° C. for 24 hours, whereupon 4-dimethylaminopyridine (150 mg) and acetic anhydride (6 ml) are added After 2 days, the solution is evaporated and purified by silica gel chromatography, Compound 24, the major product, a mixture of four isomers, is eluted by ethyl acetate and is further purified by chromatography in hexane/ethyl acetate.

$^{31}$P nmr (CDCl$_3$, 161 MHz) δ 54.9, 54.4, 54.0, 53.6 ppm

Compound 25, a single isomer, is obtained by trituration of the late column fractions with ether, to give a white solid.

Elemental analysis: Expected: C 54.27%, H 5.82%, P 7.78% Found: C 54.3%, H 5.7%, P 7.7%

$^{31}$P nmr (CDCl$_3$: d$^4$MeOH, 24 MHz) δ 81.0 ppm $^1$H nmr (CDCl$_3$, d$^4$MeOH, 400 MHz) δ 6.41 (s, 1H), 4.80 (dd, 1H, J 2.1, 5.3 Hz) ppm

EXAMPLE 24

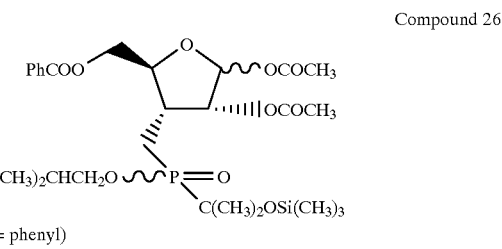
Compound 26

(Ph = phenyl)

To a solution of Compound 24 (10.3 g, 20.0 mmol) in dichloromethane (30ml), imidazole (4.1 g, 60 mmol) and then chlorotrimethyl silane (5.1 ml, 40 mmol) are added, the latter dropwise over 5 minutes. After 2.5 hours, the suspension is diluted with dichloromethane and extracted with water, then brine. The organic phase is dried over magnesium sulphate and evaporated. The residue is Compound 26.

$^{31}$P nmr (CDCl$_3$, 161 MHz) δ 54.3, 53.9, 53.4, 52.8 ppm $^1$H nmr (CDCl$_3$, 400 MHz) δ −0.02–0.06 (4s, 9H) ppm

EXAMPLE 25

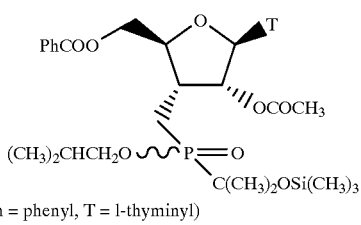

Compound 27

(Ph = phenyl, T = 1-thyminyl)

A suspension of thymine (1.66 g, 13.2 mmol) and bis(trimethyisilyl)acetamide (7.2 ml, 29 mmol) in 1,2 dichloroethane (20 ml) is heated to 70° C. for 2 hours, then cooled to 20° C. To this solution, a solution of Compound 26 (7.73 g, 13.2 mmol) in 1,2 dichloroethane (10 ml) is added. Trimethylsilyltriflate (3.1 ml, 15.8 mmol) is added dropwise to then cooled, the above solution, which is then heated to 50–55° C. for 2.5 hours. Aqueous sodium bicarbonate (30 ml) is added to the reaction mixture which is stirred for 10 minutes and diluted with chloroform and the aqueous phase extracted three times. The organic phase is separated, washed with brine and dried over magnesium sulphate before evaporation. The residue is purified by chromatography on silica gel, eluting with ethyl acetate. The product, Compound 27, is obtained as two separate isomers.

Early fraction $^{31}$P nmr (CDCl$_3$, 161 MHz) δ 53.50 ppm $^1$H nmr (CDCl$_3$, 400 MHz) δ 6.95 (s, 1H) 5.70 (d, 1H), 5.31 (dd, 1H), 4.22 (m, 1H) ppm Late fraction $^{31}$P nmr (CDCl$_3$, 161 MHz) δ 53.1 ppm $^1$H nmr (CDCl$_3$, 400 MHz) δ 6.88 (s, 1H), 5.63 (d, 1H), 5.38 (dd, 1H), 4.16 (m, 1H) ppm

EXAMPLE 26

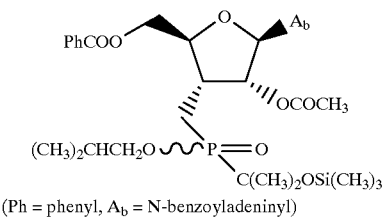

Compound 28

(Ph = phenyl, A$_b$ = N-benzoyladeninyl)

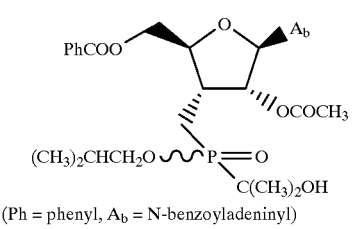

Compound 29

(Ph = phenyl, A$_b$ = N-benzoyladeninyl)

A suspension of N-benzoyl adenine (0.46 g, 1.9 mmol) and bis(trimethylsilyl)acetamide (0.96 ml, 3.9 mmol) in 1,2 dichloroethane (5 ml) is heated to 60° C. for 1 hour, then cooled. To this, a solution of Compound 26 (1.0 g, 1.9 mmol) in 1,2 dichloroethane (2 ml) is added. Trimethylsilyl triflate (0.94 ml, 4.9 mmol) is added dropwise to the above solution, which is then heated to 60° C. for 1.25 hours. The reaction mixture is subjected to the work-up and purification procedure of Example 25, except that the products, Compound 28 and 29, are eluted with 3% methanol/ethyl acetate.

Compound 28 is obtained as two separable isomers the later of which is a mixture with N-benzoyladenine.

$^{31}$P nmr (CDCl$_3$, 24 MHz)

eluted first δ52.5 ppm eluted second δ53.7 ppm $^1$H nmr (CDCl$_3$, 400 MHz)

eluted first δ5.85 (s, 1H), 5.76 (d, 1H), 0.00 (s, 9H) ppm eluted second δ5.87 (s, 1H), 5.70 (d, 1H), 0.00 (s, 9H) ppm Compound 29 is obtained as partly separable isomers:

$^{31}$P nmr (CDCl$_3$, 24 MHz)

eluted third δ53.3, 53.0 ppm (3:1 mixture)

eluted forth δ53.2 ppm $^1$H nmr (CDCl$_3$, 400 MHz)

eluted third δ6.08 (s, 1H), 5.92 (d, 1H), ppm minor isomer listed eluted forth δ6.01 (s, 1H), 5.86 (d, 1H) ppm Elemental Analysis Expected: C 58.87%, H 5.81%, N 10.10%, P 4.47% Found: C 58.6%, H 6.0%, N 10.0%, P 4.2%

EXAMPLE 27

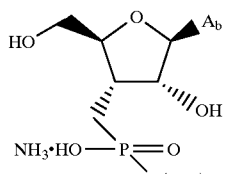

Compound 30

(Ph = phenyl, A$_b$ = N-benzoyladeninyl)

A solution of Compound 29 (0.44 g, 0.63 mmol) is methanol (5 ml) and aqueous ammonia (30%, 8 ml) is heated to 50° C. for 1 hour, then allowed to stand at 20° C. for 18 hours prior to evaporating to dryness. The residue is taken up in water and extracted with chloroform three times. The aqueous layer is subjected to purification by ion exchange chromatography on Dowex 50W×2H$^+$, eluting with H$_2$O then 3.5% aqueous ammonia. The product containing fractions are further chromatographed on Dowex 50W×2-NH$_4^+$ (water elution). The product obtained is dissolved in water, filtered and then subjected to chromatography on Dowex-50W×2H$^+$eluting with methanol then dilute aqueous ammonia. The product, Compound 30, is obtained as a white solid after freeze-drying.

$^{31}$P nmr (D$_2$O, 24 MHz) δ 43.4 ppm $^1$H nmr (D$_2$O, 400 MHz) δ 8.15 (s, 1H), 7.74 (s, 1H), 5.86 (s, 1H), 4.66(d, 1H), 1.30 (s, 3H), 1.26 (s, 3H) ppm Elemental Analysis Expected: C 38.18%, H 6.65%, N 19.09%, P 7.04% C$_{14}$H$_{25}$N$_6$O$_6$P.2H$_2$O Found: C 38.7%, H 6.5%, N 18.4%, P 6.5%

EXAMPLE 28

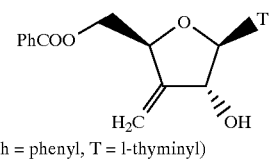

Compound 31

(Ph = phenyl, T = 1-thyminyl)

To a solution of Compound I (1.0 g, 2.5 mmol) in methanol (10 ml) a solution of potassium carbonate in water (0.17 g/0.25 ml) is added dropwise over 30 minutes. After 1 hour at 20° C., the reaction mixture is kept at −15° C. for 50 hours, then warmed to 20° C. for 5 hours. Acetic acid is added, until neutral, and the solution is evaporated. The residue is purified by silica gel chromatography, eluting with ethyl acetate, to give Compound 31.

$^1$H nmr (CDCl$_3$, 400 MHz) δ 7.24, (d, 1H, J 0.9 Hz), 5.95 (d, 1H, J 6.1 Hz), 5.57 (s, 1H), 5.33 (s, 1H) ppm Elemental Analysis: Expected: C 60.33%, H 5.06%, N 7.82%, Found: C 60.0%, H 5.2%, N 7.6

EXAMPLE 29

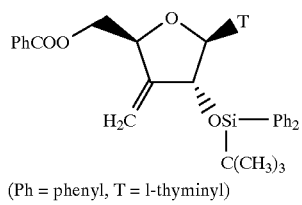

Compound 32

(Ph = phenyl, T = 1-thyminyl)

To a solution of Compound 31 (0.21 g, 0.59 mmol) in a mixture of dimethylformamide (1 ml) and chloroform, (1 ml), imidazole (60 mg, 0.88 mmol) and chlorodiphenylter-tbutylsilane (0.17 ml, 0.65 mmol) are added. After 3 days the reaction mixture is diluted with water and extracted with ethyl acetate. The organic phase is washed with water and brine, dried over magnesium sulphate and evaporated. The residue is purified by silica gel column chromatography, eluting first with 2:1 ethyl acetate/hexane then re-chromatographed with a 1:1 mixture of the above solvents, to give Compound 32.

$^1$H nmr (CDCl$_3$, 400 MHz) δ 6.50 (s, 1H), 5.98 (d, 1H), 5.50 (s, =1H), 5.34 (s, =1H), 1.08 (s, 1H) ppm

EXAMPLE 30

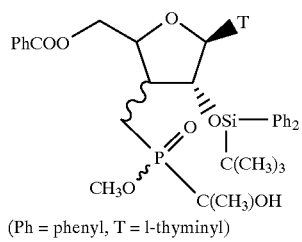

Compound 33

(Ph = phenyl, T = 1-thyminyl)

A solution of Compound 32 (0.20 g, 0.34 mmol) and BCHPC (13 mg, 0.03 mmol) in toluene (0.3 ml) is added dropwise to Compound B (56 mg, 0.40 mmol) at 75° C. under argon. After 3 hours, additional BCHPC (13 mg) is added, and after a further 2.75 hours, BCHPC (13 mg) is added. After a further 7 hours, the solution is cooled, evaporated, and the residue purified by silica gel chromatography, eluting with a gradient of hexane/ethyl acetate. The product, Compound 33, is obtained as a mixture of four isomers.

$^{31}$P nmr (CDCl$_3$ 161 MHz) δ 58.0, 57.7, 56.3, 56.1 ppm

The product can be further purified by HPLC, to give a mixture of three isomers.

$^1$H nmr (CDCl$_3$, 400 MHz) δ 6.18 (s, H1$^1$), 6.10 (d, H1$^1$), 6.01 (d, H1$^1$), 3.88 (d, OC$\underline{H}_3$) 3.80 (d, OC$\underline{H}$), 3.73 (d, O C$\underline{H}_3$) ppm

EXAMPLE 31

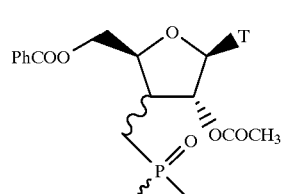

Compound 34

(Ph = phenyl, T = 1-thyminyl)

A solution of Compound I (0.40 g, 1.00 mmol) and BCHPC (40mg, 0.1 mmol) in toluene (0.5 ml) is added dropwise over 30 minutes to Compound B (0.28 g, 2.0 mmol) at 80° C. under argon. After 2.2 hours the reaction mixture is cooled, evaporated and purified by chromatography as silica gel, eluting with tetrahydrofuran. The product Compound 34, is obtained as a mixture of four isomers.

$^{31}$P nmr (CDCl$_3$, 24 MHz) δ 55.2, 55.0 ppm $^1$H nmr (CDCl$_3$, 400 MHz) δ 3.73 (d), 3.75 (d), 3.78 (d), 3.85 (d) [P-O C$\underline{H}_3$] ppm Elemental Analysis: Expected: C 51.9, H 5.8, N 4.2, P 5.0% Found: C 51.80, H 5.99, N 5.03, P 5.57% $C_{24}H_{31}\cdot N_2O_{10}P\cdot H_2O$

EXAMPLE 32

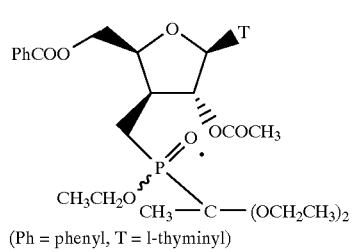

Compound 35

(Ph = phenyl, T = 1-thyminyl)

A solution of Compound I (4.00 g, 10.0 mmol) and BCHPC (0.3 g, 0.75 mmol) in toluene (7 ml) is added dropwise to ethyl (1,1-diethoxyethyl)phosphinate (4.20 g, 20.0 mmol) over 85 minutes at 80° C., under an argon atmosphere. Further BCHPC (0.5 g, 1.25 mmol) is added to the reaction mixture over 16 hours. The resulting mixture is subjected to short path distillation (100° C./0.03 mbar) and the residue is purified by silica gel column chromatography, eluting with a gradient of chloroform/methanol (100:0–98:2). The product is obtained as a mixture of ribo- and xylo-isomers.

$^{31}$P nmr (CDCl$_3$, 24 MHz) δ 46.0, 45.9, 45.8, 45.7 ppm

Further purification by column chromatogaphy, using a gradient of 2% to 20% ethanol in chloroform gives Compound 35 as a mixture of two xylo-isomers.

$^{31}$P nmr (CDCl$_3$, 24 MHz) δ 46.0, 45.8 ppm $^{1}$H nmr (CDCl$_3$, 400 MHz) δ 6.07, (d, H1$^1$), 6.05 (d, H1$^1$), 5.54–5.48 (m, 1H) ppm

EXAMPLE 33

Compound 36

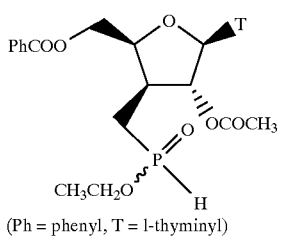

(Ph = phenyl, T = 1-thyminyl)

To a solution of Compound 35 (0.35 g, 0.57 mmol) in chloroform (5 ml) and ethanol (0.8 ml), chlorotrimethylsilane (0.22 ml, 1.7 mmol) is added dropwise. After 1 hour, a further quantity of the silane (1.0 ml) is added. After 4 hours, the solution is evaporated to give crude Compound 36.

$^{31}$P nmr (CDCl$_3$, 161MHz) δ 36.7, 36.5 ppm J$_{PH}$ 540 Hz

EXAMPLE 34

Compound 37

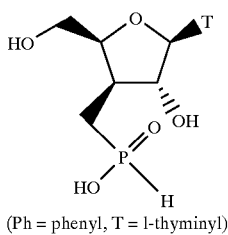

(Ph = phenyl, T = 1-thyminyl)

Aqueous ammonia (33%, 10 ml) is added to a solution of crude Compound 36 (0.28 g) in methanol (3.5 ml). After 20 hours at 20° C., the solution is heated to 70° C. for 1.5 hours. After cooling, the solution is evaporated, dissolved in water and extracted with chloroform. The aqueous phase is purified on an ion exchange resin (Dowex-H$^+$). The product is freeze-dried to give Compound 37 as a white solid.

$^{31}$P nmr (D$_2$O, 161 MHz) δ 31.7 ppm

Due to PH-PD exchange: δ31.3 (t, J$_{PD}$ 83 Hz)

$^{1}$H nmr (D$_2$O, 400 MHz) δ 7.09 (d, J$_{PH}$ 555 Hz), 5.71 (d, 1H, J 7.0 Hz) ppm

EXAMPLE 35

Compound 38

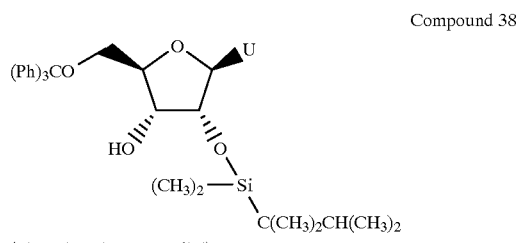

(Ph = phenyl, U = uracilyl)

To a solution of 5'-O-triphenylmethyluridine (21.5 g, 0.044 mol) in pyridine (25 ml) at 0° C., chlorodimethylthexylsilane (9.2 ml, 0.046 mol) is added dropwise. The suspension formed is stirred for 12 hours and stood for 58 hours at 20° C. The solid is filtered off and the filtrate evaporated. The residue is purified by silica gel column chromatography, eluting with chloroform. The Compound 38, is further purified by crystallisation (ether/chloroform).

$^{1}$H nmr (CDCl$_3$, 400 MHz) δ −0.15 (s, 3H), 0.00 (s, 3H); 5.25 (d, 1H, J 8.1 Hz), 5.84 (d,1H, J 3.7 Hz), 7.75 (d, 1H, J 8.2 Hz) ppm

EXAMPLE 36

Compound 39

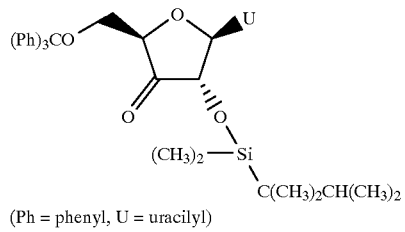

(Ph = phenyl, U = uracilyl)

Acetic anhydride (6.3 ml, 67 mmol) is added to a suspension of pyridinium dichromate in dichloromethane at reflux. After 10 minutes, a solution of Compound 38 (14.0 g, 22 mmol) in dichloromethane (40 ml) is added to the now black solution over 30 minutes. After 1 hour, ether/hexane (1:1) is added to the reaction mixture, which is then allowed to cool. The solution is filtered through 'Hi-flo', evaporated, dissolved in ether and refiltered through 'Hi-flo'. Evaporation of the filtrate under high vacuum gives Compound 39 which is used crude in Example 37

$^{1}$H nmr (CDCl$_3$, 400 MHz) δ 4.12 (m, 1H), 4.43 (d, 8.0 Hz), 5.27 (dd, 1H, J8.2, 2.0 Hz), 6.13 (d, 1H, J8.0 Hz) 7.50 (d, 1H, J 8.2 Hz) ppm

EXAMPLE 37

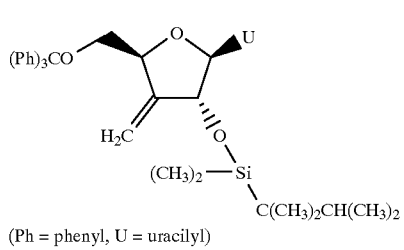

Compound 40

(Ph = phenyl, U = uracilyl)

n-Butyllithium (1.6M in hexanes, 27.0 ml, 43.2 mmol) is added to a suspension of triphenylmethylphosphonium bromide (15.5 g, 43.4 mmol) in tetrahydrofuran (115 ml) at −60° C.

After 1 hour, a solution of Compound 39 (12.4 g, 19.8 mmol) in tetrahydrofuran (25 ml) is added dropwise at −70° C. After 4 hours at −70° C., the suspension is allowed to warm slowly to 20° C. The suspension is recoded to −20° C. and acetic acid (1.85 g) is added. The solvent is evaporated and ether added to the residue. The mixture is filtered and the filtrate evaporated and purified by chromatography (silica gel), eluting the product with an ethyl acetate/ether gradient.

$^1$H nmr (CDCl$_3$, 400 MHz) δ 7.73 (d, 1H, J8.1 Hz), 5.85 (d, 1H, J6.2 Hz), 5.30 (t, 1H, J2.0 Hz), 5.21 (dd, 1H, J2.2, 8.1 Hz), 5.10 (t, 1H, J2.0 Hz) ppm

EXAMPLE 38

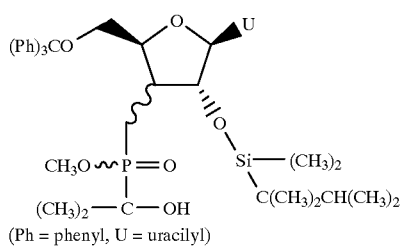

Compound 41

(Ph = phenyl, U = uracilyl)

A solution of Compound 40 (0.50 g, 0.8 mmol) and BCHPC (32 mg, 80 μmol) in toluene (2 ml) is added to Compound B (0.33 g, 2.4 mmol) over 15 minutes at 80° C., under an argon atmosphere. After 80 minutes, BCHPC (32 mg) is added. After a further 3 hours and 7 hours BCHPC (32 mg) is again added. After a further 4 hours, the reaction mixture is cooled, evaporated and the residue purified by silica gel chromatography, eluting with ethyl acetate. The first product-containing fractions eluted give Compound 41 as a maximum of three isomers.

$^{31}$P nmr (CDCl$_3$, 24 MHz) δ 57.3, 55.8, 55.7 ppm $^1$H nmr (CDCl$_3$, 400 MHz) δ 5.90 (d, 1H), 5.87 (d, 1H), 5.78 (s, 1H) ppm Later fractions contain mainly one isomer of the product, together with excess Compound B, the majority of which is removed by dissolving the mixture in ethyl acetate and washing the solution five times with water. The product is recovered by drying the solution with magnesium sulphate, and evaporation.

$^{31}$P nmr (CDCl$_3$, 161 MHz) δ 56.2 ppm $^1$H nmr (CDCl$_3$, 400 MHz) δ 5.78 (s, 1H) ppm

EXAMPLE 39

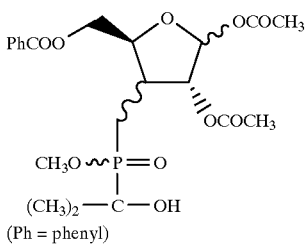

Compound 42

(Ph = phenyl)

A solution of Compound H (0.46 g, 1.4 mmol) and BCHPC (55 mg, 0.14 mmol) in toluene (1.5 ml) is added dropwise to Compound B (0.22 g, 1.6 mmol) in toluene (1 ml) at 80° C., under argon. After 2.5 hours, further BCHPC is added. After a further 2 hours more BCHPC is added and heating maintained at 70° C. for 3 hours. The resulting mixture is evaporated and the residue purified by silica gel column chromatography. Compound 42, a mixture of four diastereoisomers, is obtained on eluting with an ethanol (0–5%)/ethylacetate gradient.

$^{31}$P nmr (CDCl$_3$, 24 MHz) δ 55.8, 55.4, 55.1, 54.7 ppm $^1$H nmr (CDCl$_3$, 400 MHz) δ 6.10 (s, H1), 6.13 (s, H1), 6.42 (d, H1, J4.1 Hz), 6.44 (d, H1, J4.3 Hz) ppm Elemental Analysis: Expected: C 53.39, H 6.19, P 6.56%
Found: C 53.2, H 6.3, P 6.1

EXAMPLE 40

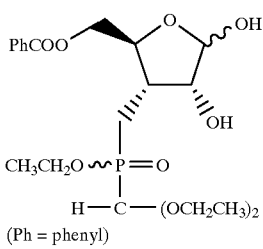

Compound 43

(Ph = phenyl)

Dowex 50wx-2 (H$^+$) ion-exchange resin (1 ml) is added to a solution of Compound 17 (150 mg, 0.31 mmol) in 1,2 dimethoxyethane (2 ml). The mixture i heated to 70° C. for 12 hours. The resin is filtered off and washed with tetrahydrofuran. The filtrate is evaporated and co-evaporated with toluene three times, to give Compound 43 as a mixture of isomers.

$^{31}$P nmr (CDCl$_3$, 24 MHz) δ 45.7, 45.6 ppm

EXAMPLE 41

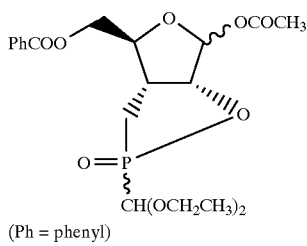
Compound 44

(Ph = phenyl)

Pyridine (0.25 ml) and acetic anhydride (0.17 ml) are added to crude Compound 43. The solution is allowed to stand for 41 hours and then evaporated. The residue is dissolved in toluene and filtered. The toluene is evaporated to give Compound 44 as a mixture of four isomers.

$^{31}$P nmr (CDCl$_3$, 24 MHz) δ 67.2, 65.0 ppm $^1$H nmr (CDCl$_3$, 400 MHz) δ 6.43 (s, H1), 6.34 (s, H1), 6.25 (s, H1), 6.11 (s, H1) ppm

EXAMPLE 42

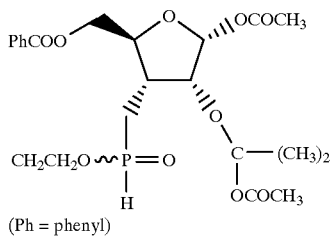
Compound 45

(Ph = phenyl)

To a solution of Compound 17 (150 mg, 0.31 mmol) in acetic acid (1.2 ml) acetic anhydride (0.44 ml) and p-toluenesulphonic acid (15 mg) are added. After 50 hours, the reaction mixture is added to iced water, which is then neutralised with sodium bicarbonate solution, and extracted with chloroform three times. The organic phase is dried over magnesium sulphate and evaporated. The residue is purified by silica gel chromatography, eludna with a petroleum spirit/ethyl acetate gradient. The product, Compound 45, is obtained as a mixture of two alpha anomers.

$^1$H nmr (CDCl$_3$, 400 MHz) δ 7.14 (d, PH, J 550 Hz), 6.28 (d, H1), 6.25 (d, H1), 1.50, 1.52, 1.54 (3×s, (CH$_3$)$_2$C) ppm

EXAMPLE 43

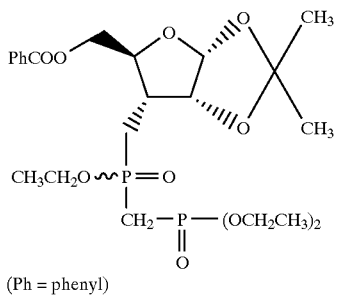
Compound 46

(Ph = phenyl)

To a degassed solution of Compound E (2.8 g, 11.7 mmol) in toluene (1 ml) under an argon atmosphere at 80° C. a solution of Compound G (2.0 g, 6.9 mmol) and BCHPC (0.2 g) in toluene (3 ml) is added dropwise over 20 minutes. The reaction is maintained at 75–80° C. and after 2 hours and 3 hours further BCHPC (2×0.1 g) is added. After a further 5 hours, the reaction mixture is cooled and purified by silica gel column chromatography, eluting with an ethanol/ethyl acetate radient, to give Compound 46 as a mixture of two diastereoisomers.

$^{31}$P nmr (CDCl$_3$, 161 MHz) δ 45.13, 45.09, 44.93, 44.90, 20.27, 20.25 ppm mass spectrum C.I. (NH$_3$) 536 (MH$^+$), 553 (MNH$_4^-$)

EXAMPLE 44

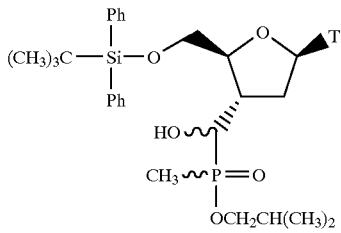
Compound 47

(Ph = phenyl, T = 1-thyminyl)

A solution of an aldehyde of formula XXIII where $R^5_a$ is hydrogen, $R^6$ is 1-thyminyl and $R^7$ is tert-butyldiphenylsilyl, prepared as described in WO 92/20823 (2.00 g, 4.05 mmol) in THF (18 ml) is added dropwise over 20 minutes to a solution of isobutyl methylphosphinate (0.55 g, 4.1 mmol) and DBU (0.60 ml, 4.1 mmol) in THF (7 ml). After 3 hours, more of the phosphinate (0.06 g) is added. After 4 hours, additional DBU (0.30 ml) and the phosphinate (0.27 g) are added. The reaction is then stored at −18° C. for 60 hours, warmed to 20° C. for 2 hours and then evaporated. The residue is purified by silica gel chromatography, eluting with 7% ethanol/chloroform. Compound 47 is obtained as a mixture of four isomers.

$^{31}$P nmr (CDCl$_3$, 161 MHz) δ 52.9, 52.5, 51.9, 51.4 ppm $^1$H nmr (CDCl$_3$, 400 MHz) 6.20 (t, H1$^1$), 6.27 (t, H1$^1$), 6.32 (t, H1$^1$) ppm

EXAMPLE 45

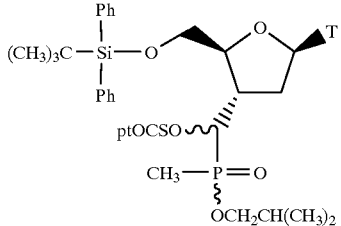
Compound 48

(Ph = phenyl, T = 1-thyminyl, pt = p-tolyl)

To a solution of Compound 47 (0.79 g, 1.26 mmol) and 4-dimethylaminopyridine (0.46 g, 3.8 mmol) in dichloromethane/acetonitrile (1:4, 25 ml) at 0° C., p-tolylchlorothionoformate (0.39 ml, 2.5 mmol) is added over 5 minutes. After 0.5 hours, the reaction mixture is stored for 18 hours at −18° C. The mixture is then warmed to 20° C. and an additional amount of the formate (0.27 ml) added in two batches over 6 hours. The reaction mixture is diluted with dichloromethane, evaporated onto silica gel, and purified by column chromatography. The product, Compound 48 as a mixture of four isomers, is eluted using a gradient of 0–10% ethanol/ethyl acetate.

$^{31}$P nmr (CDCl$_3$, 161 MHz) δ 47.6, 47.4, 46.3, 45.6 ppm $^1$H nmr (CDCl$_3$, 400 MHz) δ 2.28 (s, Ar—CH$_3$) ppm Elemental Analysis: Expected: C 60.28, H 6.70, N 3.52, S 4.02, P 3.89% C$_{40}$H$_{51}$N$_2$O$_8$PSSi.H$_2$O Found: C 60.95, H 6.9, N 3.8, S3.6, P 3.8

EXAMPLE 46

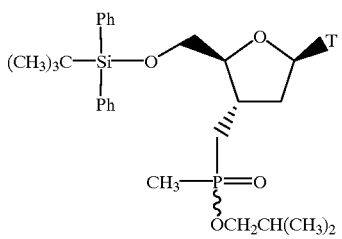

Compound 49

(Ph = phenyl, T = l-thyminyl)

A solution of Compound 48 (0.38 g, 0.49 mmol) and tris(trimethylsilyl) silane (0.30 ml, 0.98 mmol) in toluene (13 ml) is heated to 100° C., under an argon atmosphere, and azo bis(isobutyronitrile) (AIBN) (21 mg) in toluene (1.6 ml) is added batchwise in ten portions over 5.5 hours. The resulting mixture is cooled, evaporated, and the residue purified by silica gel chromatography, eluting the product with 0–5% ethanol in chloroform. Compound 49 is obtained as a mixture of two diastereoisomers (1:1).

$^{31}$P nmr (CDCl$_3$, 161 MHz) δ 52.4, 52.3 ppm $^1$H nmr (CDCl$_3$, 400 MHz) δ 1.45 (d, PCH$_3$, J 13.5 Hz), 1.46 (d, PCH$_3$, J 13.5 Hz)

Elemental Analysis: Expected: C 60.93, H 7.46, N 4.44, Si 4.45, P 4.91% C$_{32}$H$_{45}$N$_2$O$_6$PSi.H$_2$O Found: C 60.8, H 7.6, N 4.6, Si 3.9, P 4.4%

EXAMPLE 47

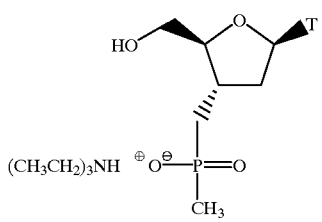

Compound 50

(T= 1-thyminyl)

Sodium hydroxide solution (1M, 0.6 ml) is added to a solution of Compound 49 (169 mg, 0.275 mmol) in methanol (1.2 ml). The solution is heated to 40° C. for 19 hours and then additional sodium hydroxide solution ( 1M, 2 ml) and lithium hydroxide solution (1.5M, 0.9 ml) are added at 20° C. and the mixture is stirred at 20° C. for 48 hours. Triethylammonium Dowex W×2 —ion exchange resin is added to the reaction mixture. The resin is washed with water and methanol, and the washings are evaporated. The residue is triturated with ether five times to give Compound 50 as a white solid.

$^{31}$P nmr (d$^4$-MeOH, 161 MHz) δ 38.7 ppm $^1$H nmr (d$^4$-MeOH, 400 MHz) δ 1.18 (d, PCH$_3$), 6.00 (d, 1H) ppm mass spectrum (FAB$^+$) 341 (MNa$^+$)

EXAMPLE 48

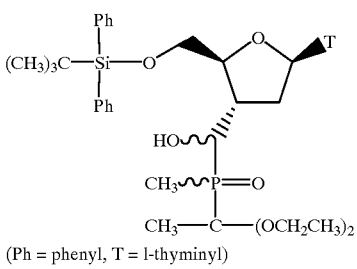

Compound 51

(Ph = phenyl, T = l-thyminyl)

To a solution of the aldehyde used in Example 44 (0.75 g, 1.49 mmol) in THF, Compound J (0.32 g, 1.79 mmol) is added, followed dropwise by DBU (0.22 ml, 1.5 mmol). After 6 hours, the reaction is concentrated and the residue purified by silica gel column chromatography. The product is eluted with a gradient of 0–8% methanol/chloroform to give Compound 51 as a mixture of four diastereoisomers.

$^{31}$P nmr (CDCl$_3$, 161 MHz) δ 52.1, 51.4, 50.5, 48.1 ppm mass spectrum (FAB$^+$) 673 (MH$^+$), 695 (MNa$^+$)

EXAMPLE 49

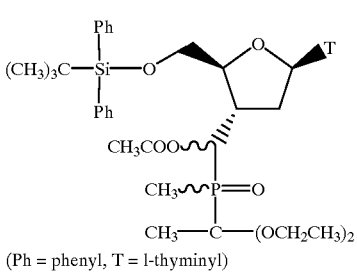

Compound 52

(Ph = phenyl, T = l-thyminyl)

A solution of Compound 48 (0.76 g, 1.1 mmol) and acetic anhydride (0.16 ml) in pyridine (0.27 ml) is stirred for 20 hours and then evaporated. The residue is purified by silica gel chromatography, eluting with an ethanol/ethyl acetate gradient. Compound 52 is obtained as a mixture of two isomers.

$^{31}$P nmr (CDCl$_3$, 161 MHz) δ 50.2, 46.6 ppm $^1$H nmr (CDCl$_3$, 400 MHz) δ 3.20 (m, H3$^1$), 3.30 (m, H3$^1$)

mass spectrum (FAB$^+$) 715 (MH$^+$) 737 (MNa$^+$)

EXAMPLE 50

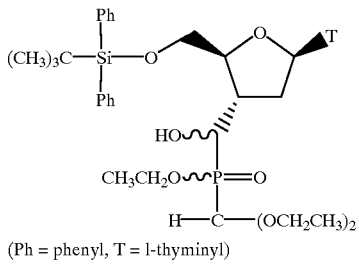
Compound 53

(Ph = phenyl, T = 1-thyminyl)

Compound K (0.16 ml, 0.6 mmol) is added dropwise to a solution of the aldehyde used in Example 44 (250 mg, 0.51 mmol) in pyridine (0.01 ml) and dichloromethane (3 ml). After 4 hours, DBU (0.022 ml) is added, and after a further hour, the solution is concentrated and co-evaporated with methanol then toluene. The residue is purified by silica gel column chromatography, eluting with 5% ethanol/chloroform to give Compound 53 as a mixture of two isomers.

$^{31}$P nmr (CDCl$_3$, 161 MHz) δ 38.9, 38.7 ppm

Further chromatography of impure fractions gives the product as a mixture of four isomers.

$^{31}$P nmr (CDCl$_3$, 161 MHz) δ 38.9, 38.7, 38.1, 37.8 ppm mass spectrum (FAB$^+$) 689 (MH$^+$), 711 (MNa$^+$)

EXAMPLE 51

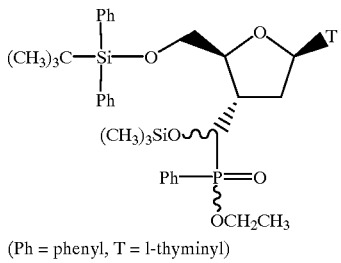
Compound 54

(Ph = phenyl, T = 1-thyminyl)

To a solution of ethyl phenylphosphonate (83 mg, 0.49 mmol) in dichloromethane (2 ml), bis(trimethylsilyltrifluoroacetamide) (0.52 ml, 1.95 mmol) is added. After 0.25 h, a solution of the aldehyde used in Example 44 (0.195 g, 0.39 mmol) in dichloromethane (2 ml) is added. The resulting solution is stored at 10° C. for 50 hours, then evaporated. The residue is purified by dry flash chromatography on silica gel. The product, Compound 54 as a mixture of isomers, is eluted by 1% ethanol/ethyl acetate.

$^{31}$P nmr (CDCl$_3$, 161 MHz) δ 38.2, 37.9 ppm $^1$H nmr (CDCl$_3$, 400 MHz) δ 6.17 (t, H1$^1$), 6.11 (t, H1$^1$), 6.03 (t, H1$^1$) ppm

EXAMPLE 52

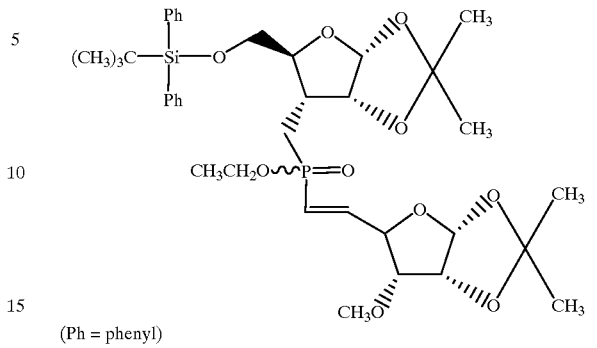
Compound 55

(Ph = phenyl)

To a solution of Compound 8 (0.83 g, 1.23 mmol) in tetrahydrofuran (6 ml) at −70° C., n-butyllithium (0.85 ml, 1.35 mmol) is added over 1 minute. After 10 minutes, a solution of Compound L (0.25 g, 1.23 mmol) in tetrahydrofuran (4 ml) is added over 1 minute. After 2 hours at −70° C., the mixture is slowly warmed to 0° C., then re-cooled to −55° C, whereupon saturated ammonium chloride solution (10 ml) is added. The aqueous mixture is extracted with dichloromethane three times. The organic phases are dried over magnesium sulphate, evaporated, and the residue purified by chromatography on silica gel. The product, Compound 55, consists of two separable isomers.

Less polar isomer
$^{31}$P nmr (CDCl$_3$, 24 MHz) δ 39.7 ppm
$^1$H nmr (CDCl$_3$, 400 MHz) δ 6.50 (dd, 1H), 6.60 (dd, 1H) ppm More polar isomer
$^{31}$P nmr (CDCl$_3$, 24 MHz) δ 39.9 ppm
$^1$H nmr (CDCl$_3$, 400 MHz) δ 6.18 (ddd, 1H), 6.89 (ddd, 1H) ppm
mass spectrum C.I. (NH$_3$) 717(MH$^+$)

EXAMPLE 53

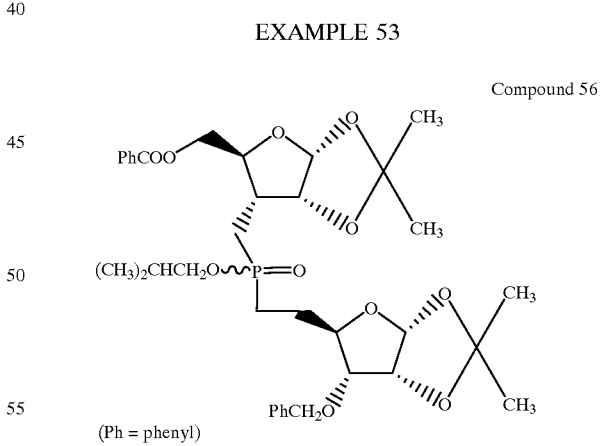
Compound 56

(Ph = phenyl)

A solution of Compound G (0.394 g, 1.36 mmol) and BCHPC (52 mg, 0.14 mmol) in toluene (0.2 ml) is added over 10 minutes to a solution of Compound N (0.515 g, 1.29 mmol) in toluene (0.2 ml) at 80° C., under argon. BCHPC (50 mg) is added over the next 9 hours in small batches. Also, after 5 hours an additional quantity of Compound G (0.10 g) is added. The reaction mixture is purified by silica gel column chromatography, and the product, Compound 56 as a mixture of two isomers, is eluted with ethyl acetate.

$^{31}$P nmr (CDCl$_3$, 161 MHz) δ 54.8, 54.5 ppm $^1$H nmr (CDCl$_3$, 400 MHz) δ 5.81 (d, J 3.5 Hz, 1H), 5.65 (d, J 3.8 Hz), 5.61 (d, J 3.8 Hz) ppm

EXAMPLE 54

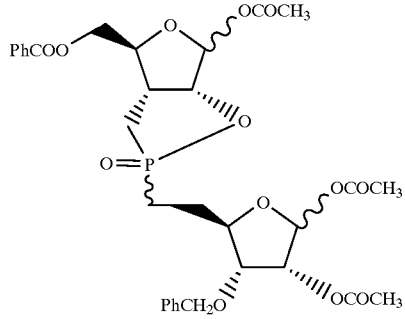

Compound 57

(Ph = phenyl)

A solution of Compound 56 (0.16 g, 0.23 mmol) in 1,2 dimethoxyethane (2 ml) containing Dowex 50 w×2-H$^+$ ion exchange resin (8 ml) is heated to 80° C. for 15 hours. The reaction is cooled, filtered, and evaporated. Proton NMR shows the loss of both isopropylidene groups and the iso-butyl ester group. The residue is dissolved in a solution of acetic anhydride (0.94 ml), pyridine (1.6 ml) and dichloromethane (2 ml). After 18 hours, the solution is evaporated, diluted with water and extracted with chloroform. The organic phase is dried over magnesium sulphate, and evaporated. Compound 57 is obtained as a mixture of isomers.

$^{31}$P nmr (CDCl$_3$, 161 MHz) δ 84.0, 83.5, 83.1 ppm

EXAMPLE 55

Compound 58

(Ph = phenyl)

A solution of Compound O (0.107 g, 0.47 mmol) and BCHPC (24 mg, 0.062 mmol) in toluene (0.75 ml) is added dropwise over 12 minutes to a solution of Compound 18 (0.24 g, 0.62 mmol) in toluene (0.5 ml) at 80° C., under an argon atmosphere. The mixture is heated for 6 hours and BCHPC (4×10 mg) is added during the course of the reaction. The resulting mixture is evaporated and the residue purified by silica gel chromatography. The product, Compound 58 as a mixture of two isomers, is eluted by a gradient of ethanol (0 to 5%) in ethyl acetate.

$^{31}$P nmr (CDCl$_3$, 161 MHz) δ 54.8, 54.4 ppm $^1$H nmr (CDCl$_3$, 400 MHz) δ 5.86 (t, 1H), 5.75 (d), 5.71 (d) ppm

EXAMPLE 56

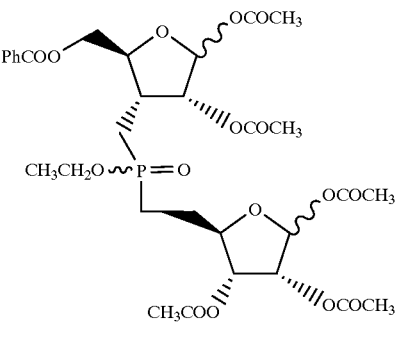

Compound 59

(Ph = phenyl)

A solution of Compound 58 (117 mg, 0.19 mmol) in trifluoroacetic acid (1.2 ml) water (0.3 ml) and dichloromethane (1.9 ml) is stirred at 20° C. for 5 hours, then evaporated and coevaporated with toluene three times. The residue is dissolved in pyridine (0.2 ml) and acetic anhydride (0.11 ml) is added After 24 hours, additional acetic anhydride (0.04 ml) is added. After a further 60 hours, the mixture is co-evaporated with toluene, and the residue is purified by silica gel chromatography, eluting with ethyl acetate. Compound 59 is obtained as a mixture of eight isomers.

$^{31}$P nmr (CDCl$_3$, 161 MHz) δ 55.2, 54.4, 53.9, 53.2. 53.1, 53.0, 52.9, 52.8 ppm mass spectrum CI. (NH$_3$) 717 (MNH$_4$$^+$)

EXAMPLE 57

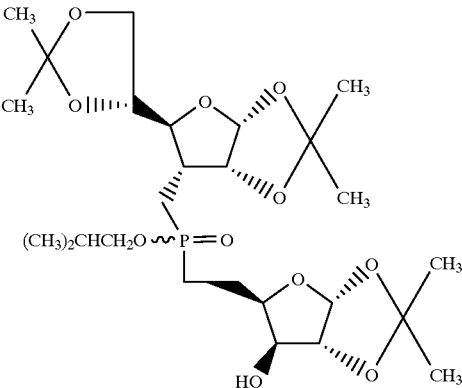

Compound 60

(Ph = phenyl)

A solution of Compound Q (58 mg, 0.31 mmol) and BCHPC (12 m,, 0.03 mmol) in toluene (0.5 ml) is added dropwise to a solution of Compound 4 (110 mg, 0.31 mmol) in toluene (0.5 ml) at 80° C. under argon. The mixture is heated for 13 hours, with additions of extra BCHPC throughout this time. The reaction mixture is evaporated and the residue purified by chromatography on silica gel. The product, Compound 60 as a mixture of two isomers, is eluted with 5% ethanol/chloroform.

$^{31}$P nmr (CDCl$_3$, 24 MHz) δ 57.7, 56.9 ppm $^1$H nmr (CDCl$_3$, 400 MHz) δ 5.79 (d, 1H), 5.91 (m, 1H) ppm Elemental Analysis: Expected: C 53.31, H 8.03, P 5.49%
Found: C 52.9, H 7.8, P 5.2% mass spectrum C.I. 565 (MH⁺)

EXAMPLE 58

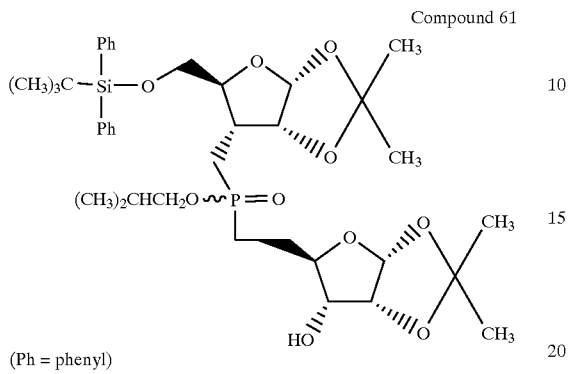

Compound 61

(Ph = phenyl)

A solution of Compound P (2.05 g, 11.0 mmol) and BCHPC (0.31 g, 0.8 mmol) in toluene (6.5 ml) is added over 1.5 hours to a solution of Compound 11 (6.03 g, 11.0 mmol) in toluene (5 ml) at 75° C. under an argon atmosphere. Further portions of BCHPC (5×30 mg) are added over 2 hours, at 30 minute intervals. After this time the mixture is cooled, pre-adsorbed onto silica gel, and purified by chromatography. The product is eluted by a gradient of methanol (0–100%) in ethyl acetate. The two isomers of the product, Compound 61 are separated by chromatography.

Less polar isomer
$^{31}$P nmr (CDCl$_3$, 161 MHz) δ 61.9 ppm
More polar isomer
$^{31}$P nmr (CDCl$_3$, 161 MHz) δ 62.2, 61.9 (2:1) ppm
Elemental Analysis Expected: C 62.27, H 7.84, P 4.23%
Found: C 62.0, H 8.1, P 4.0%
mass spectrum C.I. (NH$_3$) 733 (MH⁺)

EXAMPLE 59

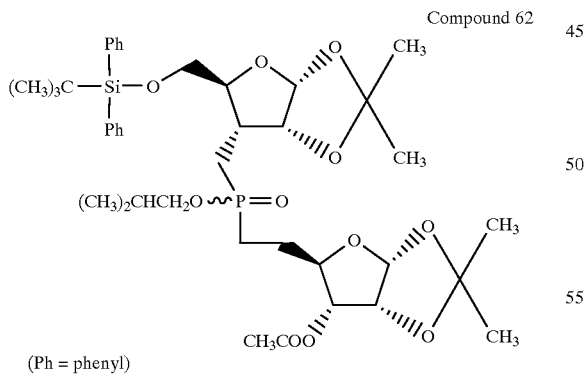

Compound 62

(Ph = phenyl)

To a solution of Compound 61 (1.0 g, 1.4 mmol) in dichloromethane (3 ml) and pyridine (1.1 ml), acetic anhydride (0.64 ml) and 4-dimethylaminopyridine (10 mg) are added. The mixture is stirred for 1.5 hours, then evaporated and the residue is purified by chromatography on silica gel, eluting with ethyl acetate. Compound 62 is obtained as a mixture of two isomers.

$^{31}$P nmr (CDCl$_3$.161 MHz) δ 55.3, 55.8 ppm

Elemental Analysis: Expected: C 61.28, H 7.71, P 3.95, Si 3.57%, Found: C 61.3, H 7.6, P 3.6. Si 3.5% mass spectrum C.I. (NH$_3$) 775 (80%, MNH$_4^+$)

EXAMPLE 60

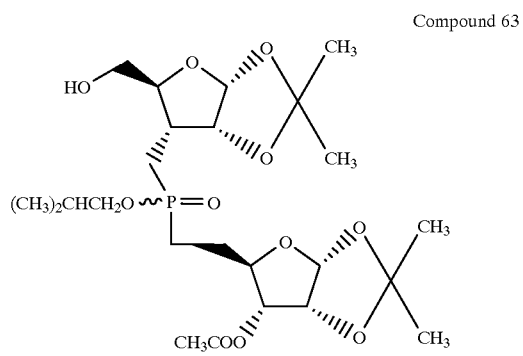

Compound 63

To a solution of crude Compound 62 (14.6 g, 15.3 mmol) in tetrahydrofuran (30 ml) water (1 ml) and pyridine (1 ml), a solution of tetra n-butylammonium fluoride trihydrate (5.3 g, 16.8 mmol) in tetrahydrofuran (25 ml) is added over 1.5 hours. The reaction mixture is maintained at 10° C. for 18 hours, then 20° C. for 5 hours before evaporation of solvent, and co-evaporation with toluene to give a residue containing Compound 63.

EXAMPLE 61

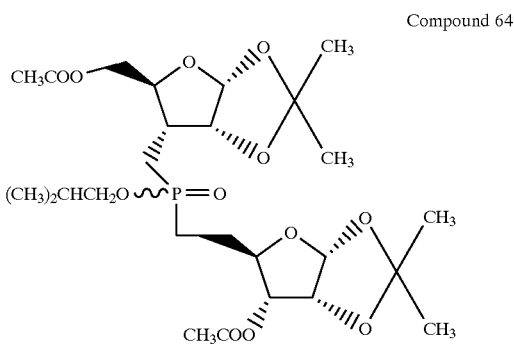

Compound 64

The residue from Example 60 is dissolved in pyridine (3 ml) and dichloromethane (25 ml), cooled to 0° C., and acetic anhydride (3 ml) added. The solution is allowed to stand at 20° C. for 18 hour, then evaporated. The residue is purified by silica gel column chromatography, eluting with 5% methanol/chloroform. Compound 64 is obtained as a mixture of two isomers.

$^{31}$P nmr (CDCl$_3$, 24 MHz) δ 54.6, 54.2 ppm

EXAMPLE 62

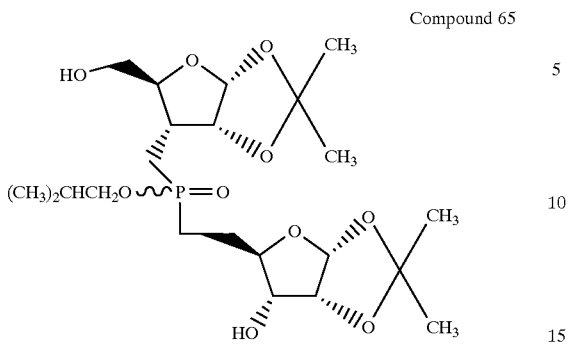

Compound 65

To a solution of Compound 61 (2.45 g, 3.34 mmol) in tetrahydrofuran (8 ml), water (1 ml) and pyridine (1 ml) a solution of tetra n-butyl ammonium fluoride trihydrate (1.05 g, 3.34 mmol), in tetrahydrofuran (7 ml) is added over 1 hour. After 3.5 hours, a further amount of the fluoride (1.05 g) is added in batches as a solid. The reaction is stood at 20° C. for 40 hours, then evaporated and co-evaporated with toluene. A portion of the material is purified by silica gel chromatography, eluting with 10% methanol/ethyl acetate to give Compound 65 and the remainder is used in subsequent Examples.

$^1$H nmr (CDCl$_3$, 400 MHz) δ 5.82 (d, 1H), 5.76 (d, 1H), 1.56 (s, CH$_3$), 1.50 (s,CH$_3$), 1.36 (s, CH$_3$), 1.31 (s, CH$_3$) ppm

EXAMPLE 63

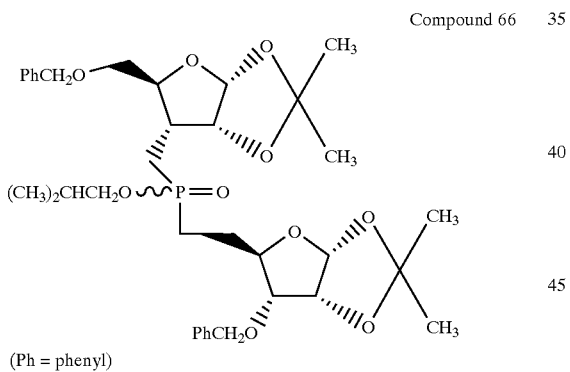

Compound 66

(Ph = phenyl)

To rapidly stirred solution of crude Compound 65 (255 mg, 0.35 mmol) in dry tetrahydrofuran (2 ml) at 0° C., sodium hydride (31 mg, 0.77 mmol) is added batchwise over 10 minutes. The mixture is allowed to warm to 20° C., and after 10 minutes, cooled to 0° C., whereupon benzylbromide (0.091 ml, 0.77 mmol) is added dropwise. The mixture is warmed to 20° C. and after 4 hours, additional sodium hydride (14 mg) is added. After 22 hours, further benzylbromide (0.013 ml) is added, followed 2 hours later by aqueous ammonium chloride. The aqueous phase is extracted with ethyl acetate, and the organic phase dried over magnesium sulphate and evaporated. The residue is purified by chromatography on silica gel, eluting with gradient of petroleum ether/ethyl acetate, to give Compound 66 as a mixture of two isomers.

$^1$H nmr (CDCl$_3$, 400 MHz) δ 7.38–7.22 (m, 10H), 5.82 (d, 1H), 5.69 and 5.66 (2×d, 1H) ppm

EXAMPLE 64

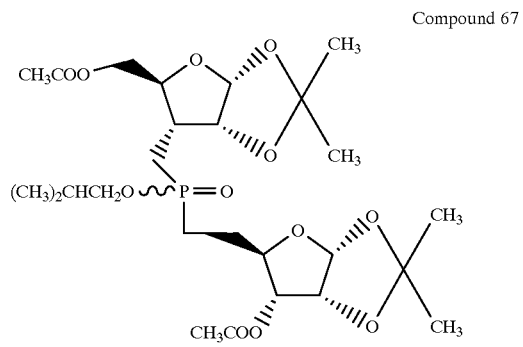

Compound 67

Acetic anhydride (3.0 ml) is added to a solution of Compound 65 (1.5 g, 3.34 mmol) in pyridine (5 ml) and dichloromethane (3 ml). After 20 hours at 20° C., the mixture is concentrated under vacuum and co-evaporated with toluene. The residue is dissolved in ether and filtered. The filtrate is evaporated and the residue purified by silica gel chromatography, eluting with 0–5% methanol in ethyl acetate to give Compound 67 as a mixture of two isomers:

$^{31}$P nmr (CDCl$_3$, 161 MHz) δ 54.8, 54.4 ppm $^1$H nmr (CDCl$_3$, 400 MHz) δ 2.15 and 2.08 (2×s, Ac) ppm Elemental Analysis: Expected: C 53.97, H 7.49, P 5.35%
Found: C 54.3, H 7.8, P 5.1%

EXAMPLE 65

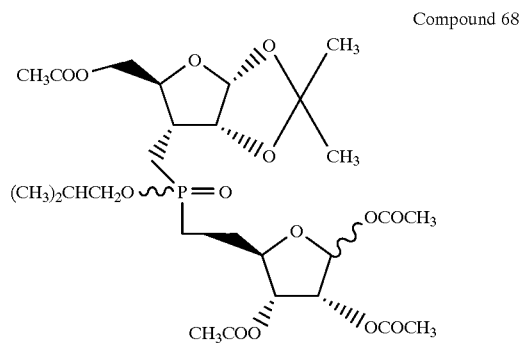

Compound 68

A solution of trifluoroacetic acid (0.5 ml) in water (0.5 ml) is added to a solution of Compound 61 (71 mg, 0.1 mmol) (3:20 ratio isomers) in 1,4 dioxan (0.5 ml). After 1.5 hours the solution is evaporated and co-evaporated with toluene three times. Pyridine (0.39 ml) and acetic anhdyride (0.18 ml) are added to the resulting residue. After 20 hours, the solution is evaporated and the residue purified by chromatography on silica gel, eluting with ethyl acetate, to give Compound 68 as a mixture of 3 isomers.

$^{31}$P nmr (CDCl$_3$, 24 MHz) δ 53.8, 53.5, 53.3 ppm $^1$H nmr (CDCl$_3$, 400 MHz) δ 1.33, 1.51(2 ×s, C(CH$_3$)$_2$) ppm

EXAMPLE 66

Compound 69

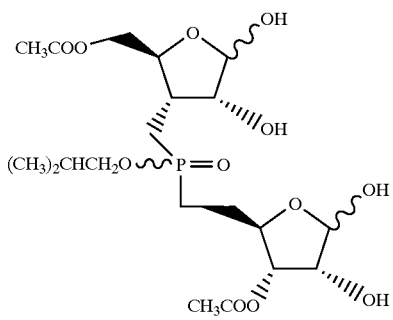

A solution of trifluoroacetic acid (5 ml) in water (1 ml) is added to a solution of Compound 67 (0.50 g, 0.86 mmol) in dichloromethane (1.5 ml). The resulting solution is stirred for 4 hours, evaporated, co-evaporated with toluene and the residue is purified by ion exchange chromatography on Dowex 50 W x 2-H$^+$, eluting with water, to give Compound 69 as a mixture of isomers.

$^{31}$P nmr (D$_2$O, 161 MHz) δ 63.2, 63.0, 62.8, 62.7, 62.6, 62.4, 62.3 ppm

EXAMPLE 67

Compound 70

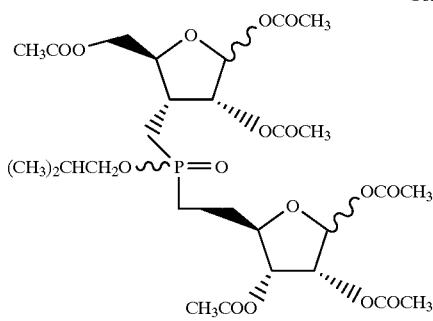

To a solution of Compound 69 in dichloromethane (1 ml), pyridine (1.1 ml) at −10° C., acetic anhydride (0.5 ml) and 4-dimethylaminopyridine (6.5 mg) are added. The reaction mixture is maintained at 10° C. for 60 hours, 20° C. for 18 hours and then evaporated. The residue is purified by silica gel chromatography, eluting with 0–5% methanol in ethyl acetate, to give Compound 70 as a mixture of eight isomers.

$^{31}$P nmr (CDCl$_3$, 161 MHz) δ 54.6, 54.5, 54.4, 54.0, 53.9, 53.3, 53.1, 53.0 ppm mass spectrum C.I. (NH$_3$) 684 (MNH$_4^+$)

EXAMPLE 68

Compound 71

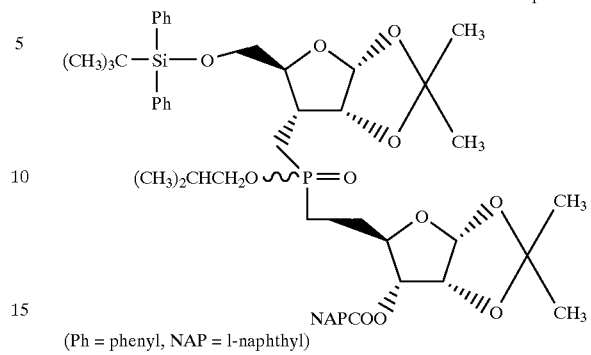

(Ph = phenyl, NAP = 1-naphthyl)

To a solution of Compound 61 (0.81 g, 1.11 mmol) in dry dichloromethane (3 ml) at 0° C., pyridine (0.13 ml) and 1-naphthoylchloride (0.20 ml, 1.33 mmol) are added dropwise. Finally 4dimetnylaminopyridine (8 mg) in dichloromethane (0.1 ml) is added dropwise. After 22 hours, the reaction mixture is evaporated, and the residue is purified by silica gel chromatography. The product, Compound 71 as a mixture of two isomers, is eluted with ethyl acetate.

$^{31}$P nmr (CDCl$_3$, 24 MHz) δ 54.5, 54.0 ppm

EXAMPLE 69

Compound 72

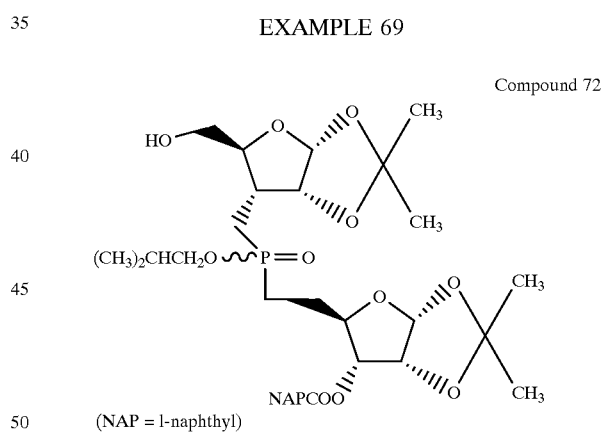

(NAP = 1-naphthyl)

To a solution of Compound 71 (0.70 g, 0.79 mmol) in dichloromethane (2 ml) at 0° C., tetra n-butyl ammonium fluoride (1M solution in THF, 1.0 ml) is added dropwise. The solution is allowed to warm to 20° C. and after 2 hours, additional tetra-n-butylammonium fluoride (0.5 ml) is added. After 4 hours the reaction is evaporated, and the residue is purified by dry flash chromatography on silica gel, eluting with ether then ethyl acetate, to give Compound 72 as a mixture of two isomers.

$^1$H nmr (CDCl$_3$, 400 MHz) δ 5.90 (m, 1H), 5.78 and 5.75 (2×d, 1H), 5.04 (t, 1H) ppm

EXAMPLE 70

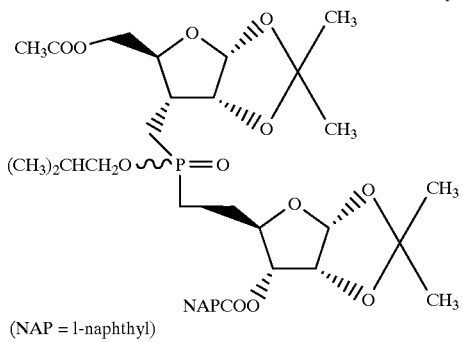

Compound 73

(NAP = 1-naphthyl)

To a solution of Compound 72 (0.33 g, 0.51 mmol) in pyridine (0.24 ml) acetic anhydride (0.23 ml) and 4-dimethylaminopyridine (6 mg) are added. The mixture is stood overnight, then evaporated. The residue is purified by chromatography on silica gel. Compound 73, a mixture of two isomers, is eluted with ethyl acetate.

$^{31}$P nmr (CDCl$_3$, 24 MHz) δ 53.6, 54.0 ppm

EXAMPLE 71

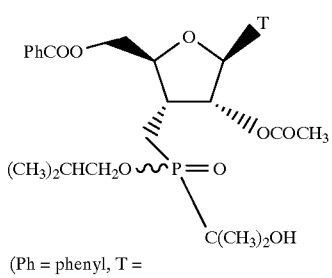

Compound 74

(Ph = phenyl, T =

A solution of Compound 27 (115 mg, 0.177 mmol) in a solution of tetrahydrofuran, acetic acid and water (5 ml, 4:1:1) is heated to 60° C. for 6 hours, cooled, evaporated and the residue is co-evaporated with toluene three times.

The product Compound 74, is used directly in the next Example.

$^{31}$P nmr (CDCl$_3$, 24 MHz) δ 53.4 ppm

EXAMPLE 72

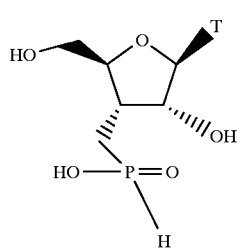

Compound 75

A solution of Compound 74 (124 mg, 0.21 mmol) in methanol (6 ml) and DBU (0.16 ml, 1.1 mmol) is stirred at 20° C. for 2 hours, then evaporated. The residue is purified by ion exchange chromatography, on Dowex 50W x 2-H$^+$ resin. The product is eluted with water, and freeze-dried to give Compound 75 as a white solid.

$^{31}$P nmr (D$_2$O, 161 MHz) δ 33.3 ppm $^1$H nmr (D$_2$O, 400 MHz) δ 7.08 (d, PH, J$_{PH}$ 550 Hz) ppm

EXAMPLE 73

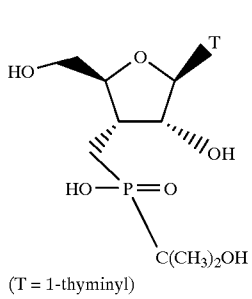

Compound 76

(T = 1-thyminyl)

A solution of Compound 27 (160 mg, 0.246 mmol) in methanol (3 ml) and aqueous ammonia (33%, 6 ml) is stirred for 3 days at 20° C., then evaporated, The residue is purified by ion exchange resin—Dowex-50W x 2H$^+$—to give Compound 76 as a white solid after freeze-drying.

$^{31}$P nmr (D$_2$O, 161 MHz) δ 53.7 ppm $^1$H nmr (D$_2$O, 400 MHz) δ 1.35 (s, 3H), 1.40 (s, 3H) ppm

EXAMPLE 74

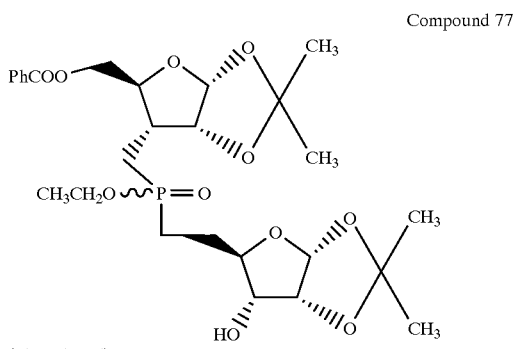

Compound 77

(Ph = phenyl)

Compound V (260 mg, 1.0 mm) is dissolved in dry toluene (2 ml) and evaporated in vacuo to afford an oily gum. To this product, under argon, is added, at 90° C. with stirring, a mixture of Compound G (285 mg, 1.0 mm), biscyclohexylperdicarbonate (40 mg, 0.1 mm) and toluene (0.4 ml) over 20 minutes. When addition is complete. the mixture is heated at 80° C. for 30 minutes. A few milligrams of biscyclohexyl perdicarbonate is added and heating continued for 30 minutes. This process is repeated 3 times until thin layer chromatography indicates significant product formation. The reaction mixture is purified by column chromatography over silica gel, eluting with chloroform, then 1–15% ethanol: chloroform mixtures. Further purification by column chromatography over silica gel, eluting with 2–8% ethanol: chloroform mixture gives Compound 77 as a colourless oil.

$^1$H nmr (δ, CDCl$_3$) 8.10 (2H, m, Ph—H), 7.70 (m, Ph—H), 7.42 (2H, m, Ph—H), 5.84 (1H, t, C-1), 5.78 (1H, d, C-1*) ppm $^{31}$P nmr (δ, CDCl$_3$) 61.7 and 61.4 ppm.

EXAMPLE 75

Compound 78

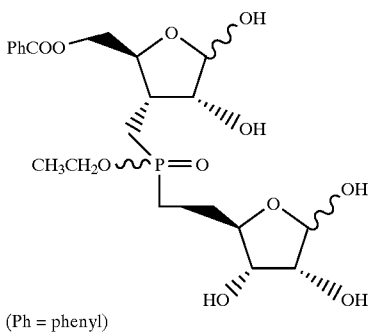

(Ph = phenyl)

Compound 77 (80 mg) is partitioned between dichloromethane (2.0 ml) and water (0.3 ml) and trifluoroacetic acid (1.2 ml) is added. The resulting solution is allowed to stand at room temperature for 1 hour, when t.l.c. shows reaction to be complete. Toluene (2 ml) is added to the reaction mixture and the solvents evaporated. The resulting residue is co-evaporated with more toluene (3×2 ml) and dried at high vacuum to afford Compound 78.

$^{31}$P nmr (CDCl$_3$, D4 MeOH) δ 59.74, 59.60, 58.82, 58.66

EXAMPLE 76

Compound 79

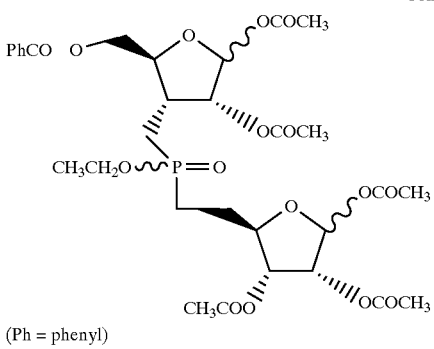

(Ph = phenyl)

Compound 78 (60 mg) is dissolved in acetic anhydride (1 ml) and pyridine (1 ml). The solution is allowed to stand at room temperature for 3 hours. Evaporation of the solvents leaves a residue which is co-evaporated with toluene (3×2 ml). Drying at high vacuum gives crude product which is purified by column chromatography over silica gel, eluting with ethyl acetate, to give Compound 79.

$^{31}$P nmr (CDCl$_3$) δ 54.40, 54.22, 53.92, 53.56, 53.27, 53.10, 52.95

EXAMPLE 77

Compound 80

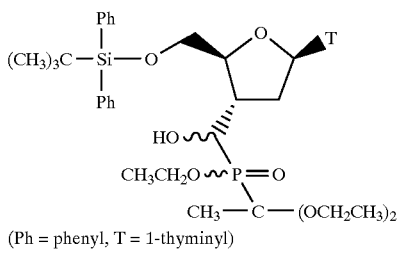

(Ph = phenyl, T = 1-thyminyl)

To a mixture of the aldehyde used in Example 44 (316 mg, 0.64 mmol) and ethyl (1,1-diethoxyethyl)phosphinate (200 mg, 0.95 mmol) in THF (15 ml) is added DBU (95 μl, 0.64 mmol) and the resulting mixture is stirred at room temperature for 1 hour. Concentration and passage through a short column of silica with dichloromethane-ethanol (3:1) and reconcentration gives a crude product which is further purified by flash silica column chromatography (eluant ethyl acetate; ethanol, 30:1) to give Compound 80 as a white solid, isolated as a mixture of four diastereoisomers.

$^{31}$P nmr $^1$H decoupled (CDCl$_3$, 162 MHz) δ 42.1, 40.9, 40.0 and 39.7 ppm

EXAMPLE 78

Compound 81

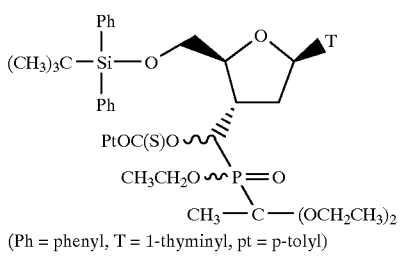

(Ph = phenyl, T = 1-thyminyl, pt = p-tolyl)

To a stirred solution of Compound 80 (300 mg, 0.42 mmol) and dimethylaminopyridine (51 mg, 0.42 mmol) in dry dichloromethane (10 ml) under an argon atmosphere is added triethylamine (78 μl, 0.56 mmol). The resulting mixture is cooled to 0° C. and p-tolylchlorothionoformate (86 μl, 0.56 mmol) is added dropwise over 2 minutes. The resulting solution is stirred at room temperature for 24 hours, followed by the addition of further quantities of triethylamine (58 μl, 0.42 mmol) and p-tolylchlomthionoformate (65 μl, 0.42 mmol). The resulting mixture is heated under reflux for 6 hours. Concentration and purification of the product by flash silica column chromatography (eluant: hexane-ethylacetate 1:1) gives Compound 81.

$^{31}$P nmr $^1$H decoupled (CDCl$_3$, 162 MHz) δ 37.4 and 35.7 ppm

EXAMPLE 79

Compound 82

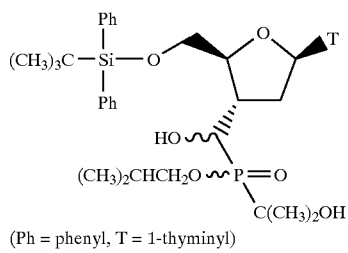
(Ph = phenyl, T = 1-thyminyl)

The aldehyde used in Example 44 and Compound D are reacted in the presence of DBU following the procedure of Example 77, but stirring at room temperature for 2.5 hours. Acetic acid (1.1 equivs) is added and the mixture is concentrated under vacuum. Purification by repetitive flash chromatography firstly with ethyl acetate-ethanol (25:1) as eluant followed by chloroform-ethanol (30:1) as eluant, gives Compound 82 as a white solid, isolated as a mixture of 4 diastereoisomers.

Found: C 59.4, H 7.2, N 4.1%; $C_{34}H_{49}N_2O_8PSi.H_2O$ requires C 59.1, H 7.45, N 4.05%

$^{31}P$ nmr $^1H$ decoupled (CDCl$_3$, 162 MHz) δ 49.0, 48.4, 48.2 and 48.0 ppm

EXAMPLE 80

Compound 83

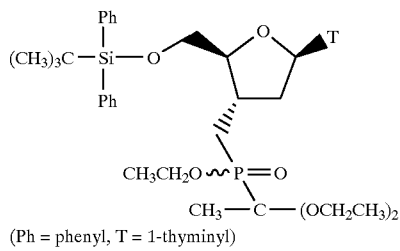
(Ph = phenyl, T = 1-thyminyl)

To a solution of ethyl (1,1-diethoxyethyl) phosphinate (5.51 g, 26.2 mmol) in dry THF (170 ml), under argon, at −78° C. is added a solution of potassium bis(trimethylsilyl) amide (34.6 ml, 0.75M solution in toluene) dropwise over 5 minutes. The resulting solution is stirred at −78° C. for 1 hour. A solution of Compound X (5.0 g, 8.25 mmol) in dry THF (20 ml) is then added dropwise over 5 minutes. Stirring is continued at −78° C. for 1 hour before warming to room temperature over 2 hours. Saturated aqueous ammonium chloride (50 ml) is then added and the whole mixture extracted with ethyl acetate (500 ml). The organic phase is washed with saturated ammonium chloride (2×50 ml) and water (2×50 ml), dried over magnesium sulphate and concentrated. Purification by flash silica column chromatography (eluant ethylacetate: ethanol 30:1) gives compound 83 as a mixture of 2 diastereoisomers.

EXAMPLE 81

Compound 84

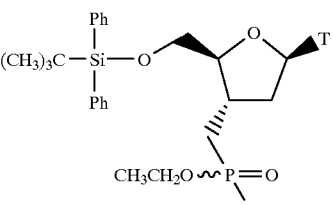
(Ph = phenyl, T = 1-thyminyl)

Trimethylsilychloride (4.44 ml, 35 mmol) is added dropwise (2 minutes) at room temperature to a stirred solution of Compound 83 (2.4 g, 3.5 mmol) in chloroform (25 ml) containing ethanol (1%) under argon. After standing at −20° C. for 60 hours, a further portion of trimethylsilyichloride (2.22 ml, 17.5 mmol) is added along with ethanol (200 μl) and the resulting solution stirred at room temperature for 7 hours. Concentration and co-evaporation with chloroform (50 ml) gives a white solid which is purified by flash silica column chromatography (eluant chloroform: ethanol 13:1) to give Compound 84 as a white solid isolated as a mixture of 2 diastereoisomers.

Found: C 59.95, H 7.25, N 4.65% $C_{29}H_{39}N_2O_6PSi.½H_2O$ C 60.1, H 6.95, N 4.85%

$^{31}P$ nmr $^1H$ decoupled (CDCl$_3$, 162 MHz) δ 34.5 and 34.3 ppm

EXAMPLE 82

Compound 85

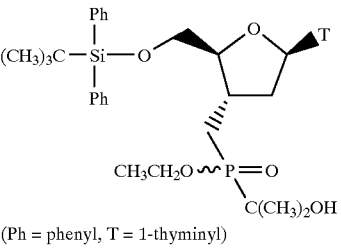
(Ph = phenyl, T = 1-thyminyl)

To a solution of Compound 84 (1.2 g, 2.1 mmol) in dry THF (30 ml) containing acetone (3.2 ml) is added in titanium (IV) isopropoxide (738 μl, 2.48 mmol). After 15 minutes, concentration and passage through a short column of silica (eluant ethyl acetate: ethanol 4:1) (500 ml) gives Compound 85 isolated as a mixture of 2 diastereoisomers.

$^{31}P$ nmr $^1H$ decoupled (CDCl$_3$, 162 MHz) δ 55.0, 54.7 ppm Found: C 57.7, H 7.05, N 4.05% $C_{32}H_{45}N_2O_7PSi.2H_2O$ requires C 57.8, H 7.4, N 4.2%

EXAMPLE 83

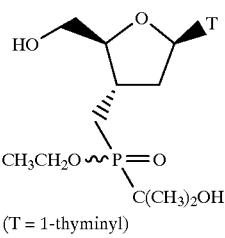

Compound 86

(T = 1-thyminyl)

To a solution of Compound 85 (1.02 g, 1.62 mmol) and acetic acid (92 μl, 16.1 mmol) in THF (10 ml) is added a solution of tetra-n-butyl ammonium fluoride (1.63 ml, 1.0 Molar). After stirring at room temperature for 1 hour, the mixture is concentrated and co-evaporated with chloroform (50 ml). Purification by flash silica column chromatography (eluant chloroform ethanol 9:1) gives Compound 86 isolated as a mixture of two diastereoisomers.

Found: C 45.55, H 6.85, N 6.4% $C_{16}H_{27}N_2O_7P.1\tfrac{2}{3}H_2O$ requires C 45.7, H 7.25, N 6.6%

$^{31}P$ nmr $^1H$ decoupled (CDCl$_3$, 162 MHz) δ 56.7, 56.5 ppm.

EXAMPLE 84

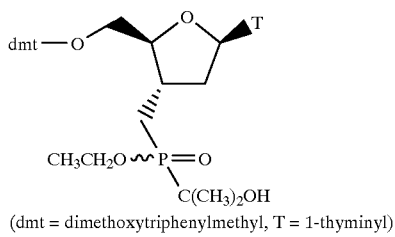

Compound 87

(dmt = dimethoxytriphenylmethyl, T = 1-thyminyl)

To a solution of Compound 86 (550 mg, 1.41 mmol) in pyridine (10 ml) is added dimethoxytritychloride (958 mg, 2.83 mmol). After stirring at room temperature for 20 hours, concentration and purification by flash silica column chromatography (eluant chloroform, methanol, triethylamine 100:5:1) gives Compound 87, isolated as a mixture of 2 diastereoisomers.

$^{31}P$ nmr $^1$decoupled (CDCl$_3$, 162 MHz) δ 54.9, 54.7 ppm.

EXAMPLE 85

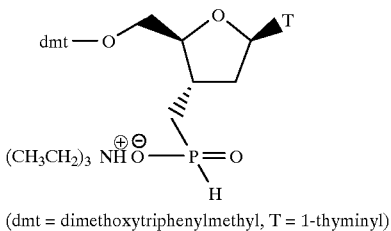

Compound 88

(dmt = dimethoxytriphenylmethyl, T = 1-thyminyl)

To a solution of Compound 87 (0.85 g, 1.22 mmol) in anhydrous methanol (10 ml) is added sodium methoxide (1.5 ml 4.4N solution in methanol). After stirring for 16 hours at room temperature, concentration and purification by flash silica column chromatography (gradient elution-chloroform, methanol, triethylamine 100:20:1–100:35:1) gives Compound 88 as a white powder.

$^{31}P$ nmr $^1H$ decoupled (CD$_3$OD, 162 MHz) δ 23.7 ppm.

EXAMPLE 86

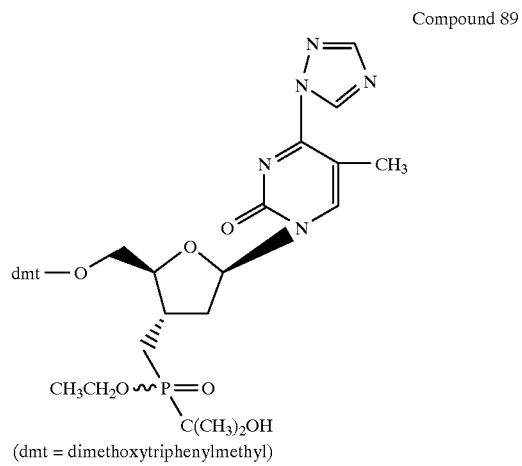

Compound 89

(dmt = dimethoxytriphenylmethyl)

To a solution of 1,2,4-triazole (69 mg, 1 mmole) in anhydrous pyridine (2ml) at 0° C. under argon is added triethylamine (300 μl, 4 mmol) followed by phosphorus oxychloride (18 μl, 0.2 mmol) dropwise over 2 minutes. To the resulting solution is added Compound 87 (75 mg, 0.11 mmol) in pyridine (0.5 ml). After stirring at room temperature for 1 hour, further portions of triethylamine (300 μl, 4 mmol) and phosphorus oxychloride (18 μl, 0.2 mmol) are added. After standing at room temperature for 20 hours, the solution is concentrated, dissolved in chloroform (10 ml) and washed with sodium bicarbonate (satd) (5 ml). The aqueous phase is reextracted with chloroform (10 ml) and the combined organic phase dried over Na$_2$SO$_4$, filtered and concentrated to give Compound 89 as a mixture of 2 diastereoisomers.

$^{31}P$ nmr $^1H$ decoupled (CDCl$_3$, 162 MHz) δ 55.2, 55.0 ppm.

EXAMPLE 87

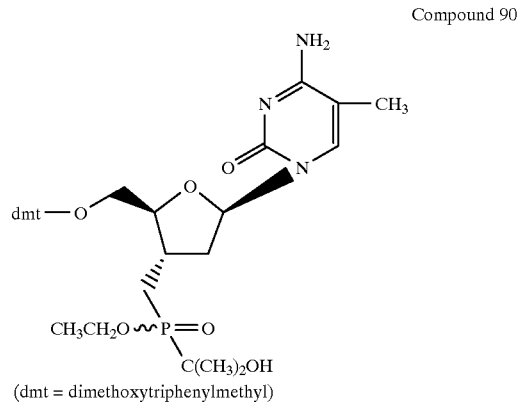

Compound 90

(dmt = dimethoxytriphenylmethyl)

Compound 89 (50 mg) is dissolved in conc. ammonia solution (5 ml). After standing at room temperature for 18 hours, concentration, co-evaporation with toluene and purification by flash silica column chromatography (gradient elution:ethyl acetate, methanol, triethylamine 100:12:1–100:20:1) gives Compound 90 as a mixture of 2 diastereoisomers.

$^{31}$P nmr $^1$H decoupled (CDCl$_3$, 162 MHz) δ 55.1 55.0 ppm.

EXAMPLE 88

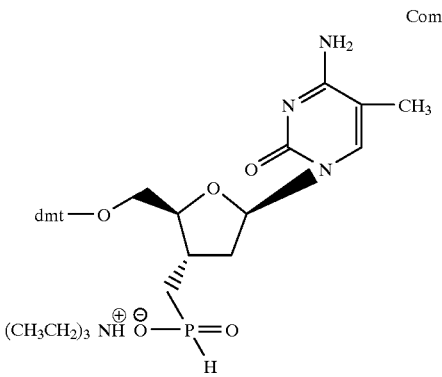

Compound 91

Compound 91 is prepared from Compound 90 using the procedure of Example 85. Purification by flash silica column chromatography (eluant:chloroform, methanol, triethylamine 100:67:1) gives Compound 91 isolated as the triethylamine salt $^{31}$P nmr $^1$H decoupled (CD$_3$OD, 162 MHz) δ 23.7 ppm.

EXAMPLE 89

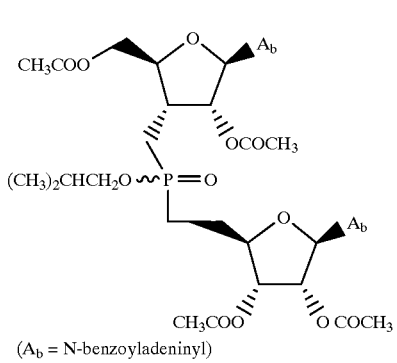

Compound 92

(A$_b$ = N-benzoyladeninyl)

To a suspension of N-benzoyladenine (59 mg, 0.25 mmol) in 1,2-dichloroethane (1 ml) bistnmethylsilylacetamide (123 μl, 0.50 mmol) is added. The suspension is heated to 75° C. for 0.75 hours, and the resulting solution is cooled to 20° C. To the above a solution of Compound 70 (76 mg, 0.11 mmol) in 1,2-dichloroethane (1.3 ml) is added, followed dropwise by trimethylsilyl tritluoromethanesulphonate (57 μl, 0.29 mmol). The mixture is stirred at 20° C. for 0.25 hours, then heated to 45–50° C. for a period of 8 hours. The solution is allowed to cool and pyridine (0.5 ml) is added. The reaction mixture is evaporated and purified by chromatography on silica gel, eluting with a gradient of ethanol/chloroform. Compound 92, a white solid is obtained as a mixture of diastereoisomers.

$^{31}$P nmr (162 MHz, CDCl$_3$) δ 52.9, 53.1 ppm m/z (FAB$^+$, thioglycerol) 1025 (MH$^+$)

EXAMPLE 90

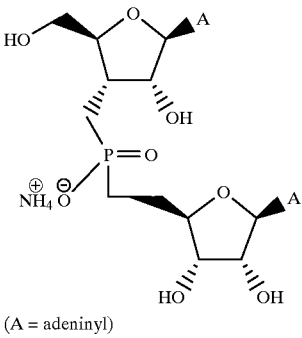

Compound 93

(A = adeninyl)

To a solution of Compound 92 (11 mg, 11 μmol) in methanol (4 ml) DBU (50 μl) is added, giving an immediate precipitate. After 20 hours at 20° C. the reaction mixture is evaporated and subjected to chromatography on the acid form of a sulphonic acid ion exchange resin, eluting with water then 5% aqueous ammonia. The product collected is further purified by chromatography on an ammonium ion exchange resin, eluting with water. Evaporation of the relevant fractions gives Compound 93 as a white solid.

$^{31}$P nmr (162 MHz, CDCl$_3$) δ 42.9 ppm m/z (FAB$^-$, thioglycerol) 593 (MH$^+$–NH$_3$)

EXAMPLE 91

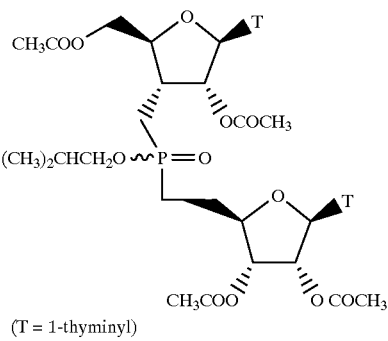

Compound 94

(T = 1-thyminyl)

To a suspension of thymine (0.33 g, 2.6 mmol) in 1,2 dichloroethane (4 ml) bistrimethylsilylacetamide (1.3 ml, 5.3 mmol) is added. The suspension is heated to 65° C. for 45 minutes, and the resulting solution is cooled to 20° C. A solution of Compound 70 (0.8 g, 1.2 mmol) in 1,2 dichloroethane (6 ml) is added, followed dropwise by trimethylsilyltrifluoromethanesulphonate (0.64 ml, 3.3 mmol). The mixture is stirred at 20° C. for 15 minutes, then heated to 65° C. for 2.5 hours. After cooling, saturated aqueous sodium bicarbonate (10 ml) is added slowly. The resulting mixture is extracted with chloroform three times. The combined organic phase is washed with brine, dried over magnesium sulphate and evaporated. The residue is purified by chromatography on silica gel, eluting with ethyl acetate/methanol gradient. Compound 94, a white solid, is obtained as a mixture of diastereoisomers.

$^{31}$P nmr (162 MHz, CDCl$_3$) δ 54.0, 54.2 ppm m/z (FAB$^+$, thioglycerol) 799 (MH$^+$)

EXAMPLE 92

Compound 95

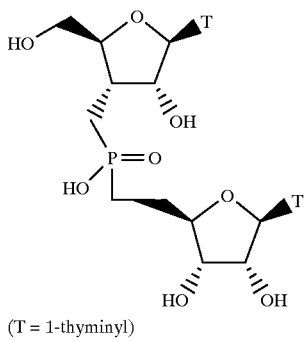

(T = 1-thyminyl)

To a solution of Compound 94 (200 mg, 0.25 mmol) in methanol (7 ml) DBU (50 μl) is added. After 15 hours at 20° C., a further amount of DBU is added (200 μl). After 4 hours, the reaction mixture is evaporated and the residue is purified on a sulphonic acid ion exchange resin, eluting with water. Compound 95 is obtained as a white solid after lyophilization.

$^{31}$P nmr (162 MHz, D$_2$O) δ 55.2 ppm m/z (FAB$^+$, thioglycerol) 575 (MH$^+$) 597 (MNa$^+$)

EXAMPLE 93

Compound 96

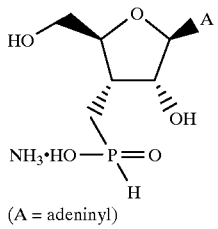

(A = adeninyl)

A solution of Compound 28 (202 mg, 0.264 mmol) in a mixture of acetic acid, water and THF (1:1:4, 6 ml) is heated to 55–60° C. for 6 hours, then evaporated to give crude Compound 29. The latter (0.18 g) is dissolved in methanol (7 ml) and DBU (0.19 ml, 1.32 mmol) is added. After 1.75 hours the solvent is evaporated. The residue is passed down a column of Dowex-50W X-2 H$^+$ from ion exchange resin, and product-containing fractions pooled and evaporated. The residue is dissolved in aqueous ammonia and stood at 20° C. for 3 days, after which time it is evaporated and purified by ion exchange chromatography first using a H$^+$ form column, and then an ammonium ion exchange resin. Compound 96 is obtained as a white solid after freeze-drying.

$^{31}$P nmr (D$_2$, 161 MHz) δ 26.1 ppm.

EXAMPLE 94

Compound 97

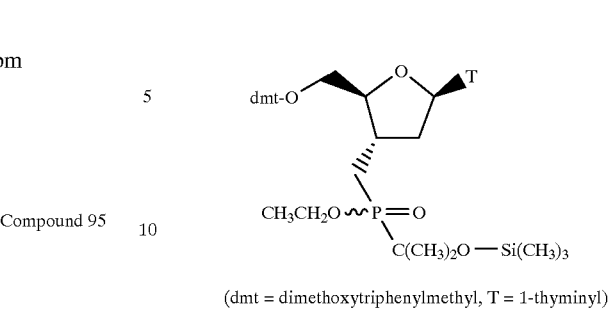

(dmt = dimethoxytriphenylmethyl, T = 1-thyminyl)

To a solution of Compound 87 (780 mg, 1.12 mmol) in dry dichloromethane (5 ml) is added bis(trimethylsilyl) trifluoroacetamide (1.5 ml, 5.65 mmol). The resulting mixture is stirred at room temperature for 2.5 hours, stood at 5° C. for 60 hours and stirred for a further 18 hours at room temperature. Concentration and purification by flash silica column chromatography (eluant 200:4:1 ethyl acetate: ethanol: triethylamine) gives a thick oil. Dissolution in dichloromethane, washing with water and drying (Na$_2$SO$_4$) then gives Compound 97, isolated as a mixture of two diastereoisomers.

$^{31}$P nmr $^1$H decoupled (CDCl$_3$, 162 MHz) δ 54.1, 54.0 ppm.

EXAMPLE 95

Compound 98

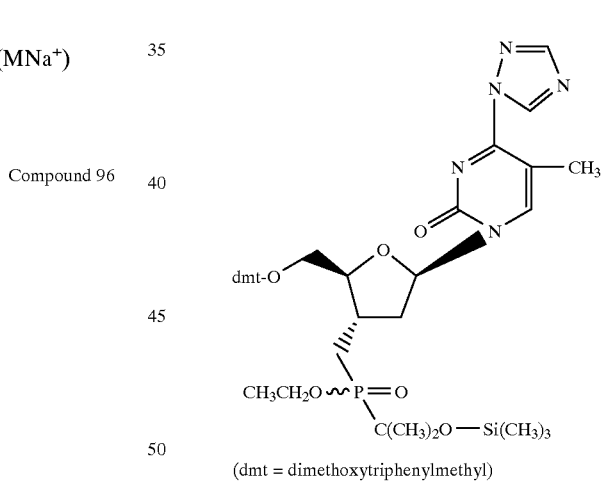

(dmt = dimethoxytriphenylmethyl)

To a solution of 1,2,4-triazole (196 mg, 2.84 mmol) in anhydrous pyridine (4 ml) at 0° C. under argon is added triethylamine (1.25 ml, 9 mmol) followed by phosphorus oxychloride (66 μl, 0.71 mmol) dropwise over 1 minute. The resulting solution is stirred at 0–5° C. for 5 minutes. To this solution is added a solution of Compound 97 (217 mg, 0.284 mmol) in anhydrous pyridine (2+2 ml) dropwise over 2 minutes. The resulting mixture is stirred at 0–5° C. for 10 minutes and stood at room temperature for 16 hours. The solution obtained is concentrated, dissolved in dichloromethane (30 ml) and washed with saturated aqueous sodium bicarbonate. The aqueous phase is re-extracted with dichloromethane and the combined organic phase dried over Na$_2$SO$_4$, filtered and concentrated to give Compound 98 as a mixture of 2 diastereoisomers.

$^{31}$P nmr $^1$H decoupled (CDCl$_3$, 162 MHz) δ 54.2, 53.8 ppm.

EXAMPLE 96

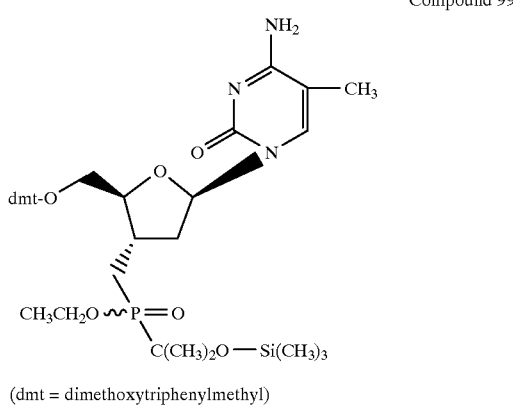

Compound 99

(dmt = dimethoxytriphenylmethyl)

Compound 99 is prepared from Compound 98 by the method of Example 87. Purification by flash silica column chromatography (gradient elution : dichloromethane : ethanol: triethylamine 200:13:1→200:20:1) followed by further flash silica column chromatography (gradient elution ethyl acetate:ethanol:triethylamine 200:13:1→200:70:1) gives Compound 99 as a mixture of 2 diastereoisomers.

$^{31}$P nmr $^1$H decoupled (CDCl$_3$, 162 MHz) δ 54.3, 54.1 ppm.

EXAMPLE 97

A solution of Compound 99 (470 mg, 0.61 mmol) in methanol (10 ml) containing DBU (0.46 ml) is heated at 60° C. for 3 hours. Concentration, dissolution in water:triethylamine (200:1) and passing through a Dowex 50W×2 column presaturated with triethylamine gives on elution with water/triethylamine (200:1) Compound 91 isolated as the triethylamine salt.

EXAMPLE 98

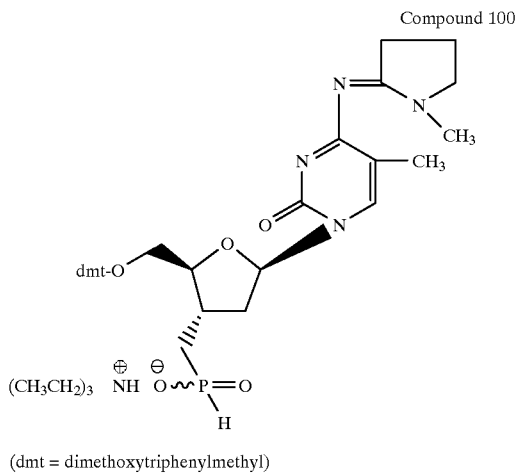

Compound 100

(dmt = dimethoxytriphenylmethyl)

To a solution of Compound 91 (420 mg, 0.59 mmol) in methanol (10 ml) containing triethylamine (0.17 ml, 1.22 mmol) is added N-methylpyrolidone diethylether (0.43 ml, 2.97 mmol). After standing at room temperature for 18 hours, a further portion of the ether is added (0.20 ml, 1.38 mmol) and the mixture is stirred for a further 3 hours. Concentration and purification by flash silica column chromatography (chloroform:methanol:triethylamine 200:60:1) gives Compound 100 as a white foam.

$^{31}$P nmr $^1$H decoupled (CD$_3$OD, 162 MHz) δ 23.7ppm.

EXAMPLE 99

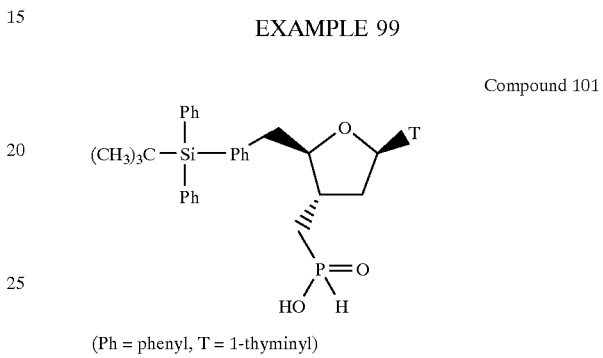

Compound 101

(Ph = phenyl, T = 1-thyminyl)

A solution of Compound 84 (0.78 g, 1.37 mmol) in ethanol (2.7 ml), water (1.4 ml) and triethylamine (2.7 ml) is stirred at room temperature. After 3 hours, the fraction mixture is diluted with ethyl acetate (25 ml), and washed successively with 0.05M aqueous HCl (1×10 ml) and water (1×10 ml). The organic extract is dried over magnesium sulphate and evaporated to give Compound 101 as a clear colourless viscous oil.

$^{31}$P (162 MHz, CDCl$_3$) δ 35.47 ppm.

EXAMPLE 100

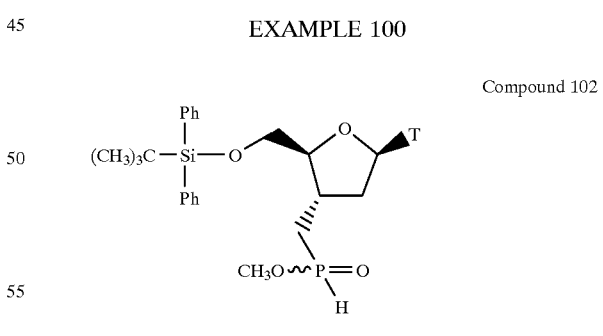

Compound 102

(Ph = phenyl, T = 1-thyminyl)

Dicyclohexylcarbodiimide (109 mg, 530 µmol) is added to a solution of Compound 101 (230 mg, 424 µmol) and 2,6-dimethylamino pyridine (0.6 mg, 5 µmol) in methanol (21.5 µl, 530 µmol) and tetrahydrofuran (4.2 ml) at 0° C. After stirring for 4 hours at room temperature, the reaction mixture is filtered and then evaporated.

Flash column chromatography of the evaporation residue on silica, eluting with 95% ethyl acetate, 5% methanol gives Compound 102 as a viscous clear colourless oil.

$^{31}$P (162 MHz, CDCl$_3$) δ 37.32, 37.08 ppm.

EXAMPLE 101

Compound 103

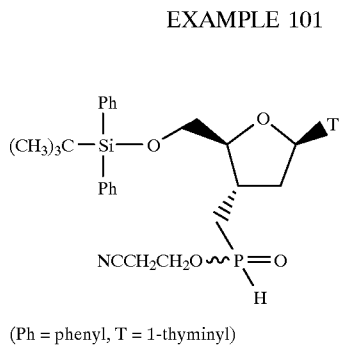

(Ph = phenyl, T = 1-thyminyl)

Dicyclohexylcarbodiimide (104 mg, 506 μmol) is added to a solution of Compound 101 (220 mg, 405 μmol) and 2-cyanoethanol (35 μl, 506 μmol) in tetrahydrofuran (4.1 ml) at 0 °C. After stirring for 4 hours at room temperature, the reaction mixture is filtered and evaporated to give Compound 103 as a viscous clear colourless oil.

$^{31}$P (162 MHz, CDCl$_3$) δ 37.79, 37.54 ppm.

EXAMPLE 102

Compound 104

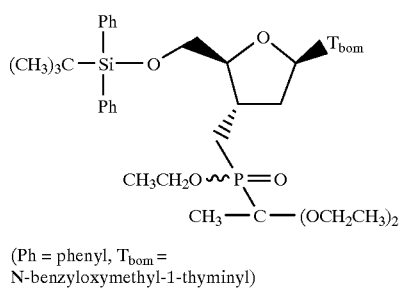

(Ph = phenyl, T$_{bom}$ = N-benzyloxymethyl-1-thyminyl)

Benzyl chloromethyl ether (173 μl, 1.1 mmol) is added dropwise to a solution of Compound 83 (380 mg, 553 μmol) and 1,8-diazabicyclo[5.4.0]undec-7-ene. (DBU) (145 μl, 968 μmol) in acetonitrile (11 ml) at 0° C. After stirring for 2 hours at room temperature, saturated aqueous sodium hydrogen carbonate (20 ml) is added and the aqueous layer extracted with (3×20 ml) ethyl acetate. Drying of the organic extracts over magnesium sulphate and evaporation yields the crude product. Purification via flash column chromatography on silica. eluting with 98% dichloromethane. 2% methanol, gives Compound 104 as a viscous clear colourless oil.

EXAMPLE 103

Compound 105

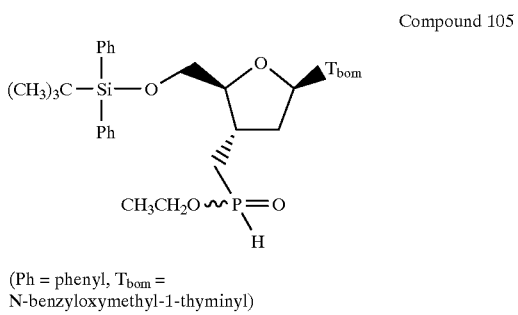

(Ph = phenyl, T$_{bom}$ = N-benzyloxymethyl-1-thyminyl)

Trimethylchlorosilane (613 μl, 4.83 mmol) is added dropwise at 0° C. to a solution of Compound 104 in chloroform containing ethanol (10%) under argon. After stirring for 18 hours at room temperature, saturated aqueous sodium hydrogen carbonate (20 ml) is added, the aqueous layer is extracted with dichloromethane (1×20, 2×10 ml) and the organic extracts dried over magnesium sulphate. Evaporation gives the crude product which is purified by flash column chromatography on silica, eluting with 95% dichloromethane, 5% methanol, to give Compound 105 as a viscous clear colourless oil.

EXAMPLE 104

Compound 106

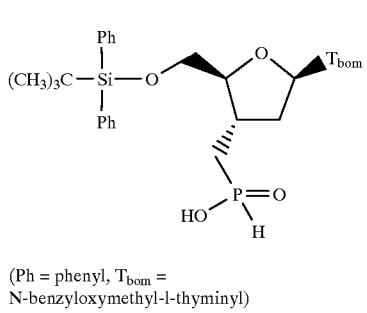

(Ph = phenyl, T$_{bom}$ = N-benzyloxymethyl-l-thyminyl)

A solution of Compound 105 (0.29 g, 420 μmol) in ethanol (1.7 ml), water (0.8 ml) and triethylamine (1.7 ml) is stirred at room temperature for 4 hours. After dilution with ethyl acetate (30 ml), the reaction mixture is washed with cold 0.05M aqueous HCl (2×20 ml), then water (2× 20 ml) and dried over magnesium sulphate. Evaporation yields Compound 106 as a viscous clear colourless oil.

$^{31}$P (162 MHz, CDCl$_3$) δ 35.62 ppm.

EXAMPLE 105

Compound 107

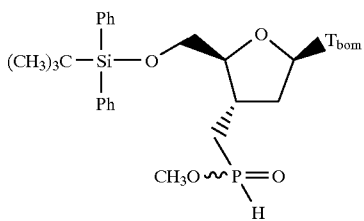

(Ph = phenyl, T$_{bom}$ = N-benzyloxymethyl-l-thyminyl)

Dicyclohexylcarbodiimide (105 mg, 509 μmol) is added to a solution of Compound 106 (270 mg, 407 μmol), 2,6-dimethyl-4-aminopyridine (0.6 mg, 5 μmol) and methanol (21 μl, 509 μmol) in tetrahydrofuran (4.1 ml) at 0° C. After string for 3 hours at room temperature, the reaction mixture is evaporated. Flash column chromatography of the evaporation residue on silica, eluting with 95% ethyl acetate, 5% methanol yields Compound 107 as a viscous clear colourless oil.

$^{31}$P (162 MHz, CDCl$_3$) δ 37.37, 37.08 ppm.

We claim:

1. A compound of formula

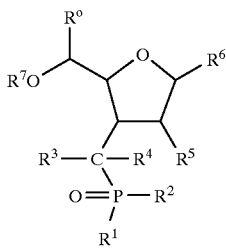

I or salts thereof, where

R$^0$ is hydrogen or together with R$^7$O denotes a C$_{1-C15}$ hydrocarbylidenedioxy group, R$_1$ is hydrogen or R$^1{}_a$, R$^1{}_a$ is R$^1{}_b$ or a protecting group Q, R$^1{}_b$ is C$_1$–C$_{20}$ alkyl, C$_2$–C$_{20}$ alkenyl, C$_3$–C$_{10}$ cycloalkyl, C$_6$–C$_{15}$ aryl, C$_7$–C$_{16}$ aralkyl or a 5- or 6-membered heterocyclic group attached by a carbon atom in the heterocyclic group to the indicated phosphorus atom, R$^2$ is R$^2{}_a$, or —OR$^{15}$ or together with R$^5$ denotes an oxy group —O—, R$^2{}_a$ is a C$_1$–C$_{20}$ aliphatic group, a C$_3$–C$_{10}$ cycloaliphatic group, a C$_6$–C$_{15}$ aromatic group, a C$_7$–C$_{16}$ araliphatic group, or a 5- or 6-membered heterocyclic group attached by a carbon atom in the heterocyclic group to the indicated phosphorus atom, R$^3$ is R$^3{}_a$ or Z, R$^3{}_a$ is hydrogen, halogen, hydroxy, R$^{16}$, —OR$^{16}$, OCOR$^{16}$, —OSO$_2$R$^{16}$, or tri(C$_1$–C$_{15}$ hydrocarbyl)silyloxy, R$^4$ is hydrogen, halogen or R$^{17}$, R$^5$ is R$^5{}_a$ or Z or together with R$^2$ denotes an oxy group —O—, R$^5{}_a$, is hydrogen, halogen, hydroxy, R$^{18}$, —OR$^{18}$, —OCOR$^{18}$, —OSO$_2$R$^{18}$, or tri(C$_1$–C$_{15}$ hydrocarbyl)silyloxy, or together with R$^6$ denotes a C$_1$–C$_{15}$ hydrocarbylidenedioxy group, R$^6$ is halogen, hydroxy, —OR$^{19}$, —OCOR$^{19}$, —OSO$_2$R$^{19}$ or B$^1$, or together with R$^5$ denotes a C$_1$–C$_{15}$ is hydrocarbylidenedioxy group, R$^7$ is hydrogen or R$^7{}_a$, R$^7{}_a$ is R$^{20}$, —COR$^{20}$, —SO$_2$R$^{20}$ or tri(C$_1$–C$_{15}$ hydrocarbyl)silyl, or together with the attached oxygen atom and R$^0$ denotes a C$_1$–C$_{15}$ hydrocarbylidenedioxy group, R$^{15}$ is hydrogen or R$^{15}{}_a$, R$^{15}{}_a$ is a C$_1$ to C$_{10}$ aliphatic group, a C$_3$ to C$_8$ cycloaliphatic group, a C$_6$ to C$_{15}$ aromatic group or a C$_7$ to C$_{16}$ araliphatic group, R$^{16}$, R$^{17}$, R$^{18}$, R$^{19}$, and R$^{20}$, are independently a C$_1$ to C$_{10}$ aliphatic group, a C$_3$ to C$_{10}$ cycloaliphatic group, a C$_6$ to C$_{16}$ aromatic group or a C$_7$ to C$_{30}$ araliphatic group, B$^1$ is a monovalent nucleoside base radical, and Z is a substituted or unsubstituted C$_6$ to C$_{10}$ aryloxythiocarbonyloxy.

2. A compound according to claim 1, in which the aliphatic groups are substituted or unsubstituted alkyl or alkenyl groups, the cycloaliphatic groups are substituted or unsubstituted cycloalkyl groups, the aromatic groups are substituted or unsubstituted aryl groups and the araliphatic groups are substituted or unsubstituted aralkyl groups.

3. A compound according to claim 1, in which the alkyl groups are C$_1$ to C$_8$ alkyl, the alkenyl groups are C$_2$ to C$_4$ alkenyl, the cycloalkyl groups are C$_5$ to C$_8$ cycloalkyl, the aryl groups C$_6$ to C$_{10}$ aryl, the C$_7$ to C$_{16}$ aralkyl group is C$_7$ to C$_9$ aralkyl and the C$_7$ to C$_{30}$ aralkyl groups are C$_7$ to C$_{20}$ aralkyl, any of which are substituted or unsubstituted.

4. A compound according to claim 3, in which the groups are unsubstituted or substituted by halogen, hydroxy, C$_1$ to C$_4$ alkoxy, cyano, nitro, amino, C$_1$ to C$_4$ alkylamino, di(C$_1$–C$_4$ alkyl) amino, tri(C$_1$–C$_{15}$ hydrocarbyl)silyl, tri (C$_1$–C$_{15}$ hydrocarbyl)silyloxy or, in the case of R$^1$ as C$_1$ to C$_8$ alkyl, by a phosphonic ester group.

5. A compound according to claim 1, in which R$^1$ is Q, Q is a C$_1$ to C$_{20}$ hydrocarbyl group, substituted on the carbon atom thereof attached to the indicated phosphorus atom by at least one hydroxy, C$_1$–C$_{10}$ alkoxy, di(C$_1$–C$_{15}$ hydrocarbyl)silyloxy or tri(C$_1$–C$_{15}$ hydrocarbyl)silyloxy group.

6. A compound according to claim 5, in which Q is of formula

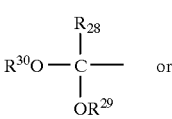

III

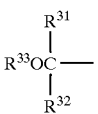

IIIA where R$^{28}$ is hydrogen, C$_1$–C$_{10}$ alkyl, C$_3$–C$_8$ cycloalkyl, C$_6$–C$_{10}$ aryl or C$_7$–C$_{11}$ aralkyl, R$^{29}$ and R$^{30}$ are independently C$_1$–C$_{10}$ alkyl, C$_2$–C$_4$ alkenyl, C$_6$–C$_{10}$ aryl or C$_7$–C$_{13}$aralkyl, R$^{31}$ and R$^{32}$ are independently C$_1$–C$_{10}$ alkyl, or R$^{31}$ is C$_1$–C$_{10}$ akyl and R$^{32}$ is C$_6$–C$_{10}$ aryl, and R$^{33}$ is hydrogen, di(C$_1$–C$_{15}$ hydrocarbyl)silyl or tri(C$_1$–C$_{15}$ hydrocarbyl)silyl.

7. A compound according to claim 6, in which $R^{28}$ is hydrogen or $C_1$–$C_4$ alkyl and $R^{29}$ and $R^{30}$ are each $C_1$–$C_4$ alkyl, $R^{31}$ and $R^{32}$ are $C_1$–$C_4$ alkyl, and $R^{33}$ is hydrogen or branched $C_2$–$C_{10}$ alkyl di($C_1$–$C_4$ alkyl)silyl.

8. A compound according to any of the preceding claims, in which where tri($C_1$–$C_{15}$ hydrocarbyl)silyl group is present it is a tri($C_1$–$C_6$ alkyl)silyl, $C_1$–$C_5$ alkyldi($C_6$–$C_8$ aryl)silyl, or branched $C_2$–$C_{10}$ alkyl di ($C_1$–$C_4$ alkyl)silyl.

9. A compound according to claim 1 in which at least $R^0$ together with $R^7O$ or $R^5$ together with $R^6$ independently form a $C_1$–$C_{15}$ hydrocarbylidenedioxy group of the formula

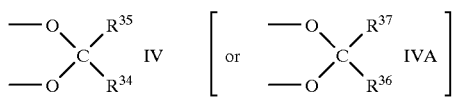

where $R^{34}$ and $R^{35}$ are independently hydrogen, $C_1$ to $C_{10}$ alkyl, $C_3$ to $C_8$ cycloalkyl or $C_6$ to $C_{10}$ aryl.

10. A compound according to claim 9, in which $R^{34}$ and $R^{35}$ are each independently a $C_1$ to $C_4$ alkyl.

11. A compound according to claim 1, in which $R^6$ as a monovalent nucleoside base radical is unsubstituted or substituted thyminyl, uracilyl, cytosinyl or adeninyl.

12. A compound according to claim 1, in which: $R^1$ is hydrogen, $C_1$–$C_{14}$ alkyl, $C_6$–$C_{10}$ aryl, a protecting group Q of the formulas III or III A

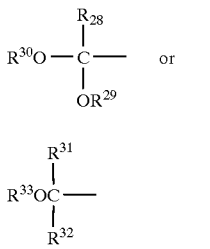

where $R^{28}$ is hydrogen, $C_1$–$C_{10}$ alkyl, $C_3$–$C_8$ cycloalkyl, $C_6$–$C_{10}$ aryl or $C_7$–$C_{11}$ aralkyl, $R^{29}$ and $R^{30}$ are independently $C_1$–$C_{10}$ alkyl, $C_2$–$C_4$ alkenyl, $C_8$–$C_{10}$ aryl or $C_7$–$C_{13}$ aralkyl, $R^{31}$ and $R^{32}$ are independently $C_1$–$C_{10}$ alkyl, or $R^{31}$ is $C_1$–$C_{10}$ alkyl and $R^{32}$ is $C_6$–$C_{10}$ aryl, and $R^{33}$ is hydrogen, di($C_1$–$C_{15}$ hydrocarbyl)silyl or tri(($C_1$–$C_{15}$ hydrocarbyl) silyl, $R^2$ is $R^2_a$ which is $C_1$ to $C_4$ alkyl, $C_2$ to $C_4$ alkenyl, $C_5$ to $C_8$ cycloalkyl, $C_6$ to $C_{10}$ aryl, or $C_7$ to $C_9$ aralkyl, or $R^2$ is —$OR^{15}$, where $R^{15}$ is hydrogen or unsubstituted or substituted $C_1$–$C_4$ alkyl, or $R^2$ together with $R^5$ denotes an oxy group, $R^3$ is hydrogen, halogen, hydroxy, —$OCOR^{16}$ or $OSO_2R^{16}$ where $R^{16}$ is substituted or unsubstituted $C_1$ to $C_4$ alkyl or $C_6$ to $C_{10}$ aryl, tri($C_1$–$C_6$ alkyl)silyloxy or $C_1$–$C_4$ alkyl- or halogen- substituted phenyloxythiocarbonyloxy, and $R^4$ is hydrogen or halogen, $R^5$ is hydrogen, hydroxy or —$OR^{15}$, —$OCOR^{18}$ or —$OSO_2R^{18}$ where $R^{18}$ is unsubstituted or substituted $C_1$ to $C_4$ alkyl, unsubstituted or substituted $C_8$ to $C_{10}$ aryl, tri($C_1$–$C_{15}$ hydrocarbyl)silyloxy, or together with $R^2$ denotes an oxy group, or together with $R^6$ denotes a hydrocarbylidenedioxy group of formula IV

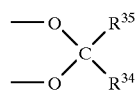

where $R^{34}$ and $R^{35}$ are independently $C_1$ to $C_4$ alkyl, $R^6$ is a monovalent nucleoside base radical $B^1$, hydroxy or —$OCOR^{19}$ where $R^{19}$ is unsubstituted or substituted $C_1$ to $C_4$ alkyl, or together with $R^5$ denotes a hydrocarbylidenedioxy group of formula IV, where $R^{34}$ and $R^{35}$ are independently $C_1$ to $C_4$ alkyl. $R^7$ is hydrogen, substituted or unsubstituted $C_1$ to $C_4$ alkyl, substituted or unsubstituted $C_7$ to $C_{20}$ aralkyl, —$COR^{20}$ or —$SO_2R^{20}$ where $R^{20}$ is substituted or unsubstituted $C_1$ to $C_4$ alkyl or substituted or unsubstituted $C_6$ to $C_{10}$ aryl, or ($C_1$ to $C_6$ alkyl) di ($C_6$–$C_8$ aryl) silyl, or together with the attached oxygen atom and $R^0$ denotes a hydrocarbylidenedioxy group of formula IV where $R^{34}$ and $R^{35}$ are independently $C_1$ to $C_4$ alkyl.

13. A compound according to claim 12, in which $R^1$ is hydrogen, methyl or methyl substituted by P(O)(OCH$_2$CH$_3$)$_2$, phenyl, a protecting group Q of formula III or IIIA

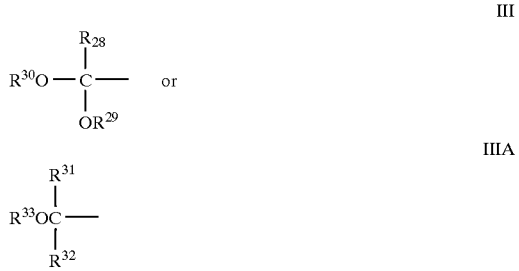

wherein $R^{28}$ is hydrogen or $C_1$–$C_4$ alkyl and $R^{29}$ and $R^{30}$ are each $C_1$–$C_4$ alkyl, $R^{31}$ and $R^{32}$ are $C_1$–$C_4$ alkyl, and $R^{33}$ is hydrogen or branched $C_2$–$C_{10}$ alkyl di($C_1$–$C_4$ alkyl)silyl, $R^2$ is methyl, ethyl, vinyl, allyl, cyclophentyl, cyclohexyl, methylcyclohexyl, phenyl, tolyl, naphthyl, benzyl, hydroxy, methoxy, ethoxy, 2-cyanoethoxy, or isobutoxy, or together with $R^5$ denotes an oxy group, $R^3$ is hydrogen, fluorine, chlorine, hydroxy, —$OCOR^{16}$ or —$OSO_2R^{16}$ where $R^{16}$ is methyl, ethyl, phenyl, tolyl or naphthyl, trimethylsilyloxy or p-tolyloxythiocarbonyloxy and $R^4$ is hydrogen, $R^5$ hydrogen, hydroxy or —$OR^{18}$, —$OCOR^{18}$ or —$OSO_2R^{18}$ where $R^{18}$ is methyl, ethyl, phenyl, tolyl or naphthyl, tert-butyldiphenylsilyloxy or thexyldimethylsilyloxy, or together with $R^2$ denotes an oxy group or together with $R^6$ denotes an isopropylidenedioxy group, $R^6$ is thyminyl, N-benzyloxymethyl thyminyl, uracilyl, 5-methylcytosinyl, adeninyl, N-benzoyladeninyl, N-(N-methyl-2-pyrrolidinylidene)-5-methylcytosinyl, hydroxy, or —$OCOR^{19}$ where $R^{19}$ is methyl or ethyl, or together with $R^5$ denotes an isopropylidenedioxy group, $R^7$ is hydrogen, methyl, ethyl, benzyl, diphenylmethyl, triphenylmethyl, dimethoxytriphenylmethyl, —$COR^{20}$ or —$SO_2R^{20}$ where $R^{20}$ is phenyl, tolyl or naphthyl, or tert-butyldiphenylsilyl, or together with the attached oxygen atom and $R^0$ denotes an isopropylidenedioxy group.

14. A compound according to claim 1 where $R^1$ is hydrogen, methyl, methyl substituted by —P(O)(OCH$_2$CH$_3$)$_2$, phenyl, a group of formulas III or IIIA

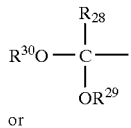   III or

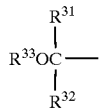   IIIA where $R^{28}$ is hydrogen or methyl and $R^{29}$ and $R^{30}$ are each ethyl, where $R^{31}$ and $R^{32}$ are each methyl and $R^{33}$ is hydrogen or tert-butyldimethylsilyl, $R^2$ is methyl, hydroxy, methoxy, ethoxy, 2-cyanoethoxy, or isobutoxy, or together with $R^5$ denotes an oxy group, $R^3$ is hydrogen, hydroxy, acetoxy, trimethylsilyloxy or p-tolyloxythiocarbonyloxy, $R^4$ is hydrogen, $R^5$ is hydroxy, acetoxy, tert-butyldiphenylsilyloxy, thexyldimethylsilyloxy or together with $R^2$ denotes an oxy group and $R^6$ is hydroxy, acetoxy, thyminyl, N-benzyloxymethylthyminyl, uracilyl, 5-methylcytosinyl, adeninyl, N-benzoyladeninyl, or N-(N-methyl-2-pyrrolidinylidene)-5-methylcytosinyl or $R^5$ and $R^6$ together denote isopropylidenedioxy; and $R^7$ is hydrogen, benzoyl, acetyl, benzyl, triphenylmethyl, dimethoxytriphenylmethyl or tert-butyldiphenylsilyl.

15. A compound according to claim 1 which is of formula V or VII wherein in formula V

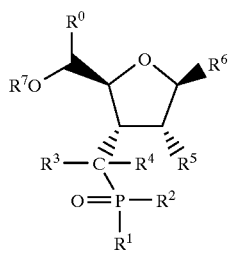   V $R^1$ is hydrogen or $R^1_a$;

and in formula

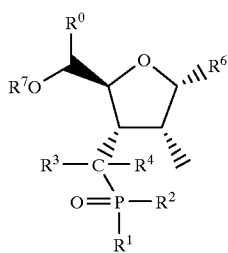   VII $R^1$ is hydrogen or $R^1_a$.

16. A method of preparing a compound comprising the step of reacting a compound of formula

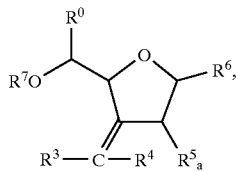   XI with a compound of formula

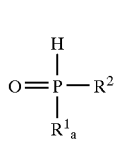   XII in the presence of a free radical initiator where $R^0$ is hydrogen or together with $R^7O$ denotes a $C_1$–$C_{15}$ hydrocarbylidenedioxy group, $R^1_a$ is $R^1_b$ or a protecting group Q, $R^1_b$ is $C_1$–$C_{20}$ alkyl, $C_2$–$C_{20}$ alkenyl, $C_3$–$C_{10}$ cycloakyl, $C_6$–$C_{15}$ aryl, $C_7$–$C_{16}$ aralkyl or a 5- or 6-membered heterocyclic group attached by a carbon atom in the heterocyclic group to the indicated phosphorus atom, $R^2$ is $R^2_a$ or —$OR^{15}$ or together with $R^5$ denotes an oxy group —O—, $R^2_a$ is a $C_1$–$C_{20}$ aliphatic group, a $C_3$–$C_{10}$ cycloaliphatic group, a $C_6$–$C_{15}$ aromatic group, a $C_7$–$C_{16}$ araliphatic group, or a 5- or 6-membered heterocyclic group attached by a carbon atom in the heterocyclic group to the indicated phosphorus atom, $R^3_a$ is hydrogen, halogen, hydroxy, $R^{16}$, —$OR^{16}$, $OCOR^{16}$, —$OSO_2R^{16}$, or tri($C_1$–$C_{15}$ hydrocarbyl)silyloxy, $R^4$ is hydrogen, halogen or $R^{17}$, $R^5_a$ is hydrogen, halogen, hydroxy, $R^{18}$, —$OR^{18}$, —$OCOR^{18}$, —$OSO_2R^{18}$, or tri($C_1$–$C_{15}$ hydrocarbyl)silyloxy, or together with $R^6$ denotes a $C_1$–$C_{15}$ hydrocarbylidenedioxy group, $R^6$ is halogen, hydroxy, —$OR^{19}$, —$OCOR^{19}$, —$OSO_2R^{19}$ or $B^1$, $R^7$ is hydrogen or $R^7_a$, $R^7_a$ is $R^{20}$, —$COR^{20}$, —$SO_2R^{20}$ or tri($C_1$–$C_{15}$ hydrocarbyl)silyl, or together with the attached oxygen atom and $R^0$ denotes a $C_1$–$C_{15}$ hydrocarbylidenedioxy group, $R^{15}$ is hydrogen or $R^{15}_a$, $R^{15}_a$ is a $C_1$ to $C_{10}$ aliphatic group, a $C_3$ to $C_8$ cycloaliphatic group, a $C_6$ to $C_{15}$ aromatic group or a $C_7$ to $C_{16}$ araliphatic group, $R^{16}$, $R^{17}$, $R^{18}$, $R^{19}$ and $R^{20}$ are independently a $C_1$ to $C_{10}$ aliphatic group, a $C_3$ to $C_{10}$ cycloaliphatic group, a $C_6$ to $C_{15}$ aromatic group or a $C_7$ to $C_{30}$ araliphatic group, $B^1$ is a monovalent nucleoside base radical, and Z is substituted or unsubstituted $C_6$ to $C_{10}$ aryloxythiocarbonyloxy.

17. A method of preparing a compound comprising the step of:

reacting a compound of formula XIV

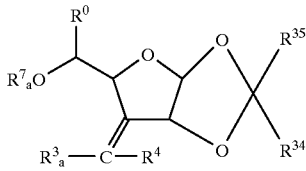
XIV with a compound of formula

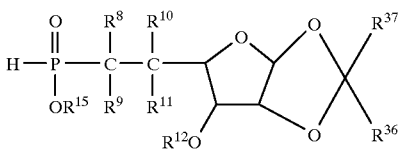
XXII in the presence of a free radical initiator to produce a compound of formula I

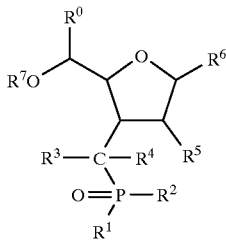
I where $R^0$ is hydrogen, $R^1$ is a group of formula II, $R^2$ is —$OR^{15}$, $R^3$ is $R^3_a$ wherein $R^3_a$ is hydrogen, halogen, hydroxy, $R^{16}$, —$OR^{16}$, $OCOR^{16}$, —$OSO_2R^{16}$, or tri($C_1$–$C_{15}$ hydrocarbyl)silyloxy, $R^4$ is hydrogen, halogen or $R^{17}$, $R^5$ and $R^6$ together and $R^{13}$ and $R^{14}$ together each denote a $C_1$ to $C_{15}$ hydrocarbylidenedioxy group, $R^7$ is $R^7_a$, $R^7_a$ is $R^{20}$, —$COR^{20}$, —$SO_2R^{20}$ or tri($C_1$–$C_{15}$ hydrocarbyl)silyl, $R^8$ is hydrogen, halogen, hydroxy, $R^{21}$, —$OR^{21}$, —$OCOR^{21}$, —$OSO_2R^{21}$ or together with $R^{10}$ denotes a valence bond, $R^9$ is hydrogen, halogen or $R^{22}$, $R^{10}$ is hydrogen, halogen, hydroxy, $R^{23}$, —$OR^{23}$, —$OCOR^{23}$ or —$OSO_2R^{23}$, or together with $R^8$ denotes a valence bond, $R^{11}$ is hydrogen, halogen or $R^{24}$, $R^{12}$ is hydrogen or $R^{12}_a$, $R^{12}_a$ is $R^{25}$, —$COR^{25}$, —$SO_2R^{25}$, or tri ($C_1$–$C_{15}$ hydrocarbyl silyl, $R^{15}$ is hydrogen or $R^{15}_a$, $R^{15}_a$ is a $C_1$ to $C_{10}$ aliphatic group, a $C_3$ to $C_8$ cycloaliphatic group, a $C_6$ to $C_{15}$ aromatic group or a $C_7$ to $C_{16}$, araliphatic group, $R^{16}$, $R^{17}$, $R^{20}$, $R^{21}$, $R^{22}$, $R^{23}$, $R^{24}$, and $R^{25}$ are independently a $C_1$ to $C_{10}$ aliphatic group, a $C_3$ to $C_{10}$ cycloaliphatic group, a $C_6$ to $C_{15}$ aromatic group or a $C_7$ to $C_{30}$ araliphatic group, and $R^{34}$ to $R^{37}$ are independently hydrogen, $C_1$ to $C_{10}$ alkyl, $C_3$ to $C_8$ cycloalkyl or $C_6$ to $C_{10}$ aryl.

18. A method of preparing a compound wherein the method comprises the step of: reacting an aldehyde of formula

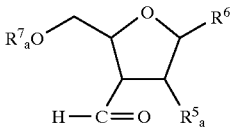
XXIII with a compound of formula XII

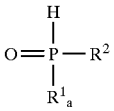
XII in the presence of a base to produce a compound of formula I

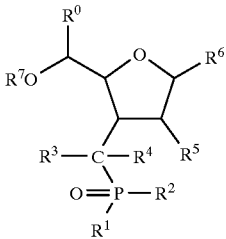
I were $R^0$ is hydrogen, $R^1$ is $R^1_a$, $R^1_a$ is $R^1_b$ or a protecting group Q, $R^1_b$ is $C_1$–$C_{20}$ alkyl, $C_2$–$C_{20}$ alkenyl, $C_3$–$C_{10}$ cycloalkyl, $C_6$–$C_{15}$ aryl, $C_7$–$C_{16}$ aralkyl or a 5- or 6-membered heterocyclic group attached by a carbon atom in the heterocyclic group to the indicated phosphorus atom, $R^2$ is $R^2_a$ or —$OR^{15}$ or together with $R^5$ denotes an oxy group —O—, $R^2_a$ is a $C_1$–$C_{20}$ aliphatic group, a $C_3$–$C_{10}$ cycloaliphatic group, a $C_6$–$C_{15}$ aromatic group, a $C_7$–$C_{16}$ araliphatic group, or a 5- or 6-membered heterocyclic group attached by a carbon atom in the heterocyclic group to the indicated phosphorus atom, $R^3$ is hydroxy, $R^4$ is hydrogen, $R^5$ is $R^5_a$, $R^5_a$ is hydrogen, halogen, hydroxy, $R^{18}$, —$OR^{18}$, —$OCOR^{18}$, —$OSO_2R^{16}$, or tri($C_1$–$C_{15}$ hydrocarbyl) silyloxy, or together with $R^6$ denotes a $C_1$–$C_{15}$ hydrocarbylidenedioxy group, $R^6$ is halogen, hydroxy, —$OR^{19}$, —$OCOR^{19}$, —$OSO_2R^{19}$ or $B^1$, $R^7$ is $R^7_a$, $R^7_a$ is $R^{20}$, —$COR^{20}$, —$SO_2R^{20}$ or tri($C_1$–$C_{15}$ hydrocarbyl)silyl, $R^{15}$ is hydrogen or $R^{15}_a$, $R^{15}_a$ is a $C_1$ $C_{10}$ aliphatic group, a $C_3$ to $C_8$ cycloaliphatic group, a $C_6$ to $C_{15}$ aromatic group or a $C_7$ to $C_{16}$ araliphatic group, $R^{18}$, $R^{19}$, $R^{20}$, are independently a $C_1$ to $C_{10}$ araliphatic group, a $C_3$ to $C_{10}$ cycloaliphatic group, a $C_6$ to $C_{15}$ aromatic group or a $C_7$ to $C_{30}$ araliphatic group, and $B^1$ is a monovalent nucleoside base radical.

19. A method of preparing a compound comprising the steps of:

reacting a compound of formula XII

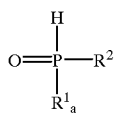

XII with a silylating agent to give a P(III) silyl compound; and, reacting the P(III) silyl compound with an aldehyde of formula XXIII

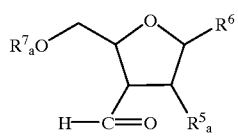

XXIII to produce a compound of formula I

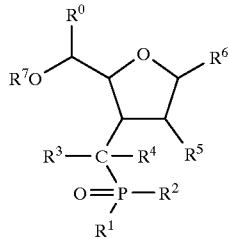

I where $R^0$ is hydrogen, $R_1$ is $R^1_a$, $R^1_a$ is $R^1_b$ or a protecting group Q, $R^1_b$ is $C_1$–$C_{20}$ alkyl, $C_2$–$C_{20}$ alkenyl, $C_3$–$C_{10}$ cycloalkyl, $C_6$–$C_{15}$ aryl, $C_7$–$C_{16}$ aralkyl or a 5- or 6-membered heterocyclic group attached by a carbon atom in the heterocyclic group to the indicated phosphorus atom, $R^2$ is $R^2_a$ or —$OR^{15}$ or together with $R^5$ denotes an oxy group —O—, $R^2_a$ is a $C_1$–$C_{20}$ aliphatic group, a $C_3$–$C_{10}$ cycloaliphatic group, a $C_6$–$C_{15}$ aromatic group, a $C_7$–$C_{16}$ araliphatic group, or a 5- or 6-membered heterocyclic group attached by a carbon atom in the heterocyclic group to the indicated phosphorus atom, $R^3$ is hydroxy, $R^4$ is hydrogen, $R^5$ is $R^5_a$, $R^5_a$ is hydrogen, halogen, hydroxy, $R^{15}$, —$OR^{18}$, —$OCOR^{18}$, —$OSO_2R^{18}$, or tri($C_1$–$C_{15}$ hydrocarbyl)silyloxy, or together with $R^5$ denotes a $C_1$–$C_{15}$ hydrocarbylidenedioxy group, $R^6$ is halogen, hydroxy, —$OR^{19}$, —$OCOR^{19}$, —$OSO_2R^{19}$ or $B^1$, or together with $R^5$ denotes a $C_1$–$C_{15}$ is hydrocarbyidenedioxy group, $R^7$ is $R^7_a$, $R^7_a$ is $R^{20}$, —$COR^{20}$, —$SO_2R^{20}$ or tri($C_1$–$C_{15}$ hydrocarbyl) silyl, or together with the attached oxygen atom and $R^0$ denotes a $C_1$–$C_{15}$ hydrocarbylidenedioxy group, $R^{15}$ is hydrogen or $R^{15}_a$, $R^{15}_a$ is a $C_1$ to $C_{10}$ aliphatic group, a $C_3$ to $C_8$ cycloaliphatic group, a $C_6$ to $C_{15}$ aromatic group or a $C_7$ to $C_{16}$ araliphatic group, $R^{16}$, $R^{19}$, and $R^{20}$, are independently a $C_1$ to $C_{10}$ aliphatic group, a $C_3$ to $C_{10}$ cycloaliphatic group, a $C_6$ to $C_{15}$ aromatic group or a $C_7$ to $C_{30}$ araliphatic group, and $B^1$ is a monovalent nucleoside base radical.

20. A method of preparing a compound comprising the step of:

reacting a compound of formula

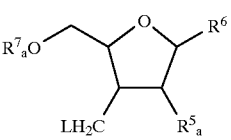

XXIV with a compound of formula XII

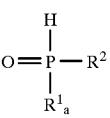

XII to produce a compound of formula I

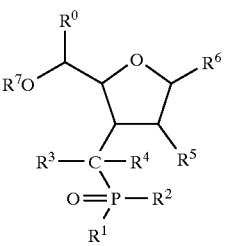

I where $R^0$ is hydrogen, $R_1$ is $R^1_a$, $R^1_a$ is $R^1_b$ or a protecting group Q, $R^1_b$ is $C_1$–$C_{20}$ alkyl, $C_2$–$C_{20}$ alkenyl, $C_3$–$C_{10}$ cycloalkyl, $C_6$–$C_{15}$ aryl, $C_7$–$C_{16}$, aralkyl or a 5- or 6-membered heterocyclic group attached by a carbon atom in the heterocyclic group to the indicated phosphorus atom, $R^2$is $R^2_a$ or —$OR^{15}$ or together with R denotes an oxy group —O—, $R^2_a$ is a $C_1$–$C_{20}$ aliphatic group, a $C_3$–$C_{10}$ cycloaliphatic group, a $C_6$–$C_{15}$ aromatic group, a $C_7$–$C_{16}$ araliphatic group or a 5- or 6-membered heterocyclic group attached by a carbon atom in the heterocyclic group to the indicated phosphorus atom, $R^3$ is hydroxy, $R^4$ is hydrogen, $R^5$ is $R^5_a$, $R^5_a$ is hydrogen, halogen, hydroxy, $R^{18}$, —$OR^{18}$, —$OCOR^{18}$, —$OSO_2R^{18}$, or tri($C_1$–$C_{15}$ hydrocarbyl) silyloxy, or together with $R^6$ denotes a $C_1$–$C_{15}$ hydrocarbylidenedioxy group, $R^6$ is halogen, hydroxy, —$OR^{19}$, —$OCOR^{19}$, —$OSO_2R^{19}$ or $B^1$, $R^7$ is $R^7_a$, $R^7_a$ is $R^{20}$, —$COR^{20}$, —$SO_2R^{20}$ or tri($C_1$–$C_{15}$ hydrocarbyl)silyl, $R^{15}$ is hydrogen or $R^{15}_a$, $R^{15}_a$ is a $C_1$ to $C_{10}$ aliphatic group, a $C_3$ to $C_8$ cycloaliphatic group, a $C_6$ to $C_{15}$ aromatic group or a $C_7$ to $C_{16}$ araliphatic group, $R^{18}$, $R^{19}$, and $R^{20}$, are independently a $C_1$ to $C_{10}$ aliphatic group a $C_3$ to $C_{10}$ cycloaliphatic group, a $C_6$ $C_{15}$ aromatic group or a $C_7$ to $C_{30}$ araliphatic group, $B^1$ is a monovalent nucleoside base radical and L is a leaving atom or group.

21. A method of preparing a compound comprising the step of: reacting a compound of formula I

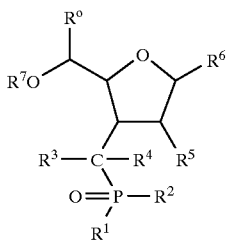

I with an aldehyde of formula

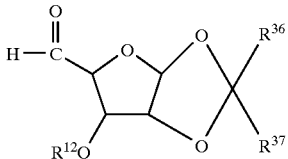

XXV in the presence of a strong base to produce a compound of formula I where $R^1$ is a group of formula II

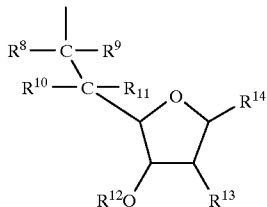

II in which $R^8$ and $R^{10}$ together denote a valence bond and $R^{13}$ and $R^{14}$ together denote a $C_1$ to $C_{15}$ hydrocarbylidenedioxy group and wherein $R^0$ is hydrogen, $R^1$ is an alkyl group substituted by a phosphonic ester group, $R^2$ is —$OR^{15}$, $R^{15}$ is hydrogen or $R^{15}{}_a$, $R^{15}{}_a$ is a $C_1$ to $C_{10}$ aliphatic group, a $C_3$ to $C_8$ cycloaliphatic group, a $C_6$ to $C_{15}$ aromatic group or a $C_7$ to $C_{16}$ araliphatic group, $R^3$ is $R^3{}_a$ or Z, $R^3{}_a$ is hydrogen, halogen, hydroxy. $R^{16}$, —$OR^{16}$, $OCOR^{16}$, —$OSO_2R^{16}$, or tri($C_1$–$C_{15}$ hydrocarbyl)silyloxy, $R^4$ is hydrogen, halogen or $R^{17}$, Z is a substituted or unsubstituted $C_6$ to $C_{10}$ aryloxythiocarbonyloxy, $R^5$ and $R^6$ together denote a $C_1$ to $C_{15}$ hydrocarbylidenedioxy group and $R^7$ is $R^7{}_a$, $R^7{}_a$ is $R^{20}$, —$COR^{20}$, —$SO_2R^{20}$ or tri($C_1$–$C_{15}$ hydrocarbyl)silyl, $R^9$ is hydrogen, halogen or $R^{22}$, $R^{11}$ is hydrogen, halogen or $R^{24}$, $R^{12}$ is hydrogen or $R^{12}{}_a$, $R^{12}{}_a$ is $R^{25}$, —$COR^{25}$, —$SO_2R^{25}$ or tri ($C_1$–$C_{15}$ hydrocarbyl) silyl, $R^{16}$, $R^{17}$, $R^{20}$, $R^{22}$, $R^{24}$, and $R^{25}$ are independently a $C_1$ to $C_{10}$ aliphatic group, a $C_3$ to $C_{10}$ cycloaliphatic group, a $C_6$ to $C_{15}$ aromatic group or a $C_7$ to $C_{30}$ araliphatic group, and $R^{36}$ and $R^{37}$ are independently hydrogen, $C_1$ to $C_{10}$ alkyl, $C_3$ to $C_8$ cycloalkyl or $C_6$ to $C_{10}$ aryl.

22. A method of producing a dinucleotide analogue or precursor thereof comprising the step of:
reacting a compound of formula I

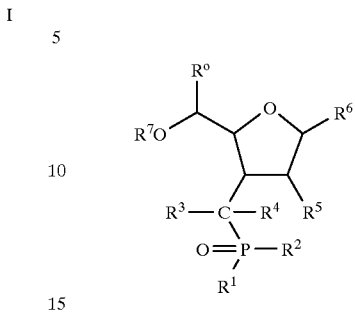

I where $R^1$ is hydrogen, $R^0$ is hydrogen or together with $R^7O$ denotes a $C_1$–$C_{15}$ hydrocarbylidenedioxy group $R^2$ is $R^2{}_a$ or —$OR^{15}$ or together with $R^5$ denotes an oxy group —O—, $R^2{}_a$ is a $C_1$–$C_{20}$ aliphatic group, a $C_3$–$C_{10}$ cycloaliphatic group, a $C_6$–$C_{15}$ aromatic group, a $C_7$–$C_{16}$ araliphatic group, or a 5- or 6-membered heterocyclic group attached by a carbon atom in the heterocyclic group to the indicated phosphorus atom, $R^3$ is $R^3{}_a$ or Z, $R^3{}_a$ is hydrogen, halogen, hydroxy, $R^{16}$, —$OR^{16}$, $OCOR^{16}$, —$OSO_2R^{16}$, or tri($C_1$–$C_{15}$ hydrocarbyl)silyloxy, $R^4$ is hydrogen, halogen or $R^{17}$, $R^5$ is $R^5{}_a$ or Z or together with $R^2$ denotes an oxy group —O—, $R^5{}_a$ is hydrogen, halogen, hydroxy, $R^{18}$, —$OR^{18}$, —$OCOR^{18}$, —$OSO_2R^{18}$, or tri($C_1$–$C_{15}$ hydrocarbyl)silyloxy, or together with $R^6$ denotes a $C_1$–$C_{15}$ hydrocarbylidenedioxy group, $R^6$ is halogen, hydroxy, —$OR^{19}$, —$OCOR^{19}$, —$OSO_2R^{19}$ or $B^1$, or together with $R^5$ denotes a $C_1$–$C_{15}$ is hydrocarbylidenedioxy group, $R^7$ is hydrogen or $R^7{}_a$, $R^7{}_a$ is $R^{20}$, —$COR^{20}$, —$SO_2R^{20}$ or tri($C_1$–$C_{15}$ hydrocarbyl)silyl, or together with the attached oxygen atom and $R^0$ denotes a $C_1$–$C_{15}$ hydrocarbylidenedyioxy group, $R^{15}$ is hydrogen or $R^{15}{}_a$, $R^{15}{}_a$ is a $C_1$ to $C_{10}$ aliphatic group, a $C_3$ to $C_8$ cycloaliphatic group, a $C_6$ to $C_{15}$ aromatic group or a $C_7$ to $C_{16}$ araliphatic group, $R^{16}$, $R^{17}$, $R^{18}$, $R^{19}$, $R^{20}$ and $R^{21}$ are independently a $C_1$ to $C_{10}$ aliphatic group, $C_3$ to $C_{10}$ cycloaliphatic group, a $C_6$ to $C_{15}$ aromatic group or a $C_7$ to $C_{30}$ araliphatic group, $B^1$ is a monovalent nucleoside base radical, and Z is substituted or unsubstituted to $C_6$ to $C_{10}$ aryloxythiocarbonyloxy,
with a compound of formula

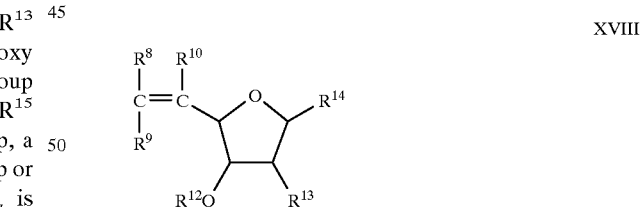

XVIII in the presence of a free radical initiator, to produce a dinucleotide analogue or precursor thereof where $R^8$ is hydrogen, halogen, hydroxy, $R^{21}$, —$OR^{21}$, —$OCOR^{21}$, —$OSO_2R^{21}$ or together with $R^{10}$ denotes a valence bond, $R^9$ is hydrogen, halogen or $R^{22}$, $R^{10}$ is hydrogen, halogen, hydroxy, $R^{23}$, —$OR^{23}$, —$OCOR^{23}$ or —$OSO_2R^{23}$, or together with $R^8$ denotes a valence bond, $R^{11}$ is hydrogen, halogen or $R^{24}$, $R^{12}$ is hydrogen or $R^{12}{}_a$, or $R^{12}O$— together with $R^{13}$ denotes a $C_1$–$C_{15}$ hydrocarbylidenedioxy group, $R^{12}{}_a$ is $R^{25}$, —$COR^{25}$, —$SO_2R^{25}$ or tri ($C_1$–$C_{15}$ hydrocarbyl silyl,
$R^{13}$ or $R^{13}{}_a$ or Z, $R^{13}{}_a$ is hydrogen, halogen, hydroxy, $R^{26}$, —$OR^{26}$, —$OCOR^{26}$, —$OSO_2R^{26}$ or tri($C_1$–$C_{15}$ hydrocarbyl)silyloxy, $R^{14}$ is halogen, hydroxy, —$OR^{27}$, —$OCOR^{27}$, —$OSO_2R^{27}$ or $B^2$ or together with $R^{13}$ denotes a $C_1$–$C_{15}$ hydrocarbylidenedioxy group, where $R^{27}$ is a $C_1$ to $C_{10}$ aliphatic group, a $C_3$ to $C_{10}$ cycloaliphatic group, a $C_6$ to $C_{15}$ aromatic group or a $C_7$ to $C_{30}$ araliphatic group and $B^2$ is a monovalent nucleoside base radical and where $R^{21}$, $R^{22}$, $R^{23}$, $R^{24}$, $R^{25}$, $R^{26}$ and $R^{27}$ are independently a $C_1$ to $C_{10}$ aliphatic group, a $C_3$ to $C_{10}$ cycloaliphatic group, a $C_6$ to $C_{15}$ aromatic group or a $C_7$ to $C_{30}$ araliphatic group.

23. A method for preparing a dinucleotide analogue comprising the step of:

glycosylating a compound of formula I

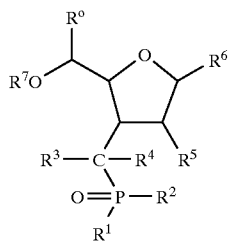

I where $R_1$ is a group of formula II

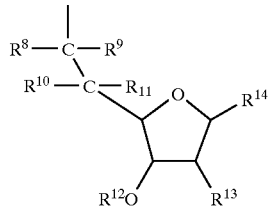

II with a base of formula $B^1H$ where B1 is a monovalent nucleoside base radical to produce a dinucleotide analogue and wherein $R^0$ is hydrogen or together with $R^7O$ denotes a $C_1$–$C_{15}$ hydrocarbylidenedioxy group, $R^2$ is —$OR^{15}$, $R^3$ is $R^3_a$ or Z, $R^3_a$ is hydrogen, halogen, hydroxy, $R^{16}$, —$OR^{16}$, $OCOR^{16}$, —$OSO_2R^{16}$, or tri($C_1$–$C_{15}$ hydrocarbyl)silyloxy, $R^4$ is hydrogen, halogen or $R^{17}$, $R^5$ is —$OCOR^{18}$, $R^6$ is —$OCOR^{19}$, $R^7$ is hydrogen or $R^7_a$, $R^7_a$ is $R^{20}$, —$COR^{20}$, —$SO_2R^{20}$ or tri($C_1$–$C_{15}$ hydrocarbyl)silyl, or together with the attached oxygen atom and $R^0$ denotes a $C_1$–$C_{15}$ hydrocarbylidenedioxy group, $R^8$ is hydrogen, halogen, hydroxy, $R^{21}$, —$OR^2$, —$OCOR^{21}$, —$OSO_2R^{21}$ or together with $R^{10}$ denotes a valence bond, $R^9$ is hydrogen, halogen or $R^{22}$, $R^{10}$ is hydrogen, halogen, hydroxy, $R^{23}$, —$OR^{23}$, —$OCOR^{23}$ or —$OSO_2R^{23}$, or together with $R^8$ denotes a valence bond, $R^{11}$ is hydrogen, halogen or $R^{24}$, $R^{12}$ is hydrogen or $R^{12}_a$, or $R^{12}O$— together with $R^{13}$ denotes a $C_1$–$C_{15}$ hydrocarbylidenedioxy group, $R^{12}_a$ is $R^{25}$, —$COR^{25}$, —$SO_2R^{25}$ or tri ($C_1$–$C_{15}$ hydrocarbyl) silyl, $R^{13}$ is —$OCOR^{26}$, $R^{14}$ is —$OCOR^{27}$, $R^{15}$ is hydrogen or $R^{15}_a$, $R^{15}_a$ is a $C_1$ to $C_{10}$ aliphatic group, a $C_3$ to $C_8$ cycloaliphatic group, a $C_6$ to $C_{15}$ aromatic group or a $C_7$ to $C_{16}$ araliphatic group, $R^{16}$, $R^{17}$ $R^{18}$, $R^{19}$, $R^{20}$, $R^{21}$, $R^{22}$, $R^{23}$, $R^{24}$, $R^{25}$, $R^{26}$ and $R^{27}$ are independently a $C_1$ to $C_{10}$ aliphatic group, a $C_3$ to $C_{10}$ cycloaliphatic group, a $C_6$ to $C_{15}$ aromatic group or a $C_7$ to $C_{30}$ araliphatic group, and Z is substituted or unsubstituted $C_6$ to $C_{10}$ aryloxythiocarbonyloxy.

24. The compound of claim 1 or a pharmaceutically acceptable salt thereof in a pharmaceutical composition.

* * * * *